(12) United States Patent
Dewey et al.

(10) Patent No.: US 10,127,346 B2
(45) Date of Patent: Nov. 13, 2018

(54) SYSTEMS AND METHODS FOR INTERPRETING A HUMAN GENOME USING A SYNTHETIC REFERENCE SEQUENCE

(75) Inventors: Frederick Dewey, Redwood City, CA (US); Euan A. Ashley, Menlo Park, CA (US); Matthew Wheeler, Sunnyvale, CA (US); Michael Snyder, Stanford, CA (US); Carlos Bustamante, Emerald Hills, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 978 days.

(21) Appl. No.: 13/445,923

(22) Filed: Apr. 13, 2012

(65) Prior Publication Data

US 2013/0073217 A1 Mar. 21, 2013
US 2015/0370963 A9 Dec. 24, 2015

Related U.S. Application Data

(60) Provisional application No. 61/474,749, filed on Apr. 13, 2011, provisional application No. 61/502,236, filed on Jun. 28, 2011.

(51) Int. Cl.
| | |
|---|---|
| *G06N 5/02* | (2006.01) |
| *G06F 19/12* | (2011.01) |
| *G06F 19/18* | (2011.01) |
| *G06F 19/22* | (2011.01) |
| *G06F 19/24* | (2011.01) |
| *G06F 15/00* | (2006.01) |
| *G11C 17/00* | (2006.01) |

(52) U.S. Cl.
CPC ............. *G06F 19/12* (2013.01); *G06F 19/18* (2013.01); *G06F 19/24* (2013.01); *G06N 5/02* (2013.01); *G06F 19/22* (2013.01)

(58) Field of Classification Search
CPC ............ C12Q 1/6883; C12Q 2600/172; C12Q 2600/118; G06F 19/18; G06F 19/22; G06F 19/24; G06F 19/3437; G06F 19/3443

See application file for complete search history.

(56) References Cited

U.S. PATENT DOCUMENTS

| | | |
|---|---|---|
| 8,008,013 B2 | 8/2011 | Gaffney et al. |
| 8,163,896 B1 | 4/2012 | Bentwich et al. |
| 2004/0161779 A1 | 8/2004 | Gingeras |
| 2012/0059594 A1 | 3/2012 | Hatchwell et al. |
| 2013/0116930 A1 | 5/2013 | Karczewski et al. |
| 2013/0116931 A1 | 5/2013 | Karczewski et al. |

OTHER PUBLICATIONS

Shendure et al. Next-generation DNA sequencing Nature Biotechnology vol. 26, pp. 1135-1145 (2008).*
Fan et al. Noninvasive diagnosis of fetal aneuploidy by shotgun sequencing DNA from maternal blood Proceedings of the National Academy of Sciences USA vol. 16266-16271 (2008).*
Chen et al. -717A>G polymorphism of human C-reactive protein gene associated with coronary heart disease in ethnic Han Chinese: the Beijing atherosclerosis study Journal of Molecular Medicine vol. 83, pp. 72-78 (2005).*
Wheeler et al. The complete genome of an individual by massively parallel DNA sequencing Nature vol. 452, j pp. 872-877 (2008).*
Candore et al. Pharmacogenomics: A Tool to Prevent and Cure Coronary Heart Disease Current Pharmaceutical Design vol. 13 pp. 3726-3734 (2007).*
Dewey et al. Phase Whole-Genome Genetic Risk in a Family Quartet Using a Major Allele Reference Sequence PLoS Genetics vol. 7, article e1002280 (2011).*
Abecasis et al., "Merlin—rapid analysis of dense genetic maps using sparse gene flow trees", Nature Genetics, Jan. 2002, vol. 30, pp. 97-101.
Adzhubei et al., "A method and server for predicting damaging missense mutations", Nat Methods 7, 248-249 (2010).
Ashley et al., "Clinical assessment incorporating a personal genome", Lancet 375, 1525-1535 (2010).
Baudat et al., "PRDM9 is a major determinant of meiotic recombination hotspots in humans and mice", Science 327, 836-840 (2010).
Bentley et al., "Accurate whole human genome sequencing using reversible terminator chemistry", Nature, Articles, Nov. 6, 2008, vol. 456, pp. 53-59.
Bezemer et al., "No association between the common MTHFR 677C->T polymorphism and venous thrombosis: results from the MEGA study", Arch Intern Med 167, 497-501 (2007).
Bodenreider, "The Unified Medical Language System (UMLS): integrating biomedical terminology", Nucleic Acids Research, 2004, vol. 32 Database issue, D267-D270.
Broman et al., "Comprehensive human genetic maps: individual and sex-specific variation in recombination", Am J Hum Genet 63, 861-869 (1998).
Chamary et al., "Hearing silence: non-neutral evolution at synonymous sites in mammals", Nature Reviews Genetics 2006; 7: 98-108.
Chen et al., "The reference human genome demonstrates high risk of type 1 diabetes and other disorders", Pac Symp Biocomput, 231-242 (2011).
De Bakker et al., "A high-resolution HLA and SNP haplotype map for disease association studies in the extended human MHC", Nat Genet 38, 1166-1172 (2006).
Donnelly, "The Probability that Related Individuals Share Some Section of Genome Identical by Descent", Theoretical Population Biology, 1983, vol. 23, pp. 34-63.
Durbin et al., "A map of human genome variation from population-scale sequencing", Nature 467, 1061-1073 (2010).

(Continued)

*Primary Examiner* — John S Brusca
(74) *Attorney, Agent, or Firm* — KPPB LLP

(57) ABSTRACT

In an embodiment of the present invention, three novel human reference genome sequences were developed based on the most common population-specific DNA sequence ("major allele"). Methods were developed for their integration into interpretation pipelines for highthroughput whole genome sequencing.

7 Claims, 71 Drawing Sheets

(56) References Cited

OTHER PUBLICATIONS

Eyre-Walker, "An analysis of codon usage in mammals: selection or mutation bias?", J. Mol. Evol. 1991; 33: 442-449.
Fitch, "Toward Defining the Course of Evolution: Minimum Change for a Specific Tree Topology", Systematic Zoology 20, 406-416 (1971).
Hamosh et al., "Online Mendelian Inheritance in Man (OMIM) a knowledgebase of human genes and genetic disorders", Nucleic Acids Research vol. 30, 52-55, 2002.
Hofacker, "Vienna RNA secondary structure server", Nuc. Acid Res. 2003; V 31 No. 13: 3429-3431.
Hoppe et al., "Marburg I polymorphism of factor VII-activating protease is associated with idiopathic venous thromboembolism", Blood 105, 1549-1551 (2005).
Ikemura, "Codon usage and tRNA content in unicellular and multicellular organisms", Mol. Biol. Evol. 1985 2: 13-34.
Johnson et al., "SNAP: a web-based tool for identification and annotation of proxy SNPs using HapMap", Bioinformatics 24, 2938-2939 (2008).
Kimchi-Sarfaty et al., "A "Silent" Polymorphism in the MDR1 Gene Changes Substrate Specificity", Science 2007; V 315 No. 5811: 525-528.
Kimura, "Evolutionary rate at the molecular level", Nature 217, 624-626 (1968).
Klein et al., "Estimation of the warfarin dose with clinical and pharmacogenetic data", N Engl J Med 360, 753-764 (2009).
Kong et al., "Fine-scale recombination rate differences between sexes, populations and individuals", Nature 467, 1099-1103 (2010).
Kong et al., "Parental origin of sequence variants associated with complex diseases", Nature 462, 868-874 (2009).
Kong et al., "Sequence variants in the RNF212 gene associate with genome-wide recombination rate", Science 319, 1398-1401 (2008).
Koster et al., "Venous thrombosis due to poor anticoagulant response to activated protein C: Leiden Thrombophilia Study", Lancet 342, 1503-1506 (1993).
Kruglyak et al., "Parametric and Nonparametric Linkage Analysis: A Unified Multipoint Approach", Am. J. Hum. Genet., 1996, vol. 58, pp. 1347-1363.
Kujovich, "Factor V Leiden thrombophilia", Genet Med 13, 1-16 (2010).
Kumar et al., "Positional conservation and amino acids shape the correct diagnosis and population frequencies of benign and damaging personal amino acid mutations", Genome Research, 2009, vol. 19, pp. 1562-1569.
Kumar et al., "Predicting the effects of coding non-synonymous variants on protein function using the Sift algorithm", Nature Protocols vol. 4, 1073-1082, 2009.
Li et al., "Fast and accurate short read alignment with Burrows-Wheeler transform", Bioinformatics 25, 1754-1760 (2009).
Macaya et al., "A synonymous mutation in TCOF1 causes Treacher Collins syndrome due to mis-splicing of a constitutive exon", Am J Med Genet A 149A, 1624-1627 (2009).
Marchini et al., "A new multipoint method for genome-wide association studies by imputation of genotypes", Nature Genetics 39, 906-13 (2007).
Margaglione et al., "The methylenetetrahydrofolate reductase TT677 genotype is associated with venous thrombosis independently of the coexistence of the FV Lei den and the prothrombin A20210 mutation", Thromb Haemost 79, 907-911 (1998).
Morgan et al., "Likelihood ratios for genome medicine", Genome Medicine, 2010, vol. 2, No. 30, 5 pgs.
Myers et al., "Drive against hotspot motifs in primates implicates the PRDM9 gene in meiotic recombination", Science 327, 876-879 (2010).
Nachman et al., "Estimate of the Mutation Rate per Nucleotide in Humans", Genetics, Sep. 2000, vol. 156, pp. 297-304.
Nelson et al., "The Population Reference Sample, POPRES: a resource for population, disease, and pharmacological genetics research", Am J Hum Genet 83, 347-358 (2008).

Ng et al., "Accounting for Human Polymorphisms Predicted to Affect Protein Function", Genome Research, 2002, vol. 12, pp. 436-446.
Ng et al., "Predicting the Effects of Amino Acid Substitutions on Protein Function", Annu. Ref. Genomics Hum. Genet., 2006, vol. 7, pp. 61-80.
Ng et al., "Sift: Predicting amino acid changes that affect protein function", Nucleic Acids Res 31, 3812-3814 (2003).
Ormond et al., "Challenges in the clinical application o whole-genome sequencing", Lancet 375, 1749-1751 (2010).
Paigen et al., "The recombinational anatomy of a mouse chromosome", PLoS Genet 4, e1000119 (2008).
Parvanov et al., "Prdm9 controls activation of mammalian recombination hotspots", Science 327, 835 (2010).
Petkov et al., "Crossover interference underlies sex differences in recombination rates", Trends Genet 23, 539-542 (2007).
Price et al., "Principal components analysis corrects fro stratification in genome-wide associate studies", Nature Genetics, Aug. 2006, vol. 38, No. 8, pp. 904-909.
Pruitt et al., "NCBI reference sequences (RefSeq): a curated non-redundant.sequence database of genomes, transcripts and proteins", Nucleic Acids Res 35, D61-65 (2007).
Purcell et al., "Plink: A Tool Set for Whole-Genome Association and Population-Based Linkage Analyses", The American Journal of Human Genetics, Sep. 2007, vol. 81, pp. 559-575.
Ramensky et al., "Human non-synonymous SNPs: server and survey", Nucleic Acids Research, 2002, vol. 30, No. 7, pp. 3894-3900.
Ridker et al., "Interrelation of hyperhomocyst(e)inemia, factor V Lei den, and risk of future venous thromboembolism", Circulation 95, 1777-1782 (1997).
Ridker et al., "Mutation in the gene coding for coagulation factor V and the risk of myocardial infarction, stroke, and venous thrombosis in apparently healthy men", N Engl J Med 332, 912-917 (1995).
Rivas et al., "Secondary structure alone is generally not statistically significant for the detection of noncoding RNAs", Bioinformatics 1999; V 16 No. 7: 583-605.
Roach et al., "Analysis of genetic inheritance in a family quartet by whole-genome sequencing", Science 328, 636-639 (2010).
Roemisch et al., "The frequent Marburg I polymorphism impairs the pro-urokinase activating potency of the factor VII activating protease (FSAP)", Blood Coagulation and Fibrinolysis 13, 433-441 (2002).
Sedding et al., "The G534E polymorphism of the gene encoding the factor VII-activating protease is associated with cardiovascular risk due to increased neointima formation", J Exp Med 203, 2801-2807 (2006).
Smith et al., "Mutations in ATP6N1B, encoding a new kidney vacuolar proton pump 116-kD subunit, cause recessive distal renal tubular acidosis with preserved hearing", Nat Genet 26, 71-75 (2000).
Sunyaev et al., "PSIC: profile extraction from sequence alignments with position-specific counts of independent observations", Protein Engineering, 1999, vol. 12, No. 5, pp. 387-394.
Vasen et al., "New Clinical Criteria for Hereditary Nonplyposis Colorectal Cancer (HNPCC, Lynch Syndrome) Proposed by the International Collaborative Group on HNPCC", Gastroenterology, 1999, vol. 116, pp. 1453-1456.
Watterson, "On the number of segregating sites in genetical models without recombination", Theor Popul Biol 7, 256-276 (1975).
Williams et al., "Rapid haplotype inference for nuclear families", Genome Biology, 2010, vol. 11, 17 pgs.
Yeo et al., "Maximum entropy modeling of short sequence motifs with applications to RNA splicing signals", J Comput Biol. 2004;11(2-3):377-94.
Zhang et al., "Generic Algorithm to Predict the Speed of Translational Elongation: Implications for Protein Biogenesis", PLoS One 2009; 4: e5036. doi: 1 0.1371/joumal.pone.0005036.
Kumar et al., "MEGA3: Integrated software for Molecular Evolutionary Genetics Analysis and sequence alignment", Briefings in Bioinformatics vol. 5, pp. 150-163 (2004).
Coop et al., "High-Resolution Mapping of Crossovers Reveals Extensive Variation in Fine-Scale Recombination Patterns Among Humans", Science, vol. 319, 1395-1398, Mar. 7, 2008.

(56) References Cited

OTHER PUBLICATIONS

"23andMe", Wkipedia, Retrieved from: https://en.wikipedia.org/wiki/23andMe, Last edited: Jun. 14, 2017, Printed: Jun. 19, 2017, 9 pgs.

"A Catalog of Published Genome-Wide Association Studies", Retrieved from: https://web.archive.org/web/20110727063625/http://www.genome.gov/gwastudies/, Jul. 27, 2011, Printed on Jun. 19, 2017, 3 pages.

"A Catalog of Published Genome-Wide Association Studies", Updated on May 12, 2015, Retrieved from: https://www.genome.gov/gwastudies/, Printed on Jun. 19, 2017, 2 pgs.

"Definition of Clinical", Merriam-Webster, Retrieved from: https://www.merriam-webster.com/dictionary/clinical, Printed on Jun. 5, 2017, 4 pgs.

"Google Scholar Citation Explorer", userscripts.org, Last updated Sep. 15, 2011, Retrieved from: http://userscripts-mirror.org/scripts/show/44965, Printed Jun. 15, 2017, 2 pgs.

"HighWire Press", Wkipedia, Retrieved from: https://en.wikipedia.org/wiki/HighWire_Press, Printed on Jun. 15, 2017, Last modified May 31, 2016, 2 pgs.

"Human genome: Genomes by the thousand", Nature, vol. 467, Issue 7319, Oct. 28, 2010, pp. 1026-1027.

"InterMine", Wikipedia, Retrieved from: https://en.wikipedia.org/wiki/InterMine, Last edited: May 15, 2017, Printed Jun. 19, 2017, 3 pgs.

"Pubget", Wikipedia, Retrieved from: https://en.wikipedia.org/wiki/Pubget, Last edited: Feb. 27, 2017, Printed Jun. 19, 2017, 3 pgs.

"SNPedia", Wikipedia, Retrieved from: https://en.wikipedia.org/wiki/SNPedia, Last edited: Sep. 26, 2016, Printed Jun. 19, 2017, 3 pgs.

"The Cancer Genome Atlas", Wikipedia, Retrieved from: https://en.wikipedia.org/wiki/The_Cancer_Genome_Atlas, Last edited: May 1, 2017, Printed Jun. 19, 2017, 11 pgs.

Ashley et al., "Clinical assessment incorporating a personal genome", Lancet, May 1, 2010, vol. 375, Issue 9725, pp. 1525-1535.

Bank, "Regulation of human fetal hemoglobin: new players, new complexities", Blood, vol. 107, Issue 2, Jan. 15, 2006, pp. 435-443, printed Dec. 5, 2016 from https://www.ncbi.nlm.nih.gov/pmc/articles/PMCID1895603/?report=printable.

Barrell et al., "The GOA database in 2009—an integrated Gene Ontology Annotation resource", Nucleic Acids Research, 2009, vol. 37, pp. D396-D403, first published online on Oct. 27, 2008.

Bauer et al., "Update on fetal hemoglobin gene regulation in hemoglobinopathies", Current Opinion in Pediatrics, vol. 23, Issue 1, Feb. 2011, pp. 1-8.

Beisswanger et al., "Gene Regulation Ontology (GRO): Design Principles and Use Cases", Studies in Health Technology and Informatics, Jan. 1, 2008, vol. 136, pp. 9-14.

Bejerano et al., "Ultraconserved Elements in the Human Genome", Science, vol. 304, Issue 5675, May 28, 2004, pp. 1321-1325.

Birney et al., "Identification and analysis of functional elements in 1% of the human genome by the ENCODE pilot project", Nature, vol. 447, Issue, 7146, Jun. 14, 2007, pp. 799-816.

Blankenberg et al., "Galaxy: a web-based genome analysis tool for experimentalists", Current protocols in molecular biology, Jan. 2010, Chapter 19, Unit 19 10 1-21, 33 pages; doi:10.1002/0471142727.mb1910s89.

Boyle et al., "Annotation of functional variation in personal genomes using RegulomeDB", Genome Research, vol. 22, 2012, pp. 1790-1797.

Brinkman et al., "Modeling biomedical experimental processes with OBI", Journal of Biomedical Semantics, 2010, vol. 1, Suppl1:S7, 11 pgs.

Carver et al., "Artemis and ACT: viewing, annotating and comparing sequences stored in a relational database", Bioinformatics, 2008, vol. 24, Issue 23, pp. 2672-2676 ; doi.10.1093/bioinformatics/btn529.

Chen et al., "BCL11A represses HBG transcription in K562 cells", Blood Cells, Molecules, and Diseases, 2009, vol. 42, Issue 2, pp. 144-149.

Chen et al., "Non-synonymous and Synonymous Coding SNPs Show Similar Likelihood and Effect Size of Human Disease Association", PLoS One, vol. 5, Issue 10, Oct. 22, 2010, e13574-1-e13574-6.

Ciavatta et al., "Mouse model of human beta zero thalassemia: targeted deletion of the mouse beta maj-and beta min-globin genes in embryonic stem cells", Proc. Natl. Acad. Sci. USA, vol. 92, No. 20, Sep. 1995, pp. 9259-9263.

Collins et al., "The molecular genetics of human hemoglobin", Prog Nucleic Acid Res Mol Biol, 1984, vol. 31, pp. 315-462.

The Gene Ontology Consortium, "The Gene Ontology in 2010: extensions and refinements", Nucleic Acids Res, vol. 38, 2010, pp. D331-D335; doi:10.1093/nar/gkp1018, Published online Nov. 17, 2009.

The 1000 Genomes Project Consortium, "A map of human genome variation from population-scale sequencing", Nature, vol. 467, Oct. 28, 2010, pp. 1061-1073; doi:10.1038/nature09534.

The International HapMap 3 Consortium, "Integrating common and rare genetic variation in diverse human populations", Nature, vol. 467, Issue 7311, Sep. 2, 2010, pp. 52-58; doi:10.1038/nature09298.

Cookson et al., "Mapping complex disease traits with global gene expression", Nat Rev Genet, vol. 10, No. 3, Mar. 2009, pp. 184-194; doi:10.1038/nrg2537.

Daub et al., "The RNA WikiProject: community annotation of RNA families", RNA, 2008, vol. 14, Issue 12, pp. 2462-2464.

Donlin, "Using the Generic Genome Browser (GBrowse)", John Wiley & Sons, Inc., Current Protocols in Bioinformatics, 2007, Chapter 9, Unit 9.9, 24 pgs.

Ed et al., "Apollo: a community resource for genome annotation editing", Bioinformatics, vol. 25, Issue 14, May 2009, pp. 1836-1837; doi:10.1093/bioinformatics/btp314.

Edgar et al., "Gene Expression Omnibus: NCBI gene expression and hybridization array data repository", Nucleic Acids Res, 2002, vol. 30, Issue 1, pp. 207-210.

Elsik et al., "Community annotation: procedures, protocols, and supporting tools", Genome Research, 2006, vol. 16, Issue 11, pp. 1329-1333.

Euskirchen et al., "Mapping of transcription factor binding regions in mammalian cells by ChIP: comparison of array- and sequencing-based technologies", Genome Research, vol. 17, Issue 6, 2007, pp. 898-909.

Fleming et al., "Molecular mechanisms involved in the regulation of the endothelial nitric oxide synthase", Am J Physiol Regul Integr Comp Physiol, vol. 284, Issue 1, 2003, pp. R1-R12.

Flicek et al., "Ensembl 2011", Nucleic Acids Research, 2011, vol. 39, pp. D800-D806; doi:10.1093/nar/gkq1064, Published online Nov. 2, 2010.

Fransen et al., "Analysis of SNPs with an effect on gene expression identifies UBE2L3 and BCL3 as potential new risk genes for Crohn's disease", Hum Mol Genet, vol. 19, Issue 17, Jul. 2010, pp. 3482-3488; doi:10.1093/hmg/ddq264.

Fujita et al., "The UCSC Genome Browser database: update 2011", Nucleic Acids Research, 2011, vol. 39, pp. D876-D882; doi:10.1093/nar/gkq963, Published online Oct. 18, 2010.

Fullwood et al., "Chromatin interaction analysis using paired-end tag sequencing", John Wley & Sons, Inc., Current Protocols in Molecular Biology, 2010, Chapter 21, Unit 21.15, pp. 1-25.

Goecks et al., "Galaxy: a comprehensive approach for supporting accessible, reproducible, and transparent computational research in the life sciences", Genome Biology, 2010, vol. 11, No. 8, 13 pgs.; http://genomebiology.com/2010/11/8/R86.

Green et al., "Charting a course for genomic medicine from base pairs to bedside", Nature, vol. 470, Feb. 10, 2011, pp. 204-213.

Griffith et al., "ORegAnno: an open-access community-driven resource for regulatory annotation", Nucleic Acids Research, 2008, vol. 36, pp. D107-D113; doi:10.1093/nar/gkm967, Published online Nov. 15, 2007.

Haiqi et al., "Transcriptional regulation of Foxp3 in regulatory T cells", Immunobiology, vol. 216, Issue 6, Jun. 2011, pp. 678-685.

Harrow et al., "GENCODE: producing a reference annotation for ENCODE", Genome biology, 2006, vol. 7, Suppl1, p. S4 1-9. PMCID: 1810553.

(56) References Cited

OTHER PUBLICATIONS

Hayden, "Human genome at ten: Life is complicated", Nature, vol. 464, Issue 7289, Apr. 2010, pp. 664-667, published online on Mar. 31, 2010.
Hernandez-Boussard et al., "The pharmacogenetics and pharmacogenomics knowledge base: accentuating the knowledge", Nucleic Acids Research, 2008, vol. 36, p. D913-D918; doi:10.1093/nar/gkm1009, Published Online Nov. 21, 2007.
Hindorff et al., "Potential etiologic and functional implications of genome-wide association loci for human diseases and traits", Proc Natl Acad Sci USA, Jun. 9, 2009, vol. 106, No. 23, pp. 9362-9367. PMCID: 2687147.
Hirahara et al., "Signal transduction pathways and transcriptional regulation in Th17 cell differentiation", Cytokine Growth Factor Rev, vol. 21, No. 6, Dec. 2010, p. 425-34; doi:10.1016.j.cytogrf.2010.10.006.
Human Genome Variation Society, "Database", Retrieved from: www.hgvs.org/dblist/glsdb.html#H, Last updated Mar. 27, 2017, Printed: Jun. 15, 2017, 62 pages.
Huss et al., "A Gene Wiki for Community Annotation of Gene Function", PLoS Biology, vol. 6, Issue 7, Jul. 2008, e175, pp. 1398-1402. PMCID: 2443188.
John et al., "Human MicroRNA targets", PLoS biology, vol. 2, Issue 11, Nov. 2004, Article e363, pp. 1862-1879.
Karczewski et al., "Cooperative transcription factor associations discovered using regulatory variation", Proceedings of the National Academy of Science of the United States of America, vol. 108, No. 32, Aug. 9, 2011, pp. 13353-13358.
Kasowski et al., "Variation in transcription factor binding among humans", Science, vol. 328, Issue 5975, Apr. 2010, pp. 232-235; doi:10.1126/science.0083621.
Koch et al., "The landscape of histone modifications across 1% of the human genome in five human cell lines", Genome Research, 2007, vol. 17, No. 6, pp. 691-707.
Kozomara et al., "miRBase: integrating microRNA annotation and deep-sequencing data", Nucleic Acids Res, vol. 39, 2011, pp. D152-D157; do:10.1093/nar/gkq1027, Published online Oct. 30, 2010.
Krichevsky et al., "MIR-21: a small multi-faceted RNA", Journal of Cellular and Molecular Medicine, 2009, vol. 13, Issue 1, pp. 39-53.
Kumar et al., "Predicting the effects of coding non-synonymous variants on protein function using the SIFT algorithm", Nature Protocols, 2009, vol. 4, No. 8, p. 1073-1082, Published online Jun. 25, 2009.
Kuntzer et al., "Human variation databases", Database: the journal of biological databases and curation, vol. 2010, Article baq015, 2010, 13 pgs.; doi:10.1093/database/baq015.
Lawson et al., "VectorBase: a data resource for invertebrate vector genomics", Nucleic Acids Res, vol. 37, 2009, pp. D583-D587; doi:10.1093/nar/gkn857, Published online Nov. 21, 2008.
Legeai et al., "AphidBase: a centralized bioinformatic resource for annotation of the pea aphid genome", Insect Mol Biol, vol. 19, Suppl 2, Mar. 2010, pp. 5-12; doi:10.1111/j.1365-2583.2009.00930.x.
Leslie et al., "Non-genomic loss of PTEN function in cancer: not in my genes", Trends in Pharmacological Sciences, Mar. 2011, vol. 32, No. 3, pp. 131-140.
Lewis et al., "Conserved Seed Pairing, Often Flanked by Adenosines, Indicates That Thousands of Human Genes are microRNA Targets", Cell, vol. 120, Issue 1, Jan. 14, 2005, pp. 15-20.
Lin et al., "Transcription factor binding and modified histones in human bidirectional promoters", Genome Research, 200, vol. 17, Issue 6, pp. 818-827. PMCID: 1891341.
Majewski et al., "The study of eQTL variations by RNA-seq: from SNPs to phenotypes", Trends in Genetics, Feb. 2011, vol. 27, No. 2, pp. 72-79.
Mccarthy et al., The CFTR gene and regulation of its expression Pediatric Pulmonology, 2005, vol. 40, Issue 1, pp. 1-8, Published online Apr. 1, 2005.
Metherall et al., "Beta zero thalassemia caused by a base substitution that creates an alternative splice acceptor site in an intron", The EMBO Journal, 1986, vol. 5, No. 10, pp. 2551-2557. PMCID: 1167152.
Moore et al., "Global analysis of disease-related DNA sequence variation in 10 healthy individuals: Implications for whole genome-based clinical diagnostics", Genet Med, vol. 13, Issue 3, Mar. 2011, pp. 210-217; doi.10.1097/GIM.0g013e31820ed321.
Mungall et al., "Evolution of the Sequence Ontology terms and relationships", Journal of Biomedical Informatics, 2011, vol. 44, Issue 1, pp. 87-93.
Mungall et al., "Integrating phenotype ontologies across multiple species", Genome Biology, 2010, vol. 11, Issue 1, Article R2, 16 pgs.; http://genomebioloby.com/2010/11/1/R2.
Natale et al., "The Protein Ontology: a structured representation of protein forms and complexes", Nucleic Acids Res, vol. 39, 2011, pp. D539-D545, Published online Oct. 8, 2010.
Ng et al., "Exome sequencing identifies MLL2 mutations as a cause of Kabuki syndrome", Nature Genetics, vol. 42, No. 9, Sep. 2010, pp. 790-793. PMCID: 2930028. Published online on Aug. 15, 2010.
Ng et al., "Exome sequencing identifies the cause of a mendelian disorder", Nat Genet, vol. 42, No. 1, Jan. 2010, p. 30-35. PMCID: 2847889.
Nicolae et al., "Trait-Associated SNPs are More Likely to be eQTLs: Annotation to Enhance Discovery from GWAS", PLoS Genetics, vol. 6, Issue 4, Apr. 2010, 10 pgs.
Osborne et al., "Annotating the human genome with Disease Ontology", BMC Genomics, vol. 10, Suppl1, Jul. 7, 2009, Article S6, 8 pgs.
Ott et al., "Novel regulatory mechanisms for the CFTR gene", Biochem Soc Trans, 2009, vol. 37, Pt 4, pp. 843-848. PMCID: 2794656.
Parkinson et al., "Array Express—a public repository for microarray gene expression data at the EBI", Nucleic Acids Res, Jan. 1, 2005, vol. 33, pp. D553-555. PMCID: 540010.
Pruitt et al., "The consensus coding sequence (CCDS) project: Identifying a common protein-coding gene set for the human and mouse genomes", Genome Research, 2009, vol. 19, Issue 7, pp. 1316-1323.
Rada-Iglesias et al., "A unique chromatin signature uncovers early developmental enhancers in humans", Nature, vol. 470, Issue 7333, Feb. 10, 2011, pp. 279-283; doi:10.1038/nature09692.
Rada-Iglesias et al., "Butyrate mediates decrease of histone acetylation centered on transcription start sites and down-regulation of associated genes", Genome Research, 2007, vol. 17, Issue 6, pp. 708-719.
Reich et al., "Linkage disequilibrium in the human genome", Nature, vol. 411, May 10, 2001, pp. 199-204.
Robertson et al., "cisRED: a database system for genome-scale computational discovery of regulatory elements", Nucleic Acids Res, Jan. 1, 2006, vol. 34, pp. D68-D73.
Robinson et al., "The Human Phenotype Ontology: A Tool for Annotating and Analyzing Human Hereditary Disease", The American Journal of Human Genetics, vol. 83, Nov. 7, 2008, pp. 610-615.
Saccone et al., "New tools and methods for direct programmatic access to the dbSNP relational database", Nucleic Acids Res, vol. 39, 2011, pp. D901-D907; doi:10.1093/nar/gkq1054, Published online Oct. 29, 2010.
Sargent et al., "The roles of 5'-HS2, 5'-HS3, and the gamma-globin TATA, CACCC, and stage selector elements in suppression of beta-globin expression in early development", J Biol Chem, Apr. 16, 1999, vol. 274, No. 16, pp. 11229-11236.
Sayers et al., "Database resources of the National Center for Biotechnology Information", Nucleic Acids Research, vol. 39, 2011, pp. D38-D51; doi:10.1093/nar/gkq1172, Published online Nov. 20, 2010.
Seal et al., "Genenames.org: the HGNC resources in 2011", Nucleic Acids Research, vol. 39, 2011, pp. D514-519, Published online Oct. 6, 2010.
Searles, "Transcriptional and posttranscriptional regulation of endothelial nitric oxide synthase expression", Am J Physiol Cell Physiol, 2006, vol. 291, No. 5, pp. C803-C816, First Published May 31, 2005.

(56) References Cited

OTHER PUBLICATIONS

Sherry et al., "dbSNP: the NCBI database of genetic variation", Nucleic Acids Research, Jan. 1, 2001, vol. 29, No. 1, pp. 308-311. PMCID: 29783.
Shimada et al., "VarySysDB: a human genetic polymorphism database based on all H-InvDB transcripts", Nucleic Acids Res, 2009, vol. 37, pp. D810-D815; doi:10.1093/nar/gkn798, Published online Oct. 25, 2008.
Smith et al., "The OBO Foundry: coordinated evolution of ontologies to support biomedical data integration", Nature Biotechnology, Nov. 2007, vol. 25, No. 11, pp. 1251-1255; doi:10.1038/nbt1346.
Stehr et al., "PDBWki: added value through community annotation of the Protein Data Bank", Database: the journal of biological databases and curation, vol. 2010, Article baq009, 2010, 8 pgs.
Teo et al., "Singapore Genome Variation Project: a haplotype map of three Southeast Asian populations", Genome Research, 2009, vol. 19, No. 11, pp. 2154-2162.
Thorisson et al., "HGVbaseG2P: a central genetic association database", Nucleic Acids Research, 2009, vol. 37, pp. D797-D802, Published Online Oct. 23, 2008.
The UNIPROT Consortium, "The Universal Protein Resource (UniProt) in 2010", Nucleic Acids Res, 2010, vol. 38, pp. D142-D148, Published Online Oct. 20, 2009.
Vaquerizas et al., "A census of human transcription factors: function, expression and evolution", Nature Reviews, Apr. 2009, vol. 10, No. 4, pp. 252-263.
Visel et al., "ChIP-seq accurately predicts tissue-specific activity of enhancers", Nature, Feb. 12, 2009, vol. 457, No. 7231, pp. 854-858.
Visel et al., "Genomic views of distant-acting enhancers", Nature, Sep. 2009, vol. 461, No. 7261, pp. 199-205; doi:10.1038/nature08451, Manuscript available in PMC Aug. 17, 2010.
Wang et al., "ANNOVAR: functional annotation of genetic variants from high-throughput sequencing data", Nucleic Acids Res, 2010, vol. 38, No. 16, Article e164, 7 pgs., Published online Jul. 3, 2010.
Whetzel et al., "BioPortal: enhanced functionality via new Web services from the National Center for Biomedical Ontology to access and use ontologies in software applications", Nucleic Acids Research, 2011, vol. 39, pp. W541-W545; doi:10.1093/nar/gkr469; Published Online Jun. 14, 2011.
Witkos et al., "Practical Aspects of microRNA Target Prediction", Curr Mol Med, 2011, vol. 11, No. 2, pp. 93-109.
Woolfe et al., "CONDOR: a database resource of developmentally associated conserved non-coding elements", BMC Dev Biol, Aug. 30, 2007, vol. 7, No. 100, 11 pgs.
Woolfe et al., "Highly conserved non-coding sequences are associated with vertebrate development", PLoS biology, Jan. 2005, vol. 3, Issue 1, Article e7, pp. 0116-0130.
Worthey et al., "Making a definitive diagnosis: Successful clinical application of whole exome sequencing in a child with intractable inflammatory bowel disease", Genetics in Medicine, Mar. 2011, vol. 13, No. 3, pp. 255-262.
Wu et al., "BioGPS: an extensible and customizable portal for querying and organizing gene annotation resources", Genome Biology, Nov. 17, 2009, vol. 10, Issue 11, Article R130, pp. R130.1-R130.8.
Xu et al., "A comprehensive ChiP-chip analysis of E2F1, E2F4, and E2F6 in normal and tumor cells reveals interchangeable roles of E2F family members", Genome Research, 2007, vol. 17, No. 11, pp. 1550-1561.

Yang et al., "A mouse model for beta 0-thalassemia", Proc Natl Acad Sci USA, vol. 92, Dec. 1995, pp. 11608-11612.
Zheng et al., "Regulatory Variation Within and Between Species", Annual Review of Genomics and Human Genetics, vol. 12, Sep. 2011, pp. 327-346, First Published as a Review in Advance on Jul. 1, 2011.
"The Cancer Genome Atlas", National Cancer Institute Home Page, Aug. 11, 2011, retrieved from https://web.archive.org/web/20110811091933/www.cancergenome.nih.gov/ on May 14, 2018, 2 pages.
The International HapMap Consortium "A second generation human haplotype map of over 3.1 million SNPs", Nature, vol. 449, Oct. 18, 2007, pp. 851-861.
Arnett et al., "Preventing and Controlling Hypertension in the Era of Genomic Innovation and Environmental Transformation", Journal of American Medical Association, vol. 308, No. 17, Nov. 7, 2012, pp. 1745-1746.
Awad et al., "Mechanisms of disease: molecular genetics of arrhythmogenic right ventricular dysplasia/cardiomyopathy", Nat Clin Pract Cardiovasc Med, vol. 5, No. 5, May 2008, pp. 258-267.
Ball et al., "A public resource facilitating clinical use of genomes", Proc. Natl. Acad. Sci. U.S.A., vol. 109, No. 30, Jul. 24, 2012, pp. 11920-11927.
Blake et al., "The Mouse Genome Database", Nucleic Acids Research, vol. 37, 2009, Published online Nov. 3, 2008, pp. D712-719.
Bryne et al., "Jaspar, the open access database of transcription factor-binding profiles: new content and tools in the 2008 update", Nucleic Acids Research, vol. 36, 2008, Published online Nov. 15, 2007, pp. D102-106.
Cantor et al., "Prioritizing GWAS Results: A Review of Statistical Methods and Recommendations for Their Application", The American Journal of Human Genetics, vol. 86, Jan. 8, 2010, pp. 6-22.
Dunham et al., "An integrated encyclopedia of DNA elements in the human genome", Nature, vol. 489, Sep. 6, 2012, pp. 57-74.
Eeles et al., "Identification of seven new prostate cancer susceptibility loci through a genome-wide association study", Nat. Genet., vol. 41, No. 10, Oct. 2009, pp. 1116-1121.
Gibson, Greg, "Rare and common variants: twenty arguments", Nature Reviews Genetics, vol. 13, Feb. 2012, published Jan. 18, 2012, 135-145.
Gonzaga-Jauregui et al., "Human Genome Sequencing in Health and Disease", Annu. Rev. Med., vol. 63, 2012, pp. 35-61.
Han et al., "TCRA, P2RY11, and CPT1 B/CHKB associations in Chinese narcolepsy", Sleep Medicine, vol. 13, No. 3, Mar. 2012, pp. 269-272.
Kent et al., "The human genome browser at UCSC", Genome Research, vol. 12, 2002, pp. 996-1006.
Lupski et al., "Whole-Genome Sequencing in a Patient with Charcot-Marie-Tooth Neuropathy", N. Engl. J. Med, Apr. 1, 2010, Published online Mar. 10, 2010, vol. 362, No. 13, pp. 1181-1191.
Manning et al., "A genome-wide approach accounting for body mass index identifies genetic variants influencing fasting glycemic traits and insulin resistance", Nat. Genet., vol. 44, No. 6, 2012, pp. 659-669.
Teslovich et al., "Biological, Clinical and Population Relevance of 95 Loci for Blood Lipids", Nature, vol. 466, No. 7307, Aug. 5, 2010, pp. 707-713.
Veltman et al., "De novo mutations in human genetic disease", Nature Reviews Genetics, vol. 13, Aug. 2012, pp. 565-575.

* cited by examiner

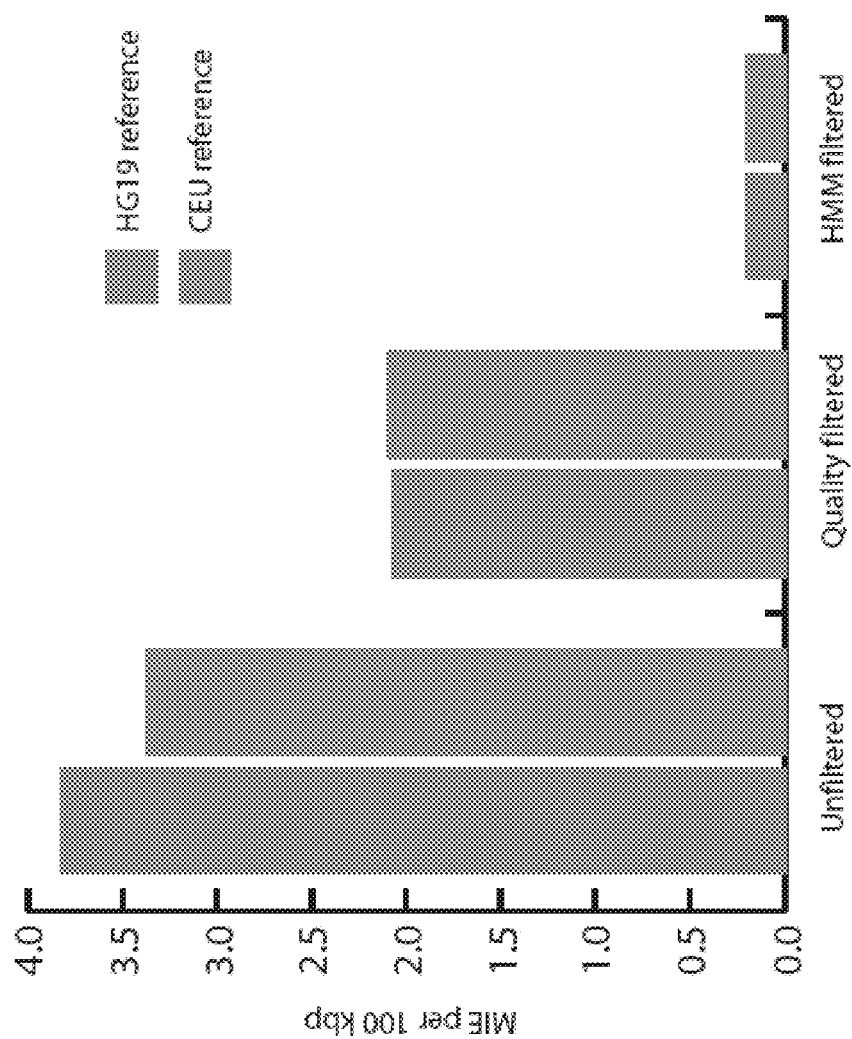

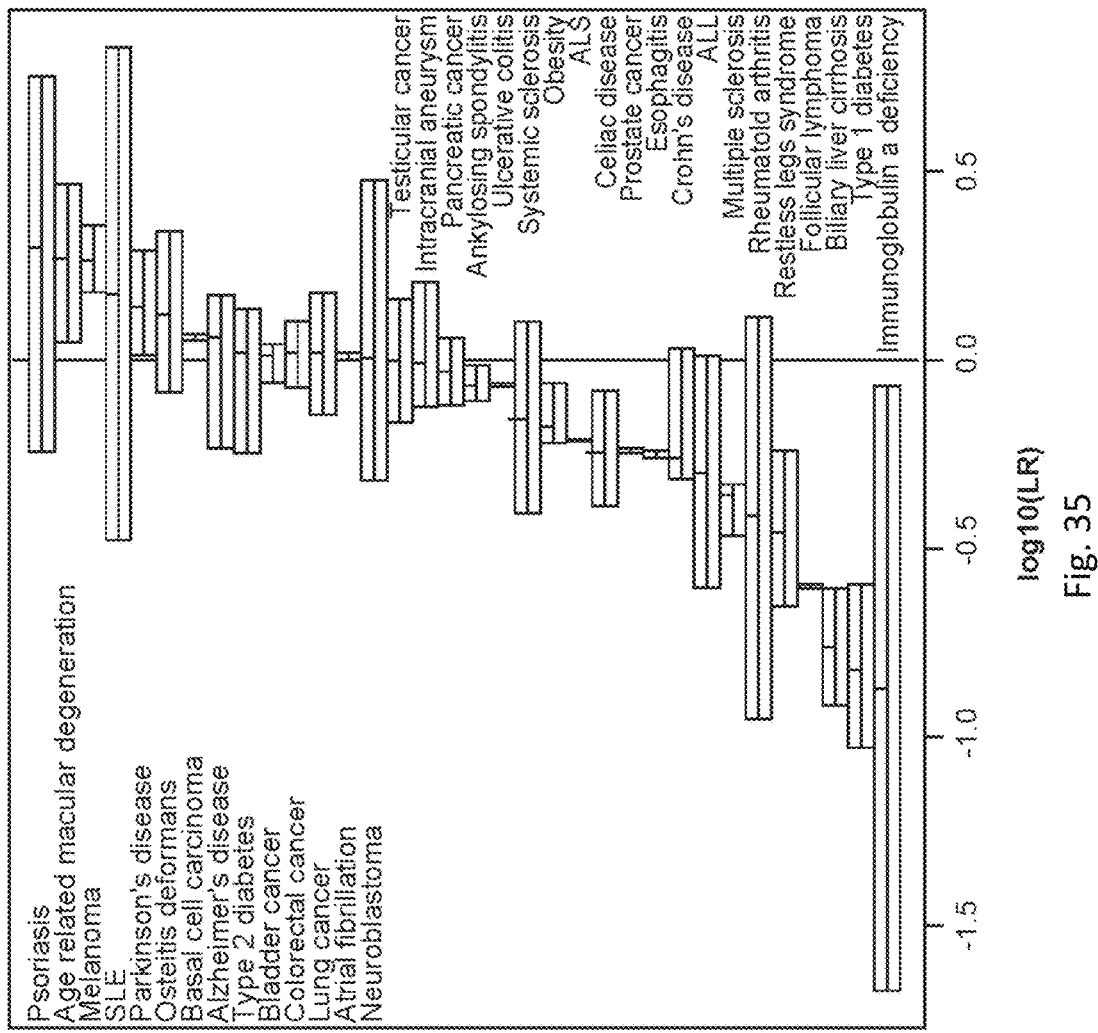

Table 1. Putative loss of function variants across the family quartet.

| Variant type | All variants | | All rare/novel | | Rare/novel and OMIM-disease associated gene | |
|---|---|---|---|---|---|---|
| | HG19 reference (n = 4302405) | CEU reference (n = 5733239) | HG19 reference (n = 351555) | CEU reference (n = 354874) | HG19 reference | CEU reference |
| Coding-missense | 9468 | 7382 | 1276 | 1276 | 203 | 203 |
| Coding-nonsense | 52 | 50 | 13 | 13 | 1 | 1 |
| Coding-synonym | 11663 | 9928 | 1061 | 1059 | 186 | 186 |
| Intronic | 1303341 | 1128283 | 116276 | 115397 | 19544 | 19766 |
| Splice-5' | 156 | 147 | 16 | 16 | 0 | 0 |
| Splice-3' | 88 | 86 | 9 | 9 | 1 | 1 |
| UTR-5 | 40142 | 37794 | 3637 | 3619 | 510 | 516 |
| UTR-3 | 61626 | 59396 | 5869 | 5853 | 846 | 857 |
| miRNA target | 0 | 0 | 0 | 0 | 0 | 0 |
| Pri-miRNA | 2 | 2 | 1 | 1 | 0 | 0 |
| Mature miRNA | 0 | 0 | 0 | 0 | 0 | 0 |
| Coding indels | 1519 | 1478 | 422 | 412 | 73 | 71 |
| Coding frameshift indels | 440 | 418 | 273 | 253 | 29 | 27 |

Abbreviations: CEU reference, variant calls against CEU major allele reference; HG19 reference, variant calls against NCBI reference sequence 37.1; miRNA, micro RNA; Pri-miRNA, primary microRNA transcript; OMIM, Online Mendelian Inheritance in Man database; UTR, un-translated region.

Fig. 36

Table 2. Rare variants with known clinical associations

| Chromosome | Gene | rsid | Affected family members | Disease | Inheritance | Onset-earliest | Onset-median | Severity | Actionability | Lifetime risk | Variant pathogenicity |
|---|---|---|---|---|---|---|---|---|---|---|---|
| 12 | VWF | rs61750615 |  | Von Willebrand disease | Incomplete dominant | 1 | 1 | 5 | 5 | variable | 7 |
| 10 | HABP2 | rs7080536 | 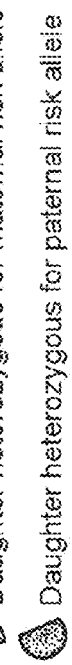 | Carotid stenosis, thrombophilia | AD | 4 | 4 | 1 | 5 | variable | 7 |
| 19 | SLC7A9 | rs79389353 |  | Cysteinuria - kidney stones | AR | 1 | 1 | 3 | 5 | 7 | 7 |
| 1 | F5 | rs6025 |  | Thrombophilia | Incomplete dominant | 4 | 4 | 4 | 5 | 2 | 7 |
| 1 | MTHFR | rs1801133 | 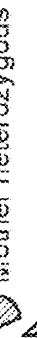 | Hyperhomocysteinemia | AR | 1 | 1 | 1 | 6 | 2 | 7 |

Key:
- Daughter heterozygous for maternal risk allele
- Daughter heterozygous for paternal risk allele
- Son heterozygous for maternal risk allele
- Son heterozygous for paternal risk allele
- Mother heterozygous
- Father heterozygous Abbreviations: AD, autosomal dominant; AR, autosomal recessive. Variants were scored according to disease phenotype features and variant pathogenicity as outlined in Supplementary Table 1.

Fig. 37

Table 3. Drug metabolizing enzyme variants

| Drug Metabolizing Enzyme | Drug Metabolizing | Father Genotype | Father Phenotype | Mother Genotype | Mother Phenotype | Sister Genotype | Sister Phenotype | Brother Genotype | Brother Phenotype |
|---|---|---|---|---|---|---|---|---|---|
| CYP2C9 | warfarin, NSAIDS (naproxen, ibuprofen, celecoxib, etc.), sulfonylureas (glimepiride, glipizide, etc.) fluvastatin | *1/*1 | normal metabolizer | *1/*1 | normal metabolizer | *1/*1 | normal metabolizer | *1/*1 | normal metabolizer |
| CYP2C19 | clopidogrel, proton pump inhibitors (omeprazole, pantoprazole, etc.), citalopram | *17/*2 | ultra metabolizer | *17/*17 | ultra metabolizer | *17/*17 | ultra metabolizer | *17/*2 | ultra metabolizer |
| CYP2D6 | codeine, metoprolol, tamoxifen, fluoxetine | *1/*4 | intermediate metabolizer | *1/*1 | normal metabolizer | *1/*4 | intermediate metabolizer | *1/*4 | intermediate metabolizer |

*CYP2C9 genotypes checked and ruled out: *2, *3, *5, *8, *9 *10, *11, *12, *16; defaults to *1
*CYP2C19 genotypes based on single defining SNPs for the *17 and *2 alleles; all other alleles ruled out by default
*CYP2D6 genotypes checked: *2, *4, *5, *10, *15, and because of overlap of snps, can also rule out *8, *11, *12, *14, *17, *19, *20, *29, *31, *35, *40, *41, *69; to determine *1 status

Fig. 38

Table 4. Genetic pharmacological response predicitons

| SNP Location | Drug(s) | Drug(s) More Likely to Work | Drug(s) Less Likely to Work | Drug(s) More Likely to Cause side Effect | Drug(s) Less Likely to Cause side Effect | Drug Dose(s) Above Average | Drug Dose(s) Below Average | Drug Dose(s) Average | No PGx Action/ Phenotype Unknown | Confidence Level |
|---|---|---|---|---|---|---|---|---|---|---|
| rs9934438 | warfarin |  |  |  |  |  |  | ■◆●○ |  | High |
| rs1954787 | citalopram | ■◆● | ■ |  |  |  |  |  |  | High |
| rs7767746 | cyclosporine |  |  |  |  |  | ■◆●○ |  |  | High |
| rs1800460 | thiopurines |  |  |  |  |  |  |  |  | High |
| rs2108522 | warfarin |  |  |  |  |  | ■◆●○ |  |  | Medium |
| rs4680 | morphine |  |  |  |  | ■◆●○ |  |  |  | Medium |
| rs5443 | statins | ■◆ | ■○ |  |  |  |  |  |  | Medium |
| rs4253778 | beta blocking agents | ○ | ■◆■ |  |  |  |  |  |  | Medium |
| rs622342 | metformin | ○■ | ■○ |  |  |  |  |  |  | Medium |
| rs7569963 | citalopram |  |  | ■ | ■◆●○ |  |  |  | ●○ | Medium |
| rs8012552 | ACE inhibitors |  |  |  | ■◆●○ |  |  |  |  | Low |
| rs11209716 | ACE inhibitors |  |  |  |  |  |  |  | ○ | Low |

Key: Father, Mother, Brother, Sister ■◆●○

Fig. 39

Table 5: Prioritization schema for rare and novel single nucleotide polymorphisms

| Scale | Definition | Level keyed | 1 | 2 | 3 | 4 | 5 | 6 | 7 | 8 | 9 | 10 |
|---|---|---|---|---|---|---|---|---|---|---|---|---|
| Onset - earliest | earliest possible age of onset | phenotype | infantile | 1-10yo | 11-20yo | 21-50yo | >51yo | | | | | |
| Onset - median | median age of onset | phenotype | infantile | 1-10yo | 11-20yo | 21-50yo | >51yo | | | | | |
| Severity | worst case, untreated, accounting for mortality and morbidity | phenotype | rarely affects quality of life | rarely affects quality of life | mild impact on quality or quantity of life | mild impact on quality or quantity of life | moderate impact on quality or quantity of life | moderate impact on quality or quantity of life | severely limits either quality or quantity of life | severely limits either quality or quantity of life | severely limits both quality and quantity of life | severely limits both quality and quantity of life |
| Actionability | based on best treatment of any manifestation (primarily because that's what data is historically available) | phenotype | medical or surgical prevention available | medical or surgical prevention available | medical or surgical cure available | medical or surgical cure available | | Condition is not curable but effective protection from most decrements in quality and quantity of life | treatments are available, but they only minimally affect decrements in quality or quantity of life | treatments are available, but they only minimally affect decrements in quality or quantity of life | only palliative intervention available | only palliative intervention available |
| Lifetime risk | | phenotype | no clinical impact, children may be at risk | <20% | 21-30% | 31-40% | 41-50% | 51-60% | 61-70% | 71-80% | 81-90% | 91-100% |
| Pathogenicity | likelihood variant causes disease | variant | known benign, strong evidence | some evidence suggesting benign | Novel, predicted benign | Novel, predicted to be damaging by 1 program | Novel, predicted to be damaging by 2 or more programs | reported in one case | reported in multiple cases | segregates with disease in own family | segregates with disease in 2 families | experimental evidence confirms pathogenicity |

Fig. 46

| Chrom | Pos. | Ref. | rsid | son pat. allele | son mat. allele | daught. pat. allele | daught. mat. allele | fath. allele 1 | fath. allele 2 | moth. allele 1 | moth. allele 2 | maf | pp2 prediction | sift prediction | gene symbol | omim diseases | mammal rate | mam. Time span | variant ancest. count |
|---|---|---|---|---|---|---|---|---|---|---|---|---|---|---|---|---|---|---|---|
| 19 | 577782 | C | novel | T | G | G | G | G | T | G | G | 0.003 | possibly damaging | damaging | bsg | [blood group, ok], 111380 (3) | 3.67 | 0.49 | 2 |
| 1 | 982722 | A | novel | G | A | G | A | G | A | A | A | 0.004 | benign | damaging | agrn | myasthenia, limb-girdle, familial, 254300 (3) | 0 | 0.66 | 4 |
| 11 | 1775352 | C | novel | C | T | C | C | G | C | T | C | 0.003 | benign | tolerated | ctsd | ceroid lipofuscinosis, neuronal (batten type 2), 10, 610127 (3) | 1.11 | 0.66 | 5 |
| 16 | 2168570 | G | novel | G | G | C | C | C | C | G | G | 0.007 | probably damaging | damaging | pkd1 | polycystic kidney disease, adult type 1 | 0.84 | 0.86 | 0 |
| 4 | 3148570 | G | rs36892943 | A | G | A | C | A | A | G | G | 0.042 | benign | tolerated | htt | huntington disease, 143100 (3) | 0.48 | 0.76 | 5 |
| 4 | 3494996 | C | rs16844484 | C | C | C | C | C | C | G | T | 0.036 | probably damaging | tolerated | dok7 | fetal akinesia deformation sequence, 208150 (3) | 1.7 | 0.64 | 1 |
| 17 | 3563930 | G | novel | A | G | A | C | A | A | G | C | novel | possibly damaging | tolerated | ctns | cystinosis, atypical nephropathic (3) | 0.61 | 0.7 | 1 |
| 1 | 6528137 | G | novel | G | G | G | C | T | G | G | G | novel | probably damaging | tolerated | plekhg5 | spinal muscular atrophy, distal, autosomal recessive, 4, 611067 (3) | 1.69 | 0.86 | 2 |
| 9 | 6663446 | C | novel | C | C | C | C | T | A | G | G | novel | benign | tolerated | gldc | glycine encephalopathy, 605899 (3) | 1.79 | 0.81 | 12 |
| 12 | 7046178 | G | novel | G | G | G | G | T | G | T | C | 0.006 | unknown | tolerated | atm1 | dentatorubro-pallidoluysian atrophy, 125370 (3) | 0.6 | 0.61 | 3 |
| 19 | 11233856 | C | rs45603991 | G | C | C | C | C | A | C | C | 0.013 | benign | damaging | ldlr | hypercholesterolemia, familial, 143890 (3) | 0.66 | 0.55 | 0 |
| 16 | 14028031 | C | rs1799802 | T | T | T | C | T | A | C | C | 0.018 | probably damaging | damaging | ercc4 | xfe progeroid syndrome, 610966 (3) | 0 | 0.98 | 0 |
| 1 | 16373000 | A | rs6650119 | A | A | A | A | A | A | A | G | 0.012 | possibly damaging | damaging | clcnkb | bartter syndrome, type 3, 607364 (3) | 1 | 0.72 | 1 |
| 1 | 19189446 | C | rs61767693 | G | T | G | C | G | C | T | C | 0.033 | probably damaging | damaging | aldh4a1 | hyperprolinemia, type ii, 239510 (3) | 0 | 0.77 | 0 |
| 11 | 22301090 | C | novel | C | G | C | C | C | A | C | C | novel | probably damaging | damaging | sno6 | gnathodiaphyseal dysplasia, 166260 (3) | 0 | 0.92 | 0 |
| 16 | 23400267 | C | novel | T | G | G | C | T | A | C | C | novel | probably damaging | damaging | cog7 | congenital disorder of glycosylation, type lle, 608779 (3) | 0 | 0.83 | 0 |
| 16 | 23408440 | G | rs16940094 | G | G | G | A | G | G | A | A | 0.33 | possibly damaging | tolerated | cog7 | congenital disorder of glycosylation, type lle, 608779 (3) | 0.78 | 0.92 | 2 |

FIG. 47A

| | | | | | | | | | | | | | | |
|---|---|---|---|---|---|---|---|---|---|---|---|---|---|---|
| 16 | 28466943 | t | rs77896156 | T | C | T | C | T | C | T | 0.026 | probably damaging | tolerated | cln3 | ceroid-lipofuscinosis, neuronal-3, juvenile, 204200 (3) | 0 | 0.82 | 1 |
| 15 | 28617429 | g | novel | G | C | G | C | G | G | A | novel | probably damaging | damaging | herc2 | [skin/hair/eye pigmentation 1, blond/brown hair], 227220 (3) | 0 | 0.9 | 1 |
| 18 | 29102187 | c | novel | C | C | C | T | C | C | T | novel | probably damaging | damaging | dsg2 | arrhythmogenic right ventricular dysplasia, familial, 10, 610193 (3) | 0 | 0.93 | 6 |
| 2 | 31600672 | g | rs45464839 | G | G | G | A | G | G | A | 0.007 | possibly damaging | damaging | xdh | xanthinuria, type 1, 603707 (3) | 0 | 0.94 | 1 |
| 22 | 36745146 | g | novel | G | G | G | A | G | G | A | novel | possibly damaging | damaging | myh9 | deafness, autosomal dominant 17, 603622 (3) | 0 | 0.87 | 1 |
| 8 | 38163346 | c | novel | A | G | A | T | G | T | G | novel | probably damaging | tolerated | whsc1l1 | leukemia, acute myeloid, 601626 (3) | 0 | 0.91 | 0 |
| 22 | 40787509 | t | rs8142464 | T | T | C | C | T | T | C | 0.001 | probably damaging | damaging | adsl | adenylosuccinase deficiency, 103050 (3) | 0.37 | 0.96 | 0 |
| 19 | 40803043 | c | rs117336941 | C | C | C | C | C | C | T | 0.017 | benign | tolerated | prx | charcot-marie-tooth disease, type 4f, 145900 (3) | 3.18 | 0.68 | 8 |
| 3 | 41862331 | c | rs617335313 | T | G | G | G | T | G | G | 0.026 | probably damaging | damaging | ank1 | spherocytosis, type 1, 182900 (3) | 0 | 0.86 | 0 |
| 19 | 46274624 | g | novel | G | G | G | A | G | G | A | novel | possibly damaging | damaging | dmpk | myotonic dystrophy, 160900 (3) | 0.55 | 0.68 | 1 |
| 1 | 46742242 | a | rs26363192 | A | G | A | A | G | A | A | 0.027 | benign | damaging | rad54l | adenocarcinoma, colonic, somatic (3) | 0.39 | 0.93 | 0 |
| 12 | 51083364 | c | rs74761916 | T | C | C | C | T | C | C | 0.033 | possibly damaging | damaging | dip2b | mental retardation, fra12a type, 136630 (3) | 0 | 0.75 | 0 |
| 14 | 51372238 | t | rs34313873 | T | T | T | A | G | T | C | 0.068 | possibly damaging | damaging | pygl | glycogen storage disease vi (3) | 0 | 0.96 | 0 |
| 5 | 52337963 | g | novel | A | G | A | G | A | G | C | novel | probably damaging | damaging | itga2 | glycoprotein ia deficiency (1)(7) | 0 | 0.91 | 0 |
| 12 | 52710721 | g | rs2862464 | G | G | G | C | G | G | C | 0.022 | possibly damaging | damaging | krt83 | monilethrix, 158000 (3) | 2.21 | 0.85 | 0 |
| 4 | 55127446 | g | rs36035373 | G | G | G | G | G | G | G | 0.007 | possibly damaging | damaging | pdgfra | gastrointestinal stromal tumor, somatic, 606764 (3) | 0 | 0.96 | 0 |
| 20 | 56137130 | g | novel | G | G | G | G | T | G | G | novel | probably damaging | damaging | pck1 | hypoglycemia due to pck1 deficiency (1) | 0 | 0.9 | 0 |

FIG. 47B

| | | | | | | | | | | | | | | | | | |
|---|---|---|---|---|---|---|---|---|---|---|---|---|---|---|---|---|---|
| 17 | 56346106 | t | rs2759 | T | T | T | T | C | T | T | C | 0.018 | benign | tolerated | mpo | myeloperoxidase deficiency, 254600 (3) | 0 | 1 |
| 17 | 61659041 | g | rs611740288 | G | G | G | A | G | G | G | G | novel | benign | tolerated | ace | renal tubular dysgenesis, 267430 (3) | 0 | 0 |
| 2 | 71762413 | g | rs611740288 | G | G | G | A | G | G | G | G | 0.025 | probably damaging | damaging | dysf | miyoshi myopathy, 254130 (3) | 0 | 0 |
| 45 | 73617404 | g | novel | A | G | G | A | C | G | G | G | novel | unknown | damaging | hcn4 | brugada syndrome 8, 613123 (3) | 0 | 0 |
| 2 | 73679955 | c | rs28730854 | C | C | A | A | C | C | C | C | 0.017 | possibly damaging | damaging | alms1 | alstrom syndrome, 203800 (3) | 0.51 | 0 |
| 14 | 75513463 | a | rs17782839 | A | A | A | A | A | C | G | G | 0.013 | benign | tolerated | mlh3 | colon cancer, hereditary nonpolyposis, type 7 (3) | 1.71 | 23 |
| 14 | 75515668 | t | rs227856861 | G | G | T | T | A | T | G | A | 0.013 | possibly damaging | tolerated | mlh3 | colon cancer, hereditary nonpolyposis, type 7 (3) | 0.38 | 1 |
| 12 | 76740149 | g | rs35676114 | G | G | G | G | G | G | G | G | 0.033 | benign | tolerated | ttbs10 | bardet-biedel syndrome 10, 209900 (3) | 1.74 | 9 |
| 17 | 78186067 | c | novel | C | C | C | C | C | C | C | C | novel | probably damaging | tolerated | sgsh | sanfilippo syndrome, type a, 252900 (3) | 0 | 0 |
| 15 | 89363840 | c | novel | C | T | A | A | T | T | T | T | novel | probably damaging | tolerated | polg | alpers syndrome, 203700 (3) | 0.46 | 1 |
| 15 | 91326099 | g | rs11862361 | G | C | C | C | C | C | G | G | 0.043 | possibly damaging | damaging | blm | bloom syndrome, 210900 | 0 | 0 |
| 15 | 91354621 | g | rs7167216 | G | G | G | A | C | G | C | G | 0.025 | benign | tolerated | blm | bloom syndrome, 210900 (3) | 2.96 | 11 |
| 14 | 94844847 | c | rs28929474 | A | C | C | T | C | C | T | T | 0.017 | probably damaging | damaging | serpina1 | emphysema due to aat deficiency, 613490 (3) | 0.92 | 1 |
| 9 | 95411644 | g | novel | G | G | C | A | A | G | G | G | novel | probably damaging | damaging | rad54b | colon adenocarcinoma (3) | 0.39 | 0 |
| 12 | 102168764 | g | rs76989468 | G | G | C | A | C | C | A | G | 0.025 | possibly damaging | damaging | gnptab | mucolipidosis ii alpha/beta, 252500 (3) | 0.37 | 0 |
| 11 | 103026166 | c | novel | C | C | C | A | A | A | A | A | novel | possibly damaging | damaging | dync2h1 | asphyxiating thoracic dystrophy 3, 613091 (3) | 2.02 | 1 |
| 9 | 104125056 | a | rs61756096 | A | C | C | A | C | C | A | C | 0.009 | benign | tolerated | baat | hypercholanemia, familial, 607748 (3) | 6.1 | 9 |
| 11 | 108143456 | c | rs1800057 | C | C | C | C | C | C | C | C | 0.025 | probably damaging | damaging | atm | ataxia-telangiectasia, 208900 (3) | 0 | 0 |
| 11 | 111635566 | c | rs1805076 | C | C | G | T | T | G | C | G | 0.006 | benign | tolerated | ppp2r1b | lung cancer, 211980 (3) | 0.8 | 0 |

FIG. 47C

| | | | | | | | | | | | | | | | |
|---|---|---|---|---|---|---|---|---|---|---|---|---|---|---|---|
| 9 | 116852162 | g | novel | G | C | G | G | G | C | C | C | novel | probably damaging | tolerated | ikbkap | dysautonomia, familial, 223900 (3) | 0 | 0.95 | 0 |
| 5 | 112178796 | g | rs2229995 | G | C | C | A | G | G | C | A | 0.032 | benign | tolerated | apc | adenoma, periampullary (3) | 0 | 0.95 | 4 |
| 10 | 112572456 | g | rs14176535 | C | C | C | C | G | G | C | C | 0.002 | benign | tolerated | rbm20 | cardiomyopathy, dilated, 1dd, 613172 (3) | 2.53 | 0.98 | 31 |
| 11 | 123604870 | g | novel | G | A | G | A | A | A | A | G | novel | benign | tolerated | scn3b | brugada syndrome 7, 613120 (3) | 1.9 | 0.95 | 6 |
| 11 | 467474447 | g | rs62623459 | G | G | G | G | A | G | G | G | 0.001 | benign | tolerated | f2 | hypoprothrombinemia (3 | 4.76 | 0.83 | 16 |
| 8 | 144836494 | g | rs6869407 | T | C | T | C | C | T | T | C | 0.043 | probably damaging | damaging | plec1 | epidermolysis bullosa simplex with pyloric atresia, 612138 (3) | 1.32 | 0.82 | 7 |
| 2 | 167168386 | g | novel | G | C | C | G | G | G | A | A | novel | possibly damaging | damaging | scn9a | erythermalgia, primary, 133020 (3) | 0.76 | 0.96 | 0 |
| 2 | 170103472 | g | rs114842875 | G | A | G | C | G | G | A | A | 0.017 | probably damaging | damaging | hrp2 | donnai-barrow syndrome, 222448 (3) | 0.77 | 0.94 | 1 |
| 3 | 187447761 | c | rs61752081 | C | C | C | A | C | C | C | C | 0.042 | benign | tolerated | bclk | lymphoma, b-cell (2) | 1.25 | 0.87 | 0 |
| 1 | 197237571 | g | novel | T | T | T | T | T | T | C | T | novel | possibly damaging | damaging | crb1 | leber congenital amaurosis 8 (3) | 0 | 0.87 | 0 |
| 2 | 203420712 | g | rs2226645 | G | A | G | G | A | G | A | G | 0.022 | benign | tolerated | bmpr2 | pulmonary hypertension, familial primary, 178600 (3) | 0.38 | 0.96 | 3 |
| 2 | 226163463 | c | rs57611801 | A | C | A | C | C | A | A | C | 0.035 | unknown | tolerated | col4a3 | alport syndrome, autosomal recessive, 203780 (3) | 1.61 | 0.9 | 4 |
| 2 | 233639653 | c | rs2269912 | A | C | A | C | C | A | C | C | 0.017 | possibly damaging | tolerated | gigyf2 | parkinson disease 11, 607688 (3) | 0.88 | 0.82 | 0 |

*FIG. 47D*

Table 7: Compound heterozygous and homozygous variants in Mendelian disease associated genes

| Chromosome | Position | Reference | rsid | son paternal allele | son maternal allele | daughter paternal allele | daughter maternal allele | father allele 1 | father allele 2 | mother allele 1 | mother allele 2 | MAF | PP2 prediction | SIFT prediction | Gene symbol | OMIM diseases | mammal rate | mammal timespan | Variant ancestral count |
|---|---|---|---|---|---|---|---|---|---|---|---|---|---|---|---|---|---|---|---|
| 8 | 144995494 | C | rs6558407 | T | T | C | C | T | C | T | C | 0.04 | probably damaging | DAMAGING | PLEC1 | Epidermolysis bullosa simplex with pyloric atresia, 612138 (3) | 1.32 | 0.82 | |
| 12 | 52710721 | G | rs2852464 | G | G | C | C | G | C | G | C | 0.02 | possibly damaging | DAMAGING | KRT83 | Monilethrix, 158000 (3) | 2.21 | 0.65 | |
| 8 | 17928811 | C | rs1071645 | C | C | T | T | T | T | C | T | 0.03 | benign | TOLERATED | ASAH1 | Farber lipogranulomatosis (3) | 3.06 | 0.82 | 1 |
| 15 | 91326099 | C | rs11852361 | C | C | T | C | C | C | T | C | 0.04 | possibly damaging | DAMAGING | BLM | Bloom syndrome, 210900 (3) | 0.00 | 0.88 | |
| 15 | 91354521 | G | rs718216 | G | A | A | G | A | G | A | G | 0.03 | benign | TOLERATED | BLM | Bloom syndrome, 210900 (3) | 2.96 | 0.97 | 1 |
| 2 | 74489318 | G | rs55651232 | G | A | A | G | G | G | A | G | 0.03 | possibly damaging | TOLERATED | SLC4A5 | Renal tubular acidosis, proximal, with ocular abnormalities, 604278 (3) | 0.00 | 0.71 | |
| 2 | 74463058 | C | rs36081793 | T | C | C | C | T | C | T | C | 0.03 | possibly damaging | TOLERATED | SLC4A5 | Renal tubular acidosis, proximal, with ocular abnormalities, 604278 (3) | 0.38 | 0.96 | |
| 14 | 75615666 | T | rs28736981 | G | G | A | T | G | A | G | T | 0.01 | possibly damaging | TOLERATED | MLH3 | Colon cancer, hereditary nonpolyposis, type 7 (3) | 0.38 | 0.94 | |
| 14 | 75513463 | A | rs1776289 | A | G | A | A | A | A | A | A | 0.01 | benign | TOLERATED | MLH3 | Colon cancer, hereditary nonpolyposis, type 7 (3) | 1.71 | 0.85 | 2 |
| 16 | 23409440 | A | rs16940094 | G | G | G | G | G | G | G | A | 0.03 | possibly damaging | TOLERATED | COG7 | Congenital disorder of glycosylation, type IIe, 608779 (3) | 0.78 | 0.92 | |
| 16 | 23400257 | C | novel | T | C | T | C | C | C | C | C | novel | probably damaging | DAMAGING | COG7 | Congenital disorder of glycosylation, type IIe, 608779 (3) | 0.00 | 0.83 | |

Fig. 48

Table 8: example pharmacogenomics annotation

| Proton Pump Inhibitors (such as Prilosec) | |
|---|---|
| Father | Probable typical response to proton pump inhibitors. |
| Details: | CYP2C19*2/CYP2C19*17, one poor metabolizer allele and one ultra-rapid metabolizer allele. Response to proton pump inhibitors with this combination in alleles is not well-studied. The poor metabolizer allele associates with increased response to treatment for some indications, while the ultra-rapid metabolizer allele associates with decreased response. |
| Mother | May not respond well to commonly prescribed dosages due to ultrarapid clearance of these drugs. |
| Details: | CYP2C19*17 homozygous, ultra-rapid metabolizer. Is associated with increased proton pump inhibitor clearance and decreased efficacy. |
| Sister | May not respond well to commonly prescribed dosages due to ultrarapid clearance of these drugs. |
| Details: | CYP2C19*17 homozygous, ultra-rapid metabolizer. Is associated with increased proton pump inhibitor clearance and decreased efficacy. |
| Brother | Probable typical response to proton pump inhibitors. |
| Details: | CYP2C19*2/CYP2C19*17, one poor metabolizer allele and one ultra-rapid metabolizer allele. Response to proton pump inhibitors with this combination in alleles is not well-studied. The poor metabolizer allele associates with increased response to treatment for some indications, while the ultra-rapid metabolizer allele associates with decreased response. |

Fig. 49

Table 9. Variants associated with drug efficacy

Key: Father, Mother, Brother, Sister = ■ ○ ● ○

| Gene Symbol | SNP Location | Drug(s) | Drug(s) More Likely to Work | Drug(s) Less Likely to Work | No PGx Action/ Phenotype Unknown | Confidence Level |
|---|---|---|---|---|---|---|
| GRIK4 | rs1954787 | citalopram | ■ ○ ● ○ | ■ | | High |
| LTA, TNF | rs1800629 | adalimumab, etanercept, infliximab | ■ ○ ● ○ | | | Medium |
| VDR | rs1544410 | alendronate, bisphosphonates, calcium, clodronate, etidronic acid, raloxifene | | ■ ○ ● ○ | | Medium |
| ABCB1 | rs2032583 | antidepressants | ■ | | | Medium |
| FKBP5 | rs3800373 | antidepressants | | ■ ○ ● ○ | | Medium |
| FKBP5 | rs1360780 | antidepressants | | ■ ○ ● ○ | | Medium |
| HTR2A | rs7997012 | antidepressants, citalopram | ■ ○ | ■ ○ | | Medium |
| SERPINE1 | rs2227631 | antidepressants, citalopram, fluoxetine | ○ | ■ ○ ● | | Medium |
| NOS3 | rs2070744 | antihypertensives and diuretics in combination | ■ ○ ● ○ | | | Medium |
| PPARA | rs4253778 | beta blocking agents | ○ | ■ ○ ● | | Medium |
| IL1B | rs16944 | bisphosphonates, clodronate, etidronic acid, risedronate, tiludronate | ■ ● | ○ ○ | | Medium |
| COMT | rs1655599 | bupropion | ■ ○ ● ○ | | | Medium |
| HTR3B | rs1800497 | bupropion | ■ ○ ● ○ | | | Medium |
| GSTA1 | rs3957357 | cisplatin, cyclophosphamide | | ○ ○ | ■ | Medium |
| ERCC2, KLC3 | rs13181 | cisplatin, fluorouracil, leucovorin, platinum compounds | | ■ ○ ● ○ | | Medium |
| SOD2 | rs4880 | cyclophosphamide | ○ | ■ ○ ● | | Medium |
| NOS3 | rs1799983 | cyclophosphamide, doxorubicin, fluorouracil, methotrexate | ■ ○ ● ○ | | | Medium |
| CYP1B1 | rs1056836 | docetaxel, paclitaxel, taxanes | ■ ○ | ○ ● | | Medium |
| ABCB1 | rs1045642 | efavirenz, nelfinavir | ■ | ■ ○ ○ | | Medium |
| CACNG2 | rs2284017 | lithium | ■ ○ ● ○ | | | Medium |

FIG. 50A

| | | | | |
|---|---|---|---|---|
| SLC22A1 | rs622342 | metformin | | Medium |
| ABCG2 | rs13120400 | methotrexate | ■○● | Medium |
| FPGS, ZYG11BL | rs1544105 | methotrexate | ■ | Medium |
| SLC19A1 | rs1051266 | methotrexate | ○○ | Medium |
| ABCG2 | rs17731538 | methotrexate | ■○●○ | Medium |
| MTHFR | rs1801131 | methotrexate | ■○● | Medium |
| ADM, SBF2 | rs11042725 | paroxetine | ■○● | Medium |
| intergenic | rs16895 | platinum compounds | | Medium |
| KIF6 | rs20455 | pravastatin | ■○●○ | Medium |
| FCGR3A | rs396991 | rituximab | ○■ | Medium |
| ABCG2 | rs2231142 | rosuvastatin | ■○● | Medium |
| ABCG2 | rs2231142 | rosuvastatin | ■○● | Medium |
| CRHR2 | rs7793837 | salbutamol, selective beta-2-adrenoreceptor agonists | ■○● | Medium |
| ACE | rs4343 | sildenafil | | ■ ○○ | Medium |
| MBOAT5, GNB3, USP5 | rs5443 | sildenafil | ■ | ○○ | Medium |
| MBOAT5, GNB3, USP5 | rs5443 | statins | ■○ | ○ | Medium |
| TCF7L2 | rs12255372 | sulfonamides, urea derivatives | ■ | ■○● | Medium |
| MBOAT5, GNB3, USP5 | rs5443 | sumatriptan | ■○ | ■○ | Medium |
| intergenic | rs10811661 | troglitazone | ■○● | | Medium |
| HTR1A | rs6295 | antidepressants | ■○● | ○ | Medium |
| ABCB1 | rs2235015 | antidepressants | ■ | ■○● | Low |
| TPH2 | rs10879346 | antidepressants, mirtazapine, venlafaxine | ■○ | ○■ | Low |
| LDLR | rs688 | atenolol | ■ | | Low |
| FDPS, PKLR | rs2297480 | bisphosphonates | ■○● | ○■ | Low |
| GCND1 | rs9344 | cetuximab | | ○ | Low |
| ERCC2, KLC3 | rs13181 | cisplatin | | ■○● | Low |
| VDR | rs731236 | clodronate | | ■○● | Low |
| DTNBP1 | rs742105 | clozapine | | | Low |

*FIG. 50B*

| | | | | | | |
|---|---|---|---|---|---|---|
| ABCB1 | rs2032582 | cyclosporine | ■○ | ■ | | Low |
| CDA | rs532545 | cytarabine | ■■ | ○○ | | Low |
| CHST3 | rs4148943 | docetaxel, thalidomide | ○■ | ■○ | | Low |
| CHST3 | rs4148945 | docetaxel, thalidomide | ○■ | ■○ | | Low |
| CHST3 | rs4148947 | docetaxel, thalidomide | ○■ | ■○ | | Low |
| CHST3 | rs4148950 | docetaxel, thalidomide | ■○■○ | | | Low |
| CHST3 | rs1871450 | docetaxel, thalidomide | ■○■○ | | | Low |
| CHST3 | rs730720 | docetaxel, thalidomide | ○■ | ■○ | | Low |
| CHST3 | rs12418 | docetaxel, thalidomide | ■○■○ | | | Low |
| PPARD | rs2016520 | docetaxel, thalidomide | ■○■○ | | | Low |
| PPARD | rs2016520 | docetaxel, thalidomide | ■○■○ | | | Low |
| PPARD | rs6922548 | docetaxel, thalidomide | | ■■ | ○○ | Low |
| SULT1C4 | rs1402467 | docetaxel, thalidomide | | ■■ | ○○ | Low |
| PPARD | rs1883322 | docetaxel, thalidomide | ■■ | | ○○ | Low |
| PPARD | rs7769719 | docetaxel, thalidomide | ■■ | | ○○ | Low |
| PTGS2 | rs20417 | ibuprofen | ○○ | ■■ | | Low |
| APOB | rs1367117 | irbesartan | ■○■ | ○ | | Low |
| PKD1L3, DHODH | rs3213422 | leflunomide | | ○ | ■■○ | Low |
| CYP19A1 | rs4646 | letrozole | ■○○ | ■ | | Low |
| TLR3 | rs3775291 | measles vaccines | ■○■○ | | | Low |
| TLR3 | rs3775291 | measles vaccines | ■○■○ | | | Low |
| ARID5B | rs10821936 | methotrexate | ■○ | ○■ | | Low |
| ATIC | rs2372536 | methotrexate | | ■○■○ | | Low |
| TPH2 | rs1487278 | mirtazapine, venlafaxine | ■○ | ○■ | | Low |
| ABCC1 | rs119774 | montelukast | | ■○■○ | | Low |
| ALOX5 | rs2115819 | montelukast | ■ | ○■○ | | Low |
| LTC4S | rs730012 | montelukast | ■○■○ | | | Low |
| RMST | rs2660845 | montelukast | ○ | ■■○ | | Low |
| SLCO2B1 | rs12422149 | montelukast | | ■○■ | ○ | Low |
| ABCC1 | rs119774 | montelukast | | ■○■○ | | Low |
| IMPDH1 | rs2278294 | mycophenolate mofetil | ○■ | ■○ | | Low |
| IMPDH1 | rs2278293 | mycophenolate mofetil | ○■○ | ■ | | Low |
| DRD3 | rs6280 | olanzapine | | ■○■○ | | Low |
| HTR2A | rs6313 | olanzapine, risperidone | ○ | ■○■ | | Low |

*FIG. 50C*

| Gene | RS | Drug | | | Level |
|---|---|---|---|---|---|
| ABCB1 | rs2032582 | paclitaxel | | ○○ | Low |
| SLCO1B1 | rs4149015 | pravastatin | ■ | ○○ | Low |
| ABCB1 | rs1045642 | prednisone, tacrolimus | ■○■ | | Low |
| SLCO1B1 | rs2306283 | repaglinide | ■ | ○○ | Low |
| ABCB1 | rs1128503 | risperidone | ■○■ | ○ | Low |
| COMT | rs165599 | risperidone | | ■○■○ | Low |
| DRD3 | rs6280 | risperidone | | ■○■○ | Low |
| GRM3 | rs724226 | risperidone | ○○ | | Low |
| HTR2A | rs6311 | risperidone | ■■○ | | ■■ | Low |
| RGS4 | rs951439 | risperidone | ○ | ■■○ | Low |
| RGS4 | rs2842030 | risperidone | ○○ | ■■○ | Low |
| PTGS2 | rs20417 | rofecoxib | ■■ | ○○ | Low |
| ADRB2 | rs1042713 | salmeterol | ■○■○ | | Low |
| ACE | rs4343 | spironolactone | ○■○ | ■ | Low |
| GSTP1 | rs6138150 | tumor necrosis factor alpha (TNF-alpha) inhibitors | | ■○■○ | Low |
| GBP6 | rs928655 | tumor necrosis factor alpha (TNF-alpha) inhibitors | ■○ | ○ | Low |
| MOBKL2B | rs868856 | tumor necrosis factor alpha (TNF-alpha) inhibitors | | ■○■○ | Low |
| PON1 | rs854555 | tumor necrosis factor alpha (TNF-alpha) inhibitors | | ■○■○ | Low |
| PPP1R9A | rs854547 | tumor necrosis factor alpha (TNF-alpha) inhibitors | | ■○■○ | Low |
| PPP1R9A, PON1 | rs854548 | tumor necrosis factor alpha (TNF-alpha) inhibitors | | ■○■○ | Low |
| intergenic | rs963332 | tumor necrosis factor alpha (TNF-alpha) inhibitors | ■ | ■○■○ | Low |
| intergenic | rs3849942 | tumor necrosis factor alpha (TNF-alpha) inhibitors | ○ | ■○■○ | Low |
| intergenic | rs6026945 | tumor necrosis factor alpha (TNF-alpha) inhibitors | ■○■ | | Low |
| intergenic | rs6071980 | tumor necrosis factor alpha (TNF-alpha) inhibitors | ○ | ■○■ | Low |
| intergenic | rs437943 | tumor necrosis factor alpha (TNF-alpha) inhibitors | | ■○■○ | Low |

| | | | | | |
|---|---|---|---|---|---|
| C9orf72 | rs774359 | tumor necrosis factor alpha (TNF-alpha) inhibitors | ■○※○ | | Low |
| MOBKL2B | rs2814707 | tumor necrosis factor alpha (TNF-alpha) inhibitors | ■○※○ | | Low |
| C9orf72 | rs774359 | tumor necrosis factor alpha (TNF-alpha) inhibitors | ■○※○ | | Low |
| LTA, TNF | rs1800629 | adalimumab, etanercept, infliximab | ■○※○ | | Medium |
| VDR | rs1544410 | alendronate, bisphosphonates, calcium, clodronate, etidronic acid, raloxifene | | ■○※○ | Medium |
| ABCB1 | rs2032583 | antidepressants | ※ | ■○※○ | Medium |
| FKBP5 | rs3800373 | antidepressants | ■○※○ | ■○※○ | Medium |
| FKBP5 | rs1360780 | antidepressants | ■○※○ | ■○※○ | Medium |
| HTR2A | rs7997012 | antidepressants, citalopram | ■○ | ※○ | Medium |
| SERPINE1 | rs2227631 | antidepressants, citalopram, fluoxetine | ○ | ■○※ | Medium |
| NOS3 | rs2070744 | antihypertensives and diuretics in combination | ■○※○ | | Medium |
| PPARA | rs4253778 | beta blocking agents | ○ | ■○※ | Medium |
| IL1B | rs16944 | bisphosphonates, clodronate, etidronic acid, risedronate, tiludronate | ■ | ○○ | Medium |
| ARVCF, COMT | rs165599 | bupropion | ■○※○ | | Medium |
| HTR3B | rs1800497 | bupropion | ■○※○ | | Medium |
| GSTA1 | rs3957357 | cisplatin, cyclophosphamide | | ○○ ※ | Medium |
| ERCC2, KLC3 | rs13181 | cisplatin, fluorouracil, leucovorin, platinum compounds | | ■○※○ | Medium |
| SOD2 | rs4880 | cyclophosphamide | ○ | ■○※ | Medium |
| NOS3 | rs1799983 | cyclophosphamide, doxorubicin, fluorouracil, methotrexate | ■○※○ | | Medium |
| CYP1B1 | rs1056836 | docetaxel, paclitaxel, taxanes | ■○ | ○※ | Medium |
| ABCB1 | rs1045642 | efavirenz, nelfinavir | ※ | ■○※ | Medium |
| CACNG2 | rs2284017 | lithium | ■○※○ | | Medium |
| SLC22A1 | rs622342 | metformin | ○※ | ○※ | Medium |
| ABCG2 | rs13120400 | methotrexate | ■○※○ | ○ | Medium |
| FPGS, ZYG11BL | rs1544105 | methotrexate | ■ | ○ | Medium |

| | | | | | |
|---|---|---|---|---|---|
| SLC19A1 | rs1051266 | methotrexate | | ■◎▩○ | Medium |
| ABCG2 | rs17731538 | methotrexate | ■◎▩○ | | Medium |
| MTHFR | rs1801131 | methotrexate | ■◎▩○ | | Medium |
| ADM, SBF2 | rs11042725 | paroxetine | ■◎▩○ | | Medium |
| intergenic | rs1695 | platinum compounds | | ■◎▩○ | Medium |
| KIF6 | rs20455 | pravastatin | ■◎▩○ | | Medium |
| FCGR3A | rs396991 | rituximab | ▩◎ | ◎▩ | Medium |
| ABCG2 | rs2231142 | rosuvastatin | | ■◎▩○ | Medium |
| ABCG2 | rs2231142 | rosuvastatin | | ■◎▩○ | Medium |
| CRHR2 | rs7793837 | salbutamol, selective beta-2-adrenoreceptor agonists | | ■◎▩○ | Medium |
| ACE | rs4343 | sildenafil | | ■▩▩ | ○○ | Medium |
| MBOAT5, GNB3, USP5 | rs5443 | sildenafil | | ■▩▩ | ○○ | Medium |
| MBOAT5, GNB3, USP5 | rs5443 | statins | ■○ | ▩○ | Medium |
| TCF7L2 | rs12255372 | sulfonamides, urea derivatives | ▩ | ■◎○ | Medium |
| MBOAT5, GNB3, USP5 | rs5443 | sumatriptan | ■○ | ▩○ | Medium |
| intergenic | rs10811661 | troglitazone | ■◎▩○ | | Medium |

*FIG. 50F*

Table 10. Variants associated with adverse drug response

Key: Father, Mother, Brother, Sister = ■ ○ ● ○

| Gene Symbol | SNP Location | Drug(s) | Drug(s) More Likely to Cause Side Effect | Drug(s) Less Likely to Cause Side Effect | No PGx Action/ Phenotype Unknown | Confidence Level |
|---|---|---|---|---|---|---|
| TPMT | rs1800460 | purine analogues | | ■○●○ | | High |
| HTR3B | rs1800497 | antipsychotics | ■○●○ | | | Medium |
| HTR2C | rs1414334 | antipsychotics, clozapine, risperidone | ■○ | ○● | | Medium |
| ARVCF, COMT | rs9332377 | cisplatin | | ■○●○ | | Medium |
| COMT | rs4646316 | cisplatin | ■○● | ○ | | Medium |
| ARVCF, COMT | rs9332377 | cisplatin | | ■○●○ | | Medium |
| NHLRC1, TPMT | rs1142345 | cisplatin | | ■○ | ●○ | Medium |
| TPMT | rs1800460 | cisplatin | | ■○ | ●○ | Medium |
| XRCC1 | rs25487 | cisplatin, cyclophosphamide | ■ | ○● | | Medium |
| FAM119A, CREB1 | rs7569963 | citalopram | ■ | ■ | ○● | Medium |
| ABCC1 | rs45511401 | doxorubicin | ■○● | ○ | | Medium |
| ABCC2 | rs17222723 | doxorubicin | ■● | ○○ | | Medium |
| ABCC2 | rs8187710 | doxorubicin | ■● | ○○ | | Medium |
| CYBA | rs4673 | doxorubicin | ○ | ■○●○ | | Medium |
| NCF4 | rs1883112 | doxorubicin | | ■○●○ | | Medium |
| RAC2 | rs13058338 | doxorubicin | ○○ | ■● | | Medium |
| ABCB1 | rs1045642 | efavirenz, nelfinavir | ■ | ■○●○ | | Medium |
| CYP1A2 | rs762551 | leflunomide | | ■○●○ | | Medium |
| PICK1, ENTHD1 | rs2076369 | methamphetamine | | ○ | ■●○ | Medium |
| ADORA2A | rs2298383 | methotrexate | ■○■ | ○ | | Medium |
| ADORA2A | rs3761422 | methotrexate | ■○●○ | | | Medium |
| ADORA2A | rs2267076 | methotrexate | ■○●○ | | | Medium |
| ADORA2A | rs2236624 | methotrexate | ■○●○ | | | Medium |

FIG. 51A

| Gene | rsID | Drug | | | | | Level |
|---|---|---|---|---|---|---|---|
| ADORA2A, CYTSA | rs5760410 | methotrexate | ■○■○ | | | | Medium |
| SLC19A1 | rs1051266 | methotrexate | | ■○■○ | | | Medium |
| ABCC1 | rs246240 | methotrexate | ■○■○ | | | | Medium |
| REN, ETNK2 | rs2368564 | muraglitazar | ■ | ■○○ | | | Medium |
| EDN1 | rs5370 | muraglitazar | | ■○■○ | | | Medium |
| CHRNA4 | rs2236196 | nicotine | ○○ | | ■■ | | Medium |
| CHRNA4 | rs1044396 | nicotine | ○○ | | ■■ | | Medium |
| intergenic | rs10115393 | nicotine | | ■○■○ | | | Medium |
| MTHFR | rs1801131 | nitrous oxide | | ■○■○ | | | Medium |
| HTR2C | rs518147 | olanzapine | ○■ | ■ | ○ | | Medium |
| EPHX1 | rs1051740 | phenytoin | ○○ | | | ■■ | Medium |
| EPHX1 | rs1051740 | phenytoin | ○○ | | | ■■ | Medium |
| EPHX1 | rs2234922 | phenytoin | | | ○○ | ■■ | Medium |
| intergenic | rs1695 | platinum compounds | ■○■○ | | | | Medium |
| SLCO1B1 | rs4149056 | pravastatin | | ■○■○ | | | Medium |
| APOA4, APOA1, APOC3 | rs5128 | ritonavir | ■■○ | ○ | | | Medium |
| APOA4, APOC3 | rs2854117 | ritonavir | ■■○ | ○ | | | Medium |
| APOA4, APOC3 | rs2854116 | ritonavir | ■■○ | ○ | | | Medium |
| BDKRB2 | rs8012552 | ace inhibitors, plain | | ■○■○ | | | Low |
| PTGER3 | rs11209716 | ace inhibitors, plain | | ■■○ | ○ | | Low |
| CYP2C8 | rs10509681 | amodiaquine | | ■○■○ | | | Low |
| CYP2C8 | rs10509681 | amodiaquine | | ■○■○ | | | Low |
| DSCR9, CBR3 | rs1056892 | anthracyclines and related substances | ■○■○ | | | | Low |
| HTR3B | rs1800497 | antipsychotics | | ■○■○ | | | Low |
| HTR3B | rs2276307 | atorvastatin, pravastatin, simvastatin | ■■○ | ○ | | | Low |
| HTR7 | rs1935349 | atorvastatin, pravastatin, simvastatin | ■■ | ○○ | | | Low |
| NHLRC1, TPMT | rs1142345 | azathioprine, mercaptopurine, purine analogues | | ■○■○ | | | Low |

FIG. 51B

| Gene | RS ID | Drug | | | | Level |
|---|---|---|---|---|---|---|
| HSPA1A, C6orf21, HSPA1L | rs2227956 | carbamazepine | ○■ | ■○ | | Low |
| LTA, TNF | rs1800629 | carbamazepine | | ■○■○ | | Low |
| LRP2 | rs2075252 | cisplatin | ○ | ■○■○ | | Low |
| SLC22A2 | rs316019 | cisplatin | ■○■○ | | | Low |
| XPC, TMEM43 | rs2228001 | cisplatin | ■○■○ | | | Low |
| ERCC1 | rs11615 | cisplatin, cyclophosphamide | ■○■ | ○ | | Low |
| ERCC1, CD3EAP, PPP1R13L | rs3212986 | cisplatin, cyclophosphamide | ■○■ | ○ | | Low |
| DRD2 | rs6277 | clozapine, olanzapine | ■○■ | ○ | | Low |
| HTR3B | rs1800497 | clozapine, olanzapine | | ■○■○ | | Low |
| CYP3A4 | rs2740574 | cyclophosphamide | | ■○■○ | | Low |
| CDA | rs532545 | cytarabine | ○○ | ■■ | | Low |
| ABCC6 | rs2238472 | docetaxel, thalidomide | ■○■○ | | | Low |
| CHST3 | rs4148945 | docetaxel, thalidomide | ○■ | ■○ | | Low |
| CHST3 | rs4148950 | docetaxel, thalidomide | ■○■○ | | | Low |
| CYP4B1 | rs4646487 | docetaxel, thalidomide | ○○ | ■■ | | Low |
| NAT2 | rs1799931 | docetaxel, thalidomide | ■○■○ | | | Low |
| RPL13, SPG7 | rs12960 | docetaxel, thalidomide | ○■■○ | ■ | | Low |
| SLC10A2 | rs2301159 | docetaxel, thalidomide | ○○ | ■■ | | Low |
| SPG7 | rs2292954 | docetaxel, thalidomide | ○■○ | ■ | | Low |
| SLC22A16 | rs714368 | doxorubicin, doxorubicinol | | ■○■○ | | Low |
| CELF4 | rs4799915 | iloperidone | ■○ | ○■ | | Low |
| CERKL | rs993648 | iloperidone | ■ | ○■○ | | Low |
| NRG3 | rs4933824 | iloperidone | ■○■○ | | | Low |
| NUBPL | rs7142881 | iloperidone | ○■○ | ■ | | Low |
| ABCB1 | rs1045642 | nortriptyline | ■ | ■○○ | | Low |
| HTR2A | rs7997012 | olanzapine | | ■○■○ | | Low |
| CYP2C8 | rs1113129 | paclitaxel | ■○ | | ○■ | Low |
| CYP3A5 | rs776746 | paclitaxel | | ■○■○ | | Low |
| CYP2C8 | rs1934951 | pamidronate, zoledronate | ■○■○ | | | Low |
| AGTR1 | rs5182 | perindopril | ■○■○ | | | Low |
| DRD3 | rs167771 | risperidone | | ■○■○ | | Low |

*FIG. 51C*

| LEP | rs7799039 | risperidone | ■○■◇ | | Low |
| HTR3B | rs1800497 | risperidone | | ■○■◇ | Low |
| DRD2 | rs1799978 | risperidone | | ■○■◇ | Low |
| ESR2 | rs4986938 | tamoxifen | | ○○ | ■○ | Low |
| ESR1 | rs9340799 | tamoxifen | | ○○ | ■○○ | Low |
| NOS1AP | rs10918594 | verapamil | ■ | | ■○○ | Low |
| NOS1AP | rs10494366 | verapamil | ■ | ○ | ■○ | Low |

*FIG. 51D*

Table 11: variants associated with drug dosing

Key: Father, Mother, Brother, Sister = ●◐○◌

| Gene Symbol | SNP Location | Drug(s) | Drug Dose(s) Easy to Predict | Drug Dose(s) Difficult to Predict | Drug Dose(s) Above Average | Drug Dose(s) Below Average | No PGx Action / Phenotype Unknown | Confidence Level |
|---|---|---|---|---|---|---|---|---|
| CYP3A5 | rs776746 | cyclosporine | | | | ●◐○ | | High |
| CYP4F2 | rs2108622 | acenocoumarol, warfarin | | | | ●◐○ | | Medium |
| CYP4F2 | rs2108622 | acenocoumarol, warfarin | | | | ●◐○ | | Medium |
| SCN1A | rs2612718 | carbamazepine | | | ○◌ | | ● | Medium |
| NALCN | rs7992226 | methotrexate | | ●◐○ | | | | Medium |
| COMT | rs4680 | morphine | | | ●◐○ | | | Medium |
| OPRM1 | rs1799971 | morphine | | | | ●◐○ | | Medium |
| SCN1A | rs3812718 | phenytoin | | | ●◐○ | | ● | Medium |
| EPHX1 | rs2292566 | warfarin | | | ●◐○ | ●◐○ | | Medium |
| STK4 | rs10971454 | warfarin | | | | ●◐○ | | Medium |
| VKORC1 | rs9050894 | warfarin | | | | | | Medium |
| CYP3A4 | rs2740574 | docetaxel | ●◐○ | | | | | Low |
| ABCB1 | rs1045642 | fexofenadine | ●◐○ | | ● | | | Low |
| CYP3A4 | rs2740574 | indinavir | ●◐○ | | | | | Low |
| SLCO1B1 | rs4149056 | methotrexate | ●◐○ | | | | | Low |
| SLCO1B1 | rs2306283 | pravastatin | | ●◐○ | | | | Low |
| CYP3A4 | rs2740574 | tacrolimus | ●◐○ | | | | | Low |
| ABCC4 | rs1751034 | tenofovir | | ●◐○ | | | | Low |
| GSTP1 | rs1138272 | thiotepa | | ●◐○ | | | | Low |

Fig. 52

SYSTEMS AND METHODS FOR INTERPRETING A HUMAN GENOME USING A SYNTHETIC REFERENCE SEQUENCE

CROSS-REFERENCE TO RELATED APPLICATIONS

This application claims priority to U.S. Provisional Application No. 61/474,749 filed Apr. 13, 2011, and to U.S. Provisional Application No. 61/502,236 filed Jun. 28, 2011. The disclosures of U.S. Provisional Application No. 61/474,749 and U.S. Provisional Application No. 61/502,236 are hereby incorporated by reference in their entirety for all purposes.

STATEMENT OF GOVERNMENT SPONSORED SUPPORT

This invention was made with Government support under contracts HL083914 and OD004613 awarded by the National Institutes of Health. The Government has certain rights in this invention.

FIELD OF THE INVENTION

The present invention generally relates to the field of genomics. More particularly, the present invention relates to the field of whole genome sequencing and analysis.

BACKGROUND OF THE INVENTION

Whole genome sequencing of related individuals provides opportunities for investigation of human recombination and compound heterozygous loci contributing to Mendelian disease traits as well as error control. The recent publication of low-coverage sequencing data from large numbers of unrelated individuals offers a broad catalog of genetic variation in three major population groups that is complementary to deep sequencing of related individuals. (Durbin, R. M., et al. A map of human genome variation from population-scale sequencing. Nature 467, 1061-1073 (2010). This and all other cited references are incorporated herein by reference in their entirety.) Recently, investigators used a family-sequencing approach to fine map recombination sites, and combined broad population genetic variation data with phased family variant data to identify putative compound heterozygous loci associated with the autosomal recessive Miller syndrome. (Roach, J. C., et al. Analysis of genetic inheritance in a family quartet by whole-genome sequencing. Science 328, 636-639 (2010).)

One of the challenges to the interpretation of massively parallel whole genome sequence data is the assembly and variant calling of sequence reads against the human reference genome. Although de novo assembly of genome sequences from raw sequence reads represents an alternative approach, computational limitations and the large amount of mapping information encoded in relatively invariant genomic regions make this an unattractive option presently. The NCBI human reference genome in current use (Pruitt, K. D., Tatusova, T. & Maglott, D. R. NCBI reference sequences (RefSeq): a curated non-redundant sequence database of genomes, transcripts and proteins. Nucleic Acids Res 35, D61-65 (2007).) is derived from DNA samples from a small number of anonymous Caucasian donors and, therefore, represents a small sampling of the broad array of human genetic variation. Additionally, this reference sequence contains both common and rare disease risk variants (Chen, R. & Butte, A. J. The reference human genome demonstrates high risk of type 1 diabetes and other disorders. Pac Symp Biocomput, 231-242 (2011).) and may bias interpretation of genetic variants aligned and called against the sequence.

With the advent of the human genome project and the draft sequences of human genomic DNA came promises to revolutionize personalized health care by tailoring risk modification, medications, and health surveillance to patients' individual genetic backgrounds. High-throughput whole genome sequencing ("Next generation sequencing") has revolutionized the study of genetic variation and facilitated a precipitous drop in the cost per quantum of genetic variation data generated. This trend has thus far outstripped Moore's law by a factor of two, opening the door for population-wide genome sequencing. As such, technologies for interpretation of the massive amounts of genetic data produced with each genome sequence must advance in step.

One of the upstream challenges to interpretation of this genetic data is the reliance on a human reference genome sequence to 1) identify the genomic location of the billions of short (30 to 500 base pair) sequence reads produced in a massively parallel fashion by high-throughput sequencing, and 2) identify variation in other individuals from this "normal" sequence.

Another barrier to the realization of the goal of genome interpretation pipelines is the difficulty in assigning "phase," or parental origin of genetic variants, in sequencing studies, because genotypes, not haplotypes, are given at each position. The assessment of compound heterozygous and multigenic disease risk, integration of sex-specific risk inheritance, and integration of genetic background in areas of high recombination, such as the Human Leukocyte Antigen Loci, will be crucial to understanding genome wide risk in related individuals, because these analyses are wholly reliant on phased haplotype data.

Another barrier to the realization of the goal of genome interpretation pipelines is the difficulty in assigning risk estimates to the millions of genetic variants present in any individual. These variants harbor between 50 and 100 potentially damaging mutations in genes associated with Mendelian ("single gene") disorders, the majority of which are of uncertain significance.

Therefore, there is a need for improved methods for improved methods for analyzing genome sequence data.

SUMMARY OF THE INVENTION

In an embodiment of the present invention, three novel human reference genome sequences were developed based on the most common population-specific DNA sequence ("major allele"). Methods were developed for their integration into interpretation pipelines for highthroughput whole genome sequencing.

To address bias inherent to the mapping, assembly, and interpretation of genetic variation data from high-throughput sequencing, an embodiment of the present invention uses three "major allele" reference sequences that capture most of the population-specific genetic variation present in three major population groups. Using the current human genome reference sequence as a scaffold, three ethnicityspecific human major allele references are developed for the major HapMap population groups (of Caucasian (CEU), East Asian (CHB/JPT), and African subpopulation (Yoruba, YRI) descent) using estimated allele frequency data at 7,917,426, 10,903,690, and 6,253,467 genomic positions cataloged in the 1000 genomes project. In an embodiment, though relatively insensitive for very rare genetic variation, the low coverage pilot sequencing data (which comprises the majority of population-specific variation data) has a sensitivity for an alternative allele of >99% at allele frequencies>10% and thus has high sensitivity for detecting the major allele. At every position at which the major allele differed from the reference sequence base, the major allele was substituted for the reference base. This resulted in reference base changes at 1,543,755, 1,658,360, and 1,676,213 positions in the CEU, YRI, and CHB/JPT populations, respectively. There were 796,548 positions common to all three HapMap population groups at which the major allele differed from the NCBI reference base. Variation from the NCBI reference genomes was relatively uniform across chromosomal locations with the exception of loci in and near the Human Leukocyte Antigen loci on chromosome 6.

Methods for integration of these novel human reference sequences into the pipeline for interpretation of high-throughput sequencing from individuals are as follows for certain embodiments of the present invention: 1) short sequence reads from massively parallel sequencing of individuals are aligned and mapped to the population specific reference genome which most closely recapitulates self-identified ethnicity, and 2) genetic variation in sequenced individuals is cataloged by comparison of mapped sequence data from individuals to the population specific major allele at that genomic position.

Another embodiment of the present invention is a method for resolving long-range haplotype phase based on family pedigree data, inheritance state determination, and population linkage disequilibrium data. A method according to an embodiment of the present invention provides for the evaluation of genome wide risk using phased haplotype data.

An embodiment of the present invention first applies the concept of inheritance state to the allele assortments resulting from single nucleotide variants. In any nuclear family, there are $2^n$ possible inheritance states, where n is the number of meiosis in the pedigree. An embodiment of the present invention uses a Hidden Markov Model (HMM) in which the hidden states correspond to the $2^n$ inheritance states as well as two fixed error states: 1) the compression/CNV state in which hemizygous structural variants in the study genomes or reference genome result in uniform heterozygosity across the quartet; and 2) the MIE-rich state which contains a high number of impossible allele assortments likely due to sequencing or assembly errors. Transition probabilities for each of the non-error and two error inheritance states are set according to the expected number of state transitions and the total number of allele assortments in the pedigree, with the remaining transition probability allocated to self-self transitions. In an embodiment, the Viterbi algorithm is used to find the most likely state path given the observed allele assortments, resulting in the assignment of an inheritance state to each allele assortment in which one or more family members have an allele differing from the reference sequence.

State transitions in this path correspond to recombination events, with recombination window resolution given by the distance between informative allele assortments. An embodiment of the present invention uses a combination of pedigree data and statistical phasing based on inheritance state and, for uniformly heterozygous positions, population linkage disequilibrium data to determine long-range haplotypes for families. In an embodiment, the inheritance state of the surrounding variants is used to phase the remaining heterozygous positions.

This information is informative for positions at which each of three individuals in a father-mother-child trio is heterozygous for a non-reference allele and the sibling is homozygous for the reference or non-reference allele. For uniformly heterozygous positions in which the family information is not informative, pair-wise pre-computed population linkage disequilibrium data is used to assign the minor allele to the paternal or maternal chromosome scaffolds according to maximization of aggregate $r^2$. In an embodiment, phasing is performed for each adult in contigs according to passage of allele contigs to one, both, or neither of the children. Phased haplotype data are used to find compound heterozygous and multigenic disease risk alleles using prioritization schemes. Parent of origin is used in a prior expectation in combinatorial likelihood ratio estimation for common disease risk.

An embodiment of the present invention for phasing leverages pedigree and population linkage disequilibrium data and rapidly provides haplotype phased data. In contrast to existing phasing algorithms, the methods of the present invention for providing long-range phased data provide opportunities for investigation of multigenic risk for disease incorporating gene loci at widely disparate locations on the same or even different chromosomes. Current risk prediction pipelines do not incorporate parent-of-origin into pipelines for genome annotation, despite evidence for specific effects of risk alleles for common disease, including diabetes type II, depending on parent of origin. The methods of the present invention for phasing and incorporation into risk prediction pipelines for personal genomes address this limitation.

Another embodiment of the present invention is a methodology for prioritizing variants relevant to inherited Mendelian ("single gene") disease syndromes according to disease phenotype, gene, and variant level information.

In an embodiment, non-synonymous variants (SNVs, also called nsSNPs) are annotated using a combination of prediction algorithms and manual curation. In order to prioritize the evaluation and delivery of information relating to the rare and novel variants, a rating schema is applied based on phenotype-level information about the variants in Mendelian-disease associated genes and predicted or experimentally derived variant pathogenicity. In an embodiment, this rating schema is applied to a data source built on the Online Mendelian Inheritance in Man (OMIM) database, curated to include phenotypic information about only Mendelian diseases, and disease specific and private databases.

These and other embodiments can be more fully appreciated upon an understanding of the detailed description of the invention as disclosed below in conjunction with the attached figures.

BRIEF DESCRIPTION OF THE DRAWINGS

The following drawings will be used to more fully describe embodiments of the present invention.

FIG. 2C is a graph illustrating a combination of quality score calibration using orthogonal genotyping technology and filtering SNVs in error prone regions (MIE-rich and compression regions) identified by the HMM resulted in >90% reduction in the genotype error rate estimated by the MIE rate per 10 mega bases (Mbp).

FIG. 35 plots the parental haplotype contribution to disease risk for each child (points) for the son according to an embodiment of the present invention.

FIG. 36 is a table (Table 1) showing data for putative loss of function variants across the family quartet according to an embodiment of the present invention.

FIG. 37 is a table (Table 2) showing data for rare variants with known clinical associations according to an embodiment of the present invention.

FIG. 38 is a table (Table 3) showing data for drub metabolizing enzyme variants according to an embodiment of the present invention.

FIG. 39 is a table (Table 4) showing data for genetic pharmacological response predictions according to an embodiment of the present invention.

FIG. 46 is a table (Table 5) showing data for a prioritization schema for rare and novel SNPs according to an embodiment of the present invention.

FIG. 47 is a table (Table 6) showing data for variants of potential significance in OMIM-curated disease associated genes according to an embodiment of the present invention.

FIG. 48 is a table (Table 7) showing data for compound heterozygous and homozygous variants in Mendelian disease associated genes according to an embodiment of the present invention.

FIG. 49 is a table (Table 8) showing information for an exemplary pharmacogenomics annotation according to an embodiment of the present invention.

FIG. 50 is a table (Table 9) showing data for variants associated with drug efficacy according to an embodiment of the present invention.

FIG. 51 is a table (Table 10) showing data for variants associated with adverse drug response according to an embodiment of the present invention.

FIG. 52 is a table (Table 11) showing data for variants associated with drug dosing according to an embodiment of the present invention.

DETAILED DESCRIPTION OF THE INVENTION

Figure 40:
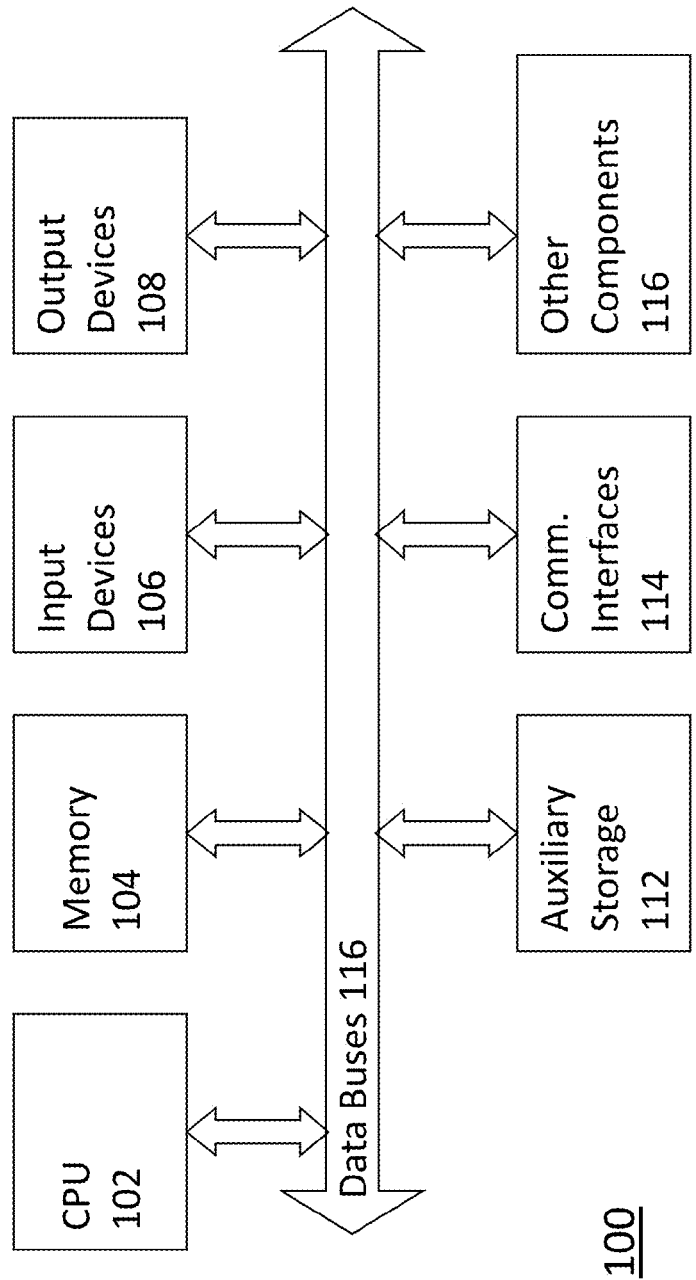
FIG. 40 is a block diagram of a computer system on which the present invention can be implemented.

Among other things, the present invention relates to methods, techniques, and algorithms that are intended to be implemented in a digital computer system 100 such as generally shown in FIG. 40. Such a digital computer or embedded device is well-known in the art and may include the following.

Computer system 100 may include at least one central processing unit 102 but may include many processors or processing cores. Computer system 100 may further include memory 104 in different forms such as RAM, ROM, hard disk, optical drives, and removable drives that may further include drive controllers and other hardware. Auxiliary storage 112 may also be include that can be similar to memory 104 but may be more remotely incorporated such as in a distributed computer system with distributed memory capabilities.

Computer system 100 may further include at least one output device 108 such as a display unit, video hardware, or other peripherals (e.g., printer). At least one input device 106 may also be included in computer system 100 that may include a pointing device (e.g., mouse), a text input device (e.g., keyboard), or touch screen.

Communications interfaces 114 also form an important aspect of computer system 100 especially where computer system 100 is deployed as a distributed computer system. Computer interfaces 114 may include LAN network adapters, WAN network adapters, wireless interfaces, Bluetooth interfaces, modems and other networking interfaces as currently available and as may be developed in the future.

Computer system 100 may further include other components 116 that may be generally available components as well as specially developed components for implementation of the present invention. Importantly, computer system 100 incorporates various data buses 116 that are intended to allow for communication of the various components of computer system 100. Data buses 116 include, for example, input/output buses and bus controllers.

Indeed, the present invention is not limited to computer system 100 as known at the time of the invention. Instead, the present invention is intended to be deployed in future computer systems with more advanced technology that can make use of all aspects of the present invention. It is expected that computer technology will continue to advance but one of ordinary skill in the art will be able to take the present disclosure and implement the described teachings on the more advanced computers or other digital devices such as mobile telephones or "smart" televisions as they become available. Moreover, the present invention may be implemented on one or more distributed computers. Still further, the present invention may be implemented in various types of software languages including C, C++, and others. Also, one of ordinary skill in the art is familiar with compiling software source code into executable software that may be stored in various forms and in various media (e.g., magnetic, optical, solid state, etc.). One of ordinary skill in the art is familiar with the use of computers and software languages and, with an understanding of the present disclosure, will be able to implement the present teachings for use on a wide variety of computers.

The present disclosure provides a detailed explanation of the present invention with detailed explanations that allow one of ordinary skill in the art to implement the present invention into a computerized method. Certain of these and other details are not included in the present disclosure so as not to detract from the teachings presented herein but it is understood that one of ordinary skill in the at would be familiar with such details.

Overview of Methods According to Embodiments of the Present Invention

To be described first is an overview of methods according to embodiments of the present invention. Afterwards, further details of methods according to embodiments of the present invention will be described.

Ethics and DNA Sequence Generation

Figure 1A:
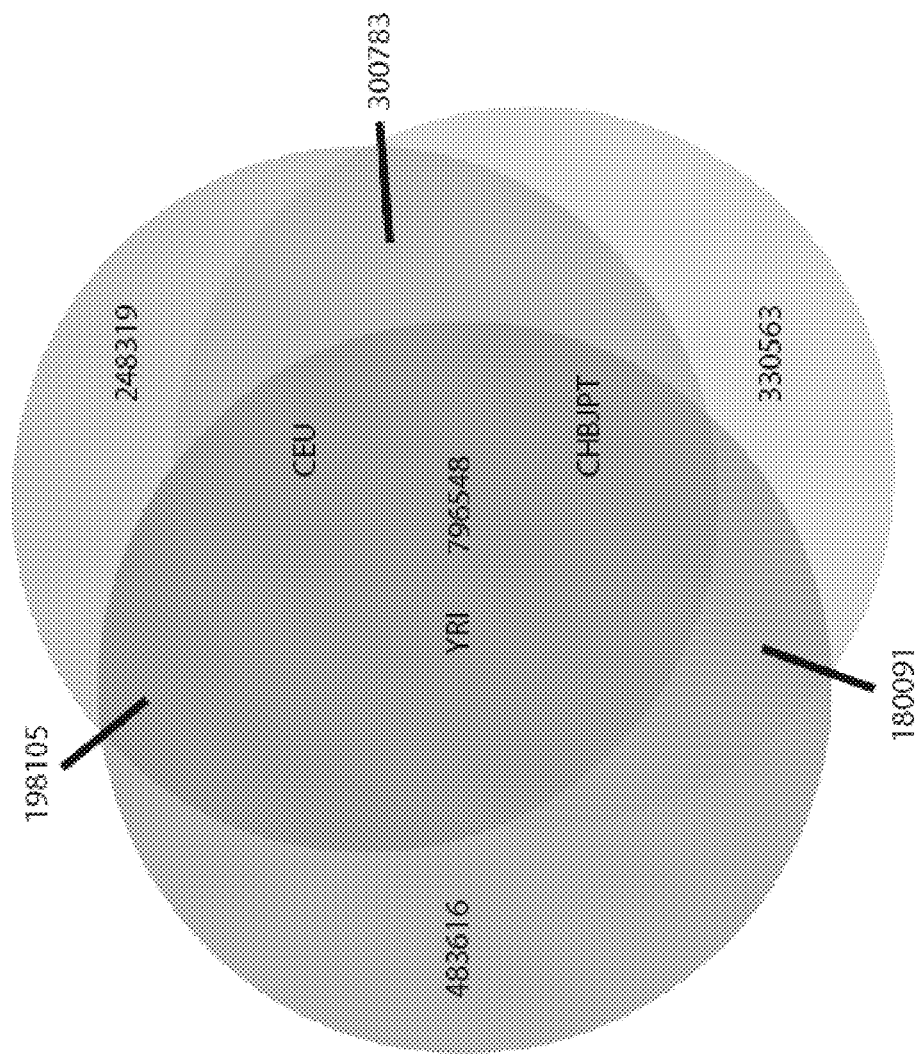
FIG. 1A illustrates how approximately half of the positions shown were shared between all three HapMap population groups, with the YRI population containing the greatest number of major alleles differing from the NCBI reference sequence according to an embodiment of the present invention.
Figure 1B:
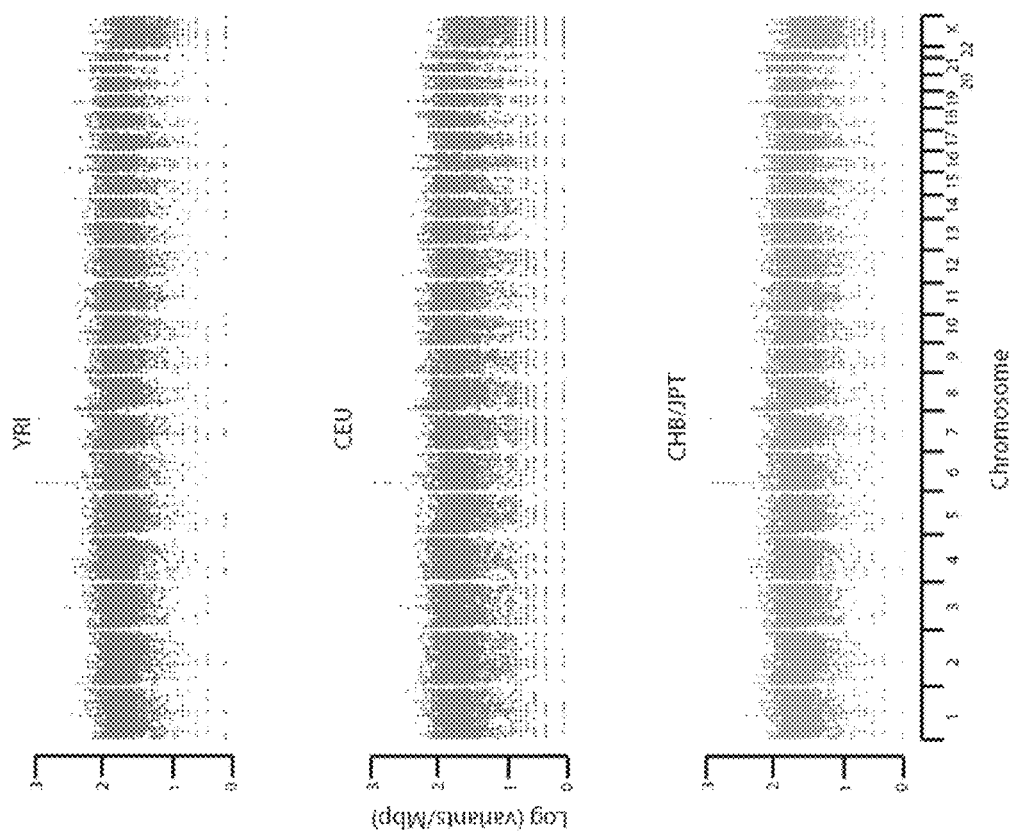
FIG. 1B graphically illustrates the number of positions per Mbp at which the major allele differed from the reference base by chromosome and HapMap population according to an embodiment of the present invention.
Figure 1C:
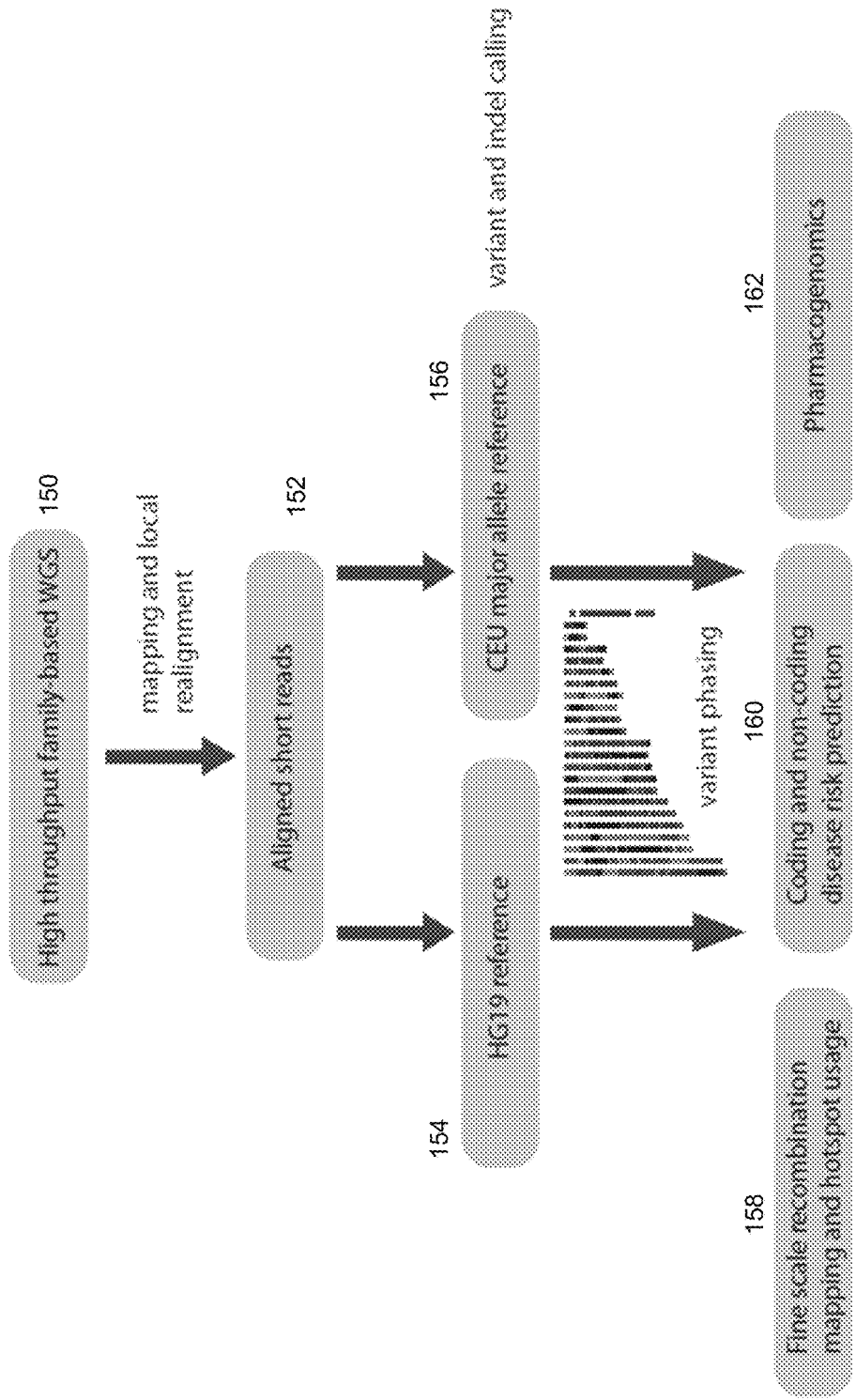
FIG. 1C illustrates a workflow for phased genetic risk evaluation using whole genome sequencing according to an embodiment of the present invention.

Genetic counseling of test subjects was performed at the time of DNA isolation, and additional counseling was performed concurrent with interpretation of variants with disease risk and pharmacological response implications (see steps 160 and 162 of FIG. 1C). After informed written consent or assent (for minors), genomic DNA was extracted from peripheral blood from the study subjects and sequenced using reversible terminator massively parallel sequencing at Illumina, Inc (San Diego, Calif.). Sequenced reads were mapped to the NCBI human reference genome 37.1 (HG19) using BWA software (Li, H. & Durbin, R. Fast and accurate short read alignment with Burrows-Wheeler transform. Bioinformatics 25, 1754-1760 (2009)) with local realignment around known indels performed by GATK. A total of 5.98 billion sequence reads mapped uniquely to the reference sequence across the quartet, resulting in 448 gigabases of sequence data. Variant calling was performed using SAMtools multi-sample pileup and BCFtools by comparison with HG19 and the CEU major allele reference (see steps 154 and 156 of FIG. 1C).

Inheritance State Determination and Recombination Mapping

The inheritance state analysis algorithm developed by Roach, et al (Roach, J. C., et al. Analysis of genetic inheritance in a family quartet by whole-genome sequencing. Science 328, 636-639 (2010)), was foundational to resolve contiguous blocks of single nucleotide variants into one of four Mendelian inheritance states using a Hidden Markov Model: paternal identical, in which each child receives the same allele from the father but different alleles from the mother; maternal identical, in which each child receives the same allele from the mother but different alleles from the father; identical; and nonidentical. Two additional non-Mendelian inheritance states were modeled (compression and Mendelian inheritance error (MIE) rich, described further below (see also Roach, J. C., et al. Analysis of genetic inheritance in a family quartet by whole-genome sequencing. Science 328, 636-639 (2010).)). The modeling of two additional error states allowed for identification of error-prone regions that are difficult to sequence or properly map and genotype. After excluding error prone regions that are potential sources of spurious recombination site inferences, the variant allele assortments were re-analyzed using only four Mendelian inheritance states, identifying meiotic crossover windows as intervals between SNVs defining the end and start, respectively, of contiguous inheritance state blocks.

Phasing

Figure 43:
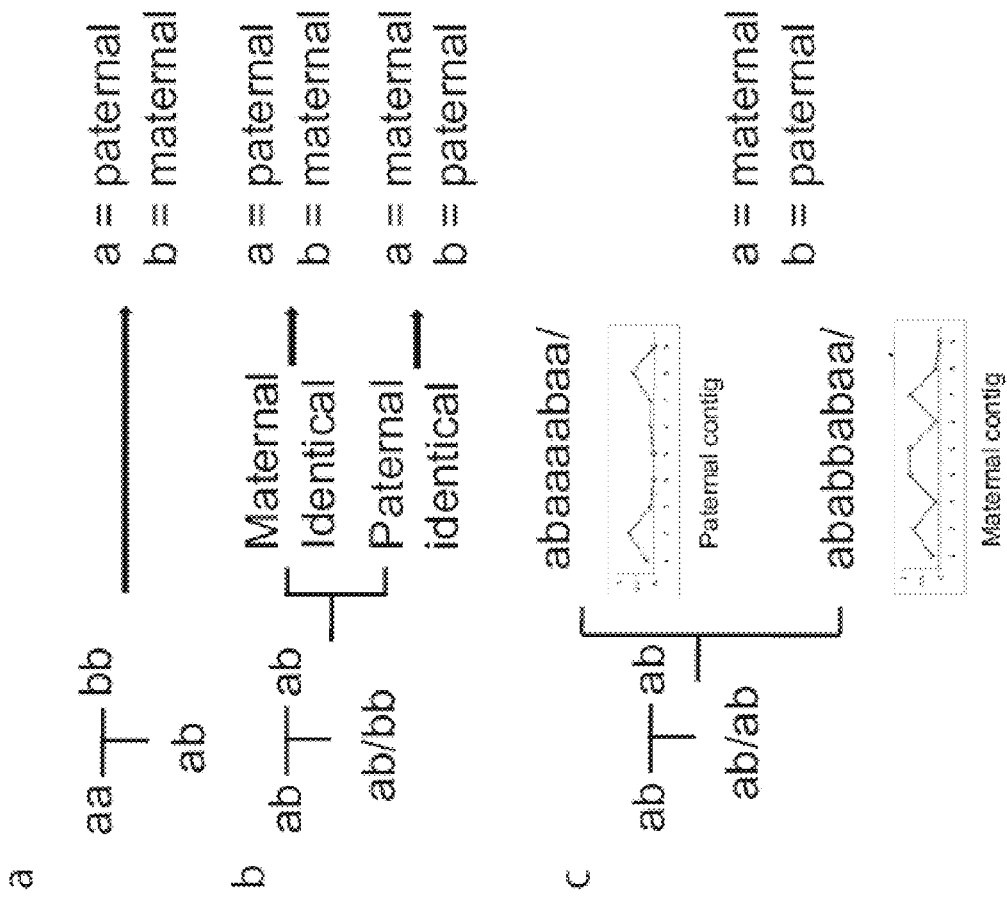
FIGS. 43A-43C are charts showing the manner in which inheritance state was determined for all allele assortments in the variant call sets according to embodiments of the present invention.

A combination of per-trio pedigree information, inheritance state information, and population linkage disequilibrium data, described in full further below, were used to provide long-range phasing of each of the four family members (See FIG. 43). Briefly, the phase of heterozygous variants in the children were resolved by: 1) the inheritance state of the surrounding variants in contiguous inheritance blocks (for variant positions at which each of three individuals in a father-mother-child trio was heterozygous for a non-reference allele and the sibling was homozygous for the reference or non-reference allele); 2) maximization of aggregate $r^2$ from pair-wise pre-computed population linkage disequilibrium data from the SNP Annotation and Proxy Search (SNAP) database. (Johnson, A. D., et al. SNAP: a web-based tool for identification and annotation of proxy SNPs using HapMap. Bioinformatics 24, 2938-2939 (2008).) Phasing was performed for each adult in contigs according to passage of allele contigs to one, both, or neither of the children.

The inheritance state was determined for all allele assortments in the variant call sets as described in the methods herein. As shown in FIG. 43A, a combination of pedigree data was used to phase mother-father-child trios. As shown in FIG. 43b, the inheritance state of neighboring regions to phase positions in which all members of a mother-father-child trio were heterozygous and the sibling was homozygous for the reference or non-reference allele. For uniformly heterozygous positions, the non-reference allele was phased using a maximum likelihood model to assign the non-reference allele to paternal or maternal chromosomes based on population linkage disequilibrium with phased SNVs within 250 kb as shown in FIG. 43B. In the figures, a corresponds to the reference allele and b to the non-reference allele.

Immunogenotyping

An iterative, leave-one-out heuristic search was used as described further below for the nearest tag haplotype for common HLA types (de Bakker, P. I., et al. A high-resolution HLA and SNP haplotype map for disease association studies in the extended human MHC. Nat Genet 38, 1166-1172 (2006)) using phased variant data, assigning an HLA type to each chromosome for each study subject based on this nearest tag haplotype.

Rare Variant Prioritization

A combination of prediction algorithms were used based on characteristics of amino acid change and predicted protein structural and functional changes (SIFT, Polyphen2) (Adzhubei, I. A., et al. A method and server for predicting damaging missense mutations. Nat Methods 7, 248-249 (2010); Ng, P. C. & Henikoff, S. SIFT: Predicting amino acid changes that affect protein function. Nucleic Acids Res 31, 3812-3814 (2003)), and a novel MSA of 46 mammalian species, in which the evolutionary rate and time span was computed at each genomic position according to the method of Fitch (Fitch, W. Toward Defining the Course of Evolution: Minimum Change for a Specific Tree Topology. Systematic Zoology 20, 406-416 (1971)) to provide genetic risk predictions about non-synonymous coding variants in Mendelian-disease associated genes. These variants were further manually annotated according to disease phenotype features and variant pathogenicity as described with regard to Table 5 (FIG. 46). Methods for functional prediction of codon usage bias, splice site disruption, and mRNA stability for synonymous coding variants, and annotation of variants in important non-coding regions are described further below.

Common Variant Risk Prediction

A manually curated database was developed of greater than 4000 publications investigating associations between 35,997 SNPs and 1,194 diseases or traits. A combinatorial approach was applied for point estimation of likelihood ratios of disease-SNP association, and generated composite likelihood ratios for groups of SNPs and associated diseases as described previously (Ashley, E. A., et al. Clinical assessment incorporating a personal genome. Lancet 375, 1525-1535 (2010).) from phased genetic variant data (described further below). In this analysis, included were disease-SNP associations replicated in greater than 2 GWAS with a total sample size of greater than 2000 individuals and only SNPs genotyped in the HapMap CEU population to provide a population-risk framework for interpreting composite likelihood ratios.

Pharmacogenomics 432 clinical annotations between 298 SNPs and drugs (Pharmacogenomics Knowledge Base, PharmGKB) were compiled. For all family members in the quartet, associations were evaluated between 248 phased SNPs, including 147 heterozygous loci, and 141 drugs (Tables 9-11 (FIGS. 50-52). A full description of materials and methods is presented below.

Further Details of Methods According to Embodiments of the Present Invention

To be describe below are certain details relating to methods according to embodiments of the present invention for generating and analyzing synthetic major allele reference genomes. Although certain details will be provided, one of skill in the art will understand that many variations are possible without deviating from the teachings of the present invention.

Data Sources

The 1000 genomes project has provided an extensive catalog of genetic variation in human populations, allowing for fine-scale mapping of variation in several different ethnic groups. (Durbin, R. M., et al. A map of human genome variation from population-scale sequencing. Nature 467, 1061-1073 (2010).) Data regarding allele frequencies in each of the three major Haplotype Map (HapMap) populations was obtained from genotypes in the low coverage whole genome sequencing pilot (pilot 1) of the 1000 genomes project (Dec. 13, 2010 release). This compendium catalogs variation at 7,917,426, 10,903,690, and 6,253,467 sites in the CEU, YRI, and CHB/JPT populations, respectively, with sensitivity for an alternative allele of >99% at allele frequencies>10%.

Synthetic Major Allele Reference Sequence Generation

Genomic positions were first identified corresponding to NCBI reference genome sequence 37.1 coordinates at which the major allele (defined as estimated allele frequency>50%) differed from the reference sequence base. The major allele was then substituted for each of the three HapMap populations for the reference base to create three synthetic ethnicity-specific major allele references, specific to each of the CEU, YRI, and CHB/JPT populations. This resulted in a reference base change at 1,543,755, 1,658,360, and 1,676,213 positions in the CEU, YRI, and CHB/JPT populations, respectively. As demonstrated in FIG. 1A, there were 796,548 positions common to all three population groups at which the major allele differed from the NCBI reference base. The YRI population had the largest proportion of base changes with a major allele not corresponding to either of the two other population groups. The frequency with which the reference base differed from the ethnicity-specific dominant base was relatively consistent across autosomes, with the exception of chromosome 6, which demonstrated increased sequence divergence in the reference genome from each of the three dominant population alleles in the vicinity of the HLA locus (see FIG. 1B). The major allele reference sequences are freely available upon request from the authors.

FIGS. 1A-1C show the development of major allele reference sequences and genetic risk prediction workflow according to embodiments of the present invention. In an embodiment, allele frequencies from the low coverage whole genome sequencing pilot of the 1000 genomes data were used to estimate the major allele for each of the three main HapMap populations. The major allele was substituted for the NCBI reference sequence 37.1 reference base at every position at which the reference base differed from the major allele, resulting in approximately 1.6 million single nucleotide substitutions in the reference sequence. As shown in FIG. 1A, approximately half of these positions were shared between all three HapMap population groups, with the YRI population containing the greatest number of major alleles differing from the NCBI reference sequence. FIG. 1B shows the number of positions per Mbp at which the major allele differed from the reference base by chromosome and HapMap population. The proportion of alleles differing from the NCBI reference sequence differed most in the positions surrounding the Human Leukocyte Antigen (HLA) loci on chromosome 6.

FIG. 1C is a workflow diagram for phased genetic risk evaluation using whole genome sequencing according to an embodiment of the present invention.

Subject and Sample Characteristics

Study Subjects

Figure 2A:
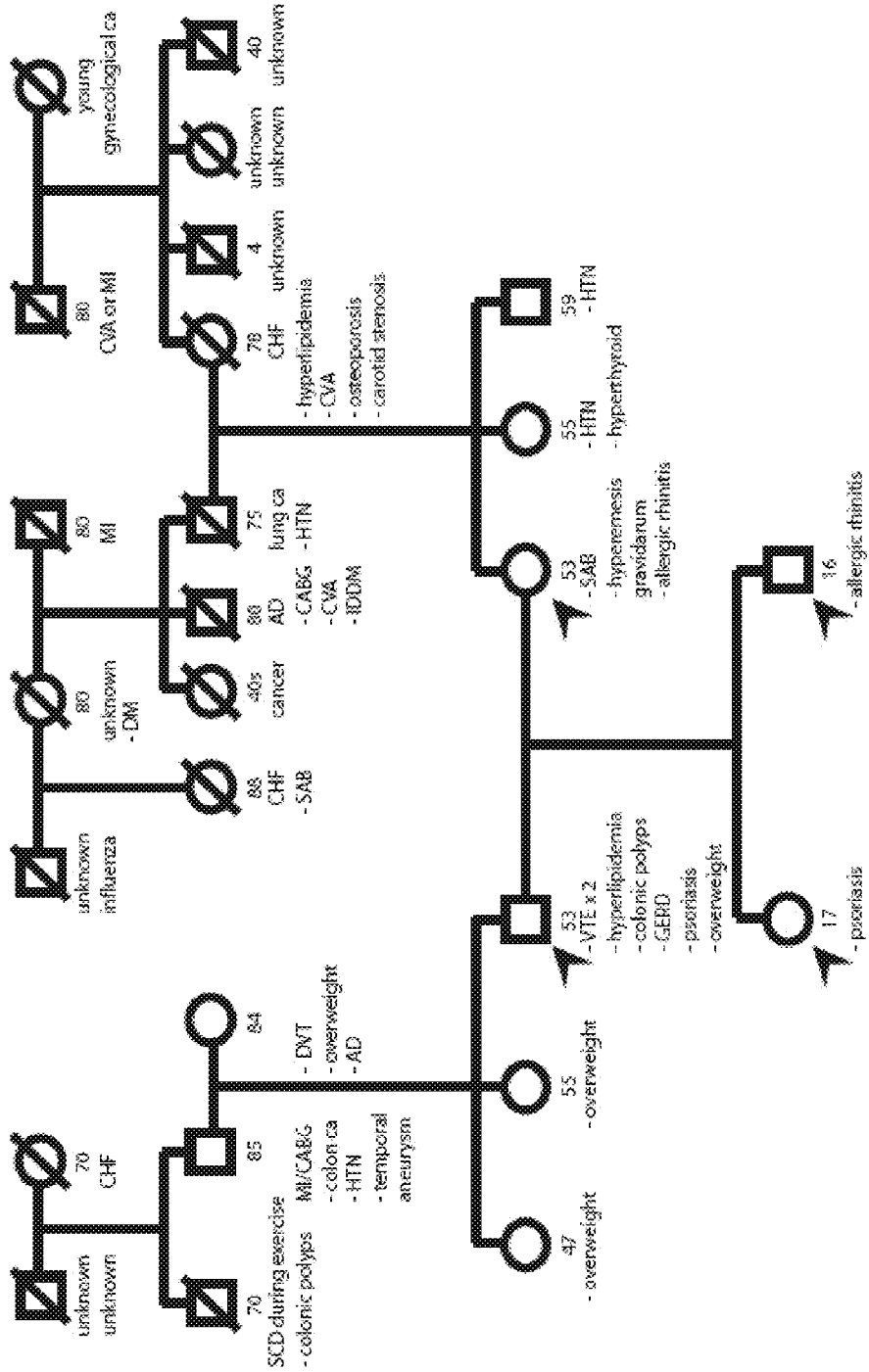
FIG. 2A illustrates a family pedigree with known medical history.

Clinical characteristics of study subjects are described in graphical form in the pedigree in FIG. 2A. One study subject (the father) had a history of recurrent venous thromboembolism and hyperlipidemia and was taking warfarin for anticoagulation, the lipid lowering medications ezetemibe and simvastatin, and the proton pump inhibitor esomeprazole. Two family members had a history of psoriasis (father and daughter). Two family members had a history of allergic rhinitis (mother and son) and were taking loratidine on an as needed basis. Both parents self-reported northern European ancestry.

Clinical characteristics of study subjects are described in graphical form in the pedigree shown in FIG. 2A. Two first-degree family members, including the father in the sequenced quartet, have a history of venous thrombosis (e.g., DVT as shown in FIG. 2A); notably, the sequenced father has a history of recurrent venous thromboembolism (e.g., VTE as shown in FIG. 2A) despite systemic anticoagulation. Both parents self-reported northern European ancestry. As shown, ages represent age of death for deceased subjects or the age at the time of medical history collection in 2010 for living family members. Arrows denote sequenced family members. Abbreviations are as follows: AD, Alzheimer's disease; CABG, coronary artery bypass graft surgery; CHF, congestive heart failure; CVA, cerebrovascular accident; DM, diabetes mellitus; DVT, deep venous thrombosis; GERD, gastroesophageal reflux disease; HTN, hypertension; IDDM, insulin-dependent diabetes mellitus; MI, myocardial infarction; SAB, spontaneous abortion; SCD, sudden cardiac death.

The study was approved by the Stanford University Institutional Review Board and all study subjects attended genetic counseling and provided informed written consent (or assent, in the case of the children). This consent process occurred at two points in time: before the sequencing was performed (overseen by Illumina, Inc., and conducted with a clinical geneticist) and before this clinical interpretation was performed (conducted with a genetic counselor and research assistant). Pedigree and genotyping results were discussed in a genetic counseling session in the context of information that may be obtained in a clinical interpretation of genome sequence data and the personal and family risks and benefits that may arise in obtaining this information. (Ormond, K. E., et al. Challenges in the clinical application of whole-genome sequencing. Lancet 375, 1749-1751 (2010).)

Genome Sequencing, Mapping, and Base Calling.

Genomic DNA Isolation and Sequencing Library Preparation

Peripheral blood was obtained from study subjects and sample DNA was directly isolated according to standard protocols. Genomic DNA was fragmented by sonication and sequencing libraries were prepared by clonal amplification, end repair, and sequencing adapter ligation according to standard Illumina protocol by Illumina, Inc. (San Diego, Calif.). (Bentley, D. R., et al. Accurate whole human genome sequencing using reversible terminator chemistry. Nature 456, 53-59 (2008).)

Sequence Generation

Illumina Inc. performed all sequencing reactions on the GA II instrument using massively parallel reversible terminator (sequencing by synthesis) chemistry to generate 75 base pair paired-end reads. (Ashley, E. A., et al. Clinical assessment incorporating a personal genome. Lancet 375, 1525-1535 (2010).) See step 150 of FIG. 1C. Sequence reads passing standard Illumina GA pipeline filters were retained for further analysis.

Sequence Alignment and Mapping

Paired-end short reads were aligned to NCBI reference genome build 37.1 (obtained from the UCSC Golden Path genome browser) using the Burrows-Wheeler Aligner (BWA) software version 0.5.8a as shown in step 152 of FIG. 1C. (Li, H. & Durbin, R. Fast and accurate short read alignment with Burrows-Wheeler transform. Bioinformatics 25, 1754-1760 (2009).) Reads were trimmed to a length of 35 base pairs if the phred-like quality score was less than 20; default settings were otherwise used, resulting in sequence alignment map format (SAM) alignment files for paired end reads. Software from the Genome Analysis Tool Kit (GATK) version 1.0.4075 was then used to remove PCR duplicates and perform sample-level local realignment around known indels. Finally, mate pair information was re-synced using the Picard FixMateInformation tool and base quality score recalibration was performed using GATK, producing an aligned, cleaned binary alignment format (BAM) file for each study subject.

Base Calling and Variant Calling

The samtools multi-sample pileup tool was used with default settings to compute likelihoods of observed base data at each covered position given each possible underlying genotype. BCFtools was used to apply prior probabilities of each genotype and perform base calling against both the NCBI reference genome version 37.1 and the CEU major allele reference genome sequence created as described above. Single nucleotide variants were identified at an average distance of 699 base pairs when compared with the NCBI reference and 809 base pairs when compared with the CEU major allele reference. Short indels were called concurrently with single nucleotide variants using the samtools multi-sample pileup tool. As described in FIG. 41A, this resulted in genotype calls at 91.7%, 92.3%, 92.4%, and 92.4% of all chromosomal positions in the mother, father, son, and daughter, respectively. Across the quartet 91.6% of chromosomal positions were genotyped in all four family members. Haploid depth of coverage was 37.3× in the mother, 37.1× in the father, 46.2× in the son, and 36.2× in the daughter (FIG. 41B). At 3,858 variant positions the genotype for at least one family member differed when compared to the HG19 and CEU major allele references (see steps 154 and 156, respectively, of FIG. 1C), most frequently in the vicinity of indels. Two loci at rs757210 and rs1553318 had known disease associations in genome-wide association studies meeting the criteria for inclusion in common variant risk analysis outlined below. In both instances the genotypes in the variant calls against the CEU major allele reference were concordant with previously observed alleles reported in dbSNP 132, while the variant alleles in calls against the HG19 reference sequence were not reported previously. Across the family quartet the calculated transition to transversion ratio (Ti/Tv) in the final call set was 2.49, which corresponds to previous estimates of expected Ti/Tv. (Nachman, M. W. & Crowell, S. L. Estimate of the mutation rate per nucleotide in humans. Genetics 156, 297-304 (2000).)

Figure 41:
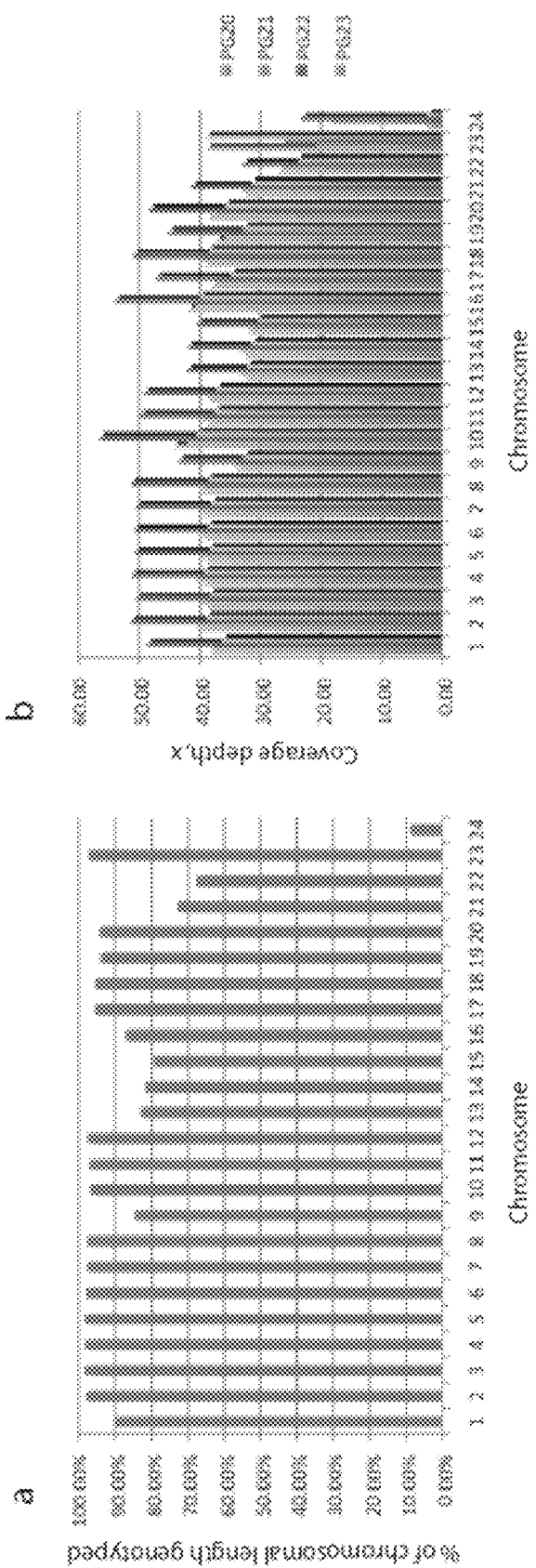
FIGS. 41A-41B are plots of genotype coverage in quartet subjects according to an embodiment of the present invention.

Shown in FIG. 41 are charts for paired end short reads that were mapped to NCBI reference genome 37.1 as described in the supplementary methods. Shown in FIG. 41A is the percentage of total chromosome length (including positions not covered by the reference sequence) successfully genotyped in all four individuals in the family quartet (Chromosome 23=X chromosome, chromosome 24=Y chromosome). Shown in FIG. 41B is a chart of Haploid depth of coverage by chromosome and individual at each successfully genotyped position. PG20=mother, PG21=father, PG22=son, PG23=daughter.

Genetic Variant Quality Control

Both orthogonal genotyping technology and bioinformatics tools were used to perform variant quality control and exclude likely spurious genotype calls. For confirmatory testing of common variants and quality score calibration, genomic DNA isolated from saliva from all four study subjects was genotyped using a customized array built on the Illumina HumanHap 550K+Genotyping BeadChip (23 and ME, Inc., Mountain View, Calif.). This genotyping array contains probesets corresponding to approximately 578,000 single nucleotide variants, including ~30,000 variants unique to the 23 and ME array implementation. The discordance rate between array-based genotyping and sequencing variants was calculated according to mapping quality, base depth, and genotype quality. As described above, the base quality score was filtered at the stage of initial BWA mapping. All discordant calls were excluded from risk interpretation of genetic variants, as neither technology (array based genotyping or whole genome sequencing) was considered the gold standard. This information was also subsequently used to choose quality score cutoffs as follows: variants were retained if the mean mapping quality was greater than 40, the average base coverage depth was greater than 10, and the average and minimum genotype qualities were greater than 45 and 15, respectively.

The information provided by family-based sequencing for quality control of variant calls was also leveraged. In a family quartet, of the 81 possible genotype combinations in a bialleleic state, 52 correspond to Mendelian inheritance errors (MIEs), or allele assortments that are impossible under Mendel's laws. A very small subset of these allele assortments will be due to germ-line or somatic de novo mutation events, gene conversions, or hemizygous structural variation. However, the overwhelming majority of these allele assortments result from sequencing errors. Therefore, the identification and sequestering of these variants can greatly reduce the genotyping error rate. Similarly, the identification of regions of the genome that are prone to sequencing errors or errors in mapping and consensus assembly due to discordant structural variation between the reference and sample sequence can greatly reduce the error rate. (Roach, J. C., et al. Analysis of genetic inheritance in a family quartet by whole-genome sequencing. Science 328, 636-639 (2010).) Lastly, the identification of allele assortments discordant with the neighboring inheritance state (state consistency errors, SCEs) allows for identification of sequencing errors. All MIEs and SCEs were excluded from subsequent annotation as well as all variants in error prone regions.

Error Rate Estimation

Genotyping error rate was estimated using three methods: 1) estimation of the MIE rate per base sequenced, 2) estimation of the MIE and SCE rate in the 24% of the genome in which the children were identical by descent, and 3) estimation of the discordant rate between the 23 and ME genotyping and the whole genome sequence call. All three methods yielded approximately the same error rate at each stage of variant quality control. As demonstrated in FIG. 2C, the greatest reduction in error rate occurred with filtering of variants in error prone regions, with a final estimated error rate by MIE rate per base pair sequenced of $2.1 \times 10^{-6}$ for the CEU and HG19 variant call sets. The overall SCE rate per base pair sequenced in identical-by-descent regions for the offspring was $5.26 \times 10^{-7}$ for both CEU and HG19 call sets. This represents a 94% overall reduction in error rate using a combination of orthogonal genotype confirmation and filtering of error prone regions.

Inheritance State Analysis and Phasing

Family Inheritance State Analysis

The concept of inheritance state developed by Roach, et al, was applied to the allele assortments resulting from single nucleotide variants in each of the four family members. (Kong, A., et al. Sequence variants in the RNF212 gene associate with genome-wide recombination rate. Science 319, 1398-1401 (2008).) This nuclear family of four has 4 possible inheritance states: maternal identical in which the children each inherit the same allele from the mother; paternal identical in which the children each inherit the same allele from the father; identical in which the children are identical by descent and inherit the same allele from both parents; and nonidentical in which the children inherit different alleles from both parents. Two algorithms were used to determine inheritance state for neighboring SNVs. The first heuristic algorithm binned allele assortments into 100 kb pair regions based on chromosomal position and assigned an inheritance state according to the total number of SNPs in the bin consistent with that inheritance state.

The second algorithm was based on a Hidden Markov Model (HMM) in which the hidden states correspond to the four inheritance states described above and two error states first described by Roach, et al. (Roach, J. C., et al. Analysis of genetic inheritance in a family quartet by whole-genome sequencing. Science 328, 636-639 (2010).) These two states were the compression/CNV state, in which hemizygous structural variants in the study genomes or reference genome result in uniform heterozygosity across the quartet, and the MIE-rich state, which contains a high number of impossible allele assortments likely due to sequencing or assembly errors. The emission probabilities for allele assortments consistent with each inheritance state were set equal to one another and the total probability of emitting an inconsistent allele assortment was set to 0.005. For the CNV/compression state, the emission probability for uniform heterozygosity was set to 0.66. The MIE-rich state was modeled to emit an MIE 33% of the time and a consistent allele assortment 67% of the time, with equal probability weight for each consistent allele assortment. Transition probabilities for each of the four non-error and two-error inheritance states were set according to the expected number of state transitions and the total number of allele assortments in the quartet with the remaining transition probability allocated to self-self transitions. Manipulation of these transition probabilities within four orders of magnitude did not qualitatively change the resulting inheritance state determination. The Viterbi algorithm was used to find the most likely state path given the observed allele assortments, resulting in the assignment of an inheritance state to each allele assortment in which one or more family members had an allele differing from the reference sequence. State transitions in this path correspond to recombination events, with recombination window resolution given by the distance between informative allele assortments.

As CNV/compression regions and MIE-rich regions are potential sources of spurious state switches and, therefore, incorrectly inferred recombination events. The identification of these regions can improve recombination inference accuracy. After excluding SNVs in these regions, a four state HMM was developed and the Viterbi path again found, resulting in an improved median recombination window resolution 963 base pairs. To identify enrichment for these recombination windows within known hotspots, a quantitative trait associated with PRDM9 allele status, calculated was the number of recombinations in which a maximum recombination rate of >10 cM/Mbp was observed. A Monte Carlo simulation was employed with 10,000 replicates to estimate the hotspot enrichment for 106 randomly placed recombination windows of width equal to that observed in the quartet, finding that 4.1% of these random windows were in hotspots. Given that 52 recombination windows in hotspots in the quartet were found, this corresponds to a p value for hotspot enrichment of $2.0 \times 10^{-73}$.

Phasing

Haplotype phase is important to understanding genetic risk in patients with and without disease phenotypes. Resolution of genotype information provided by whole genome sequencing into phased haplotypes has long proved difficult. A variety of statistical phasing techniques exist for inferring haplotype phase in unrelated individuals that seek to minimize recombination events and/or maximize the likelihood of heterozygous positions in high linkage disequilibrium assorting together on contigs. (Williams, A. L., Housman, D. E., Rinard, M. C. & Gifford, D. K. Rapid haplotype inference for nuclear families. Genome Biol 11, R108 (2010); Marchini, J., Howie, B., Myers, S., McVean, G. & Donnelly, P. A new multipoint method for genome-wide association studies by imputation of genotypes. Nat Genet 39, 906-913 (2007); Kruglyak, L., Daly, M. J., Reeve-Daly, M. P. & Lander, E. S. Parametric and nonparametric linkage analysis: a unified multipoint approach. Am J Hum Genet 58, 1347-1363 (1996); Donnelly, K. P. The probability that related individuals share some section of genome identical by descent. Theor Popul Biol 23, 34-63 (1983); Abecasis, G. R., Cherry, S. S., Cookson, W. O. & Cardon, L. R. Merlin—rapid analysis of dense genetic maps using sparse gene flow trees. Nat Genet 30, 97-101 (2002).) These techniques do not provide long-range phasing; however, precluding assessment of multigenic contribution to disease phenotypes or assessment of parental contribution to risk profiles. Father-mother-child trio sequencing provides information on long-range haplotype phase but only provides definitive phasing information at ~80% of heterozygous positions, as uniformly heterozygous positions are not informative. Sequencing an additional sibling allows for precise identification of meiotic crossovers, as well as a framework for understanding the inheritance state of contiguous polymorphic markers. A combination of pedigree data and statistical phasing based on inheritance state and, for uniformly heterozygous positions, population linkage disequilibrium data was used to determine long-range haplotypes for the family quartet (heuristic described in FIG. 43A-43C). The phase of approximately 84% of heterozygous positions in each child could be resolved by pedigree data alone. The inheritance state of the surrounding variants was used to phase 11% of the remaining heterozygous positions. This information was most informative for positions at which each of three individuals in a father-mother-child trio was heterozygous for a non-reference allele and the sibling was homozygous for the reference or non-reference allele. For uniformly heterozygous positions in which the family information is not informative, pair-wise pre-computed population linkage disequilibrium data was used from the SNP Annotation and Proxy Search (SNAP) database (Johnson, A. D., et al. SNAP: a web-based tool for identification and annotation of proxy SNPs using HapMap. Bioinformatics 24, 2938-2939 (2008)) to assign the minor allele to the paternal or maternal chromosome scaffolds according to maximization of aggregate $r^2$. Specifically, SNPs were considered that were genotyped in the HapMap II and III CEU populations with $r^2$ values>0.3 within 250 kb of the uniformly heterozygous position for this analysis given the inconsistent quality of linkage data outside this window. For each haplotype scaffold hm and hp and uniformly heterozygous locus 1, the likelihood of 1 residing on h was calculated as:

$$L(l; h) = \begin{cases} 1, r_i^2 = 1, \\ \frac{1}{n}\sum_n r_i^2, r_i^2 \neq 1 \end{cases} \quad (1)$$

where n is the number of heterozygous loci on h, and $r_i^2$ is the value for $r^2$ between the minor allele at 1 and the minor allele at heterozygous loci i on h. The minor allele was then placed at 1 on haplotype scaffold $h_m$ or $h_p$ according to $L_{max}$=max($L_m, L_p$).

This methodology allowed for phasing 34% of the remaining uniformly heterozygous positions. Finally, phasing was performed for each adult in contigs according to passage of allele contigs to one, both, or neither of the children. Phasing of adult contigs across recombination sites was not attempted due to largely uninformative linkage disequilibrium structure across recombination sites, which fell into areas of high population-averaged recombination rates. This combination of pedigree and population-linkage disequilibrium-based phasing resulted in phase resolution of 97.9% of heterozygous positions; family information alone informed phasing of 96.8% of positions.

Immunogenotyping

Phased genetic variant information simplifies greatly the combinatorial problem of resolving clinically relevant haplotypes in genomic locations with high recombination rates, in which traditional population-based statistical methods for haplotype determination are most problematic. The Human Leukocyte Antigen Loci (HLA) are examples of such regions. A combination of phased haplotype information was used for each family member and known tag haplotypes (de Bakker, P. I., et al. A high-resolution HLA and SNP haplotype map for disease association studies in the extended human MHC. Nat Genet 38, 1166-1172 (2006)) to estimate HLA type based on genotype for all four family members. A leave-one-out iterative search was performed using the phased haplotype information from each family member for the nearest common tag haplotype for HLA type, assigning the HLA type for each chromosome (paternal or maternal origin for the children, and contigs transmitted to one, both, or neither of the children in adults). This resulted in HLA types for each haploid chromosome 6 as displayed in FIGS. 2E and 2F.

Ancestry Analysis

Principle Components Analysis of Ancestry

To determine the ancestral origins for the quartet, principal components analysis (PCA) using the maternal and paternal genotypes and a subset of individuals of European ancestry was used from the Population Reference Sample (POPRES) data set. (Nelson, M. R., et al. The Population Reference Sample, POPRES: a resource for population, disease, and pharmacological genetics research. Am J Hum Genet 83, 347-358 (2008).) Briefly, maternal and paternal genotypes were combined with the genotypes from 10 individuals from Eastern/Southeastern Europe, 190 individuals from central Europe, 78 individuals from Northern/Northeastern Europe, 167 individuals from Northwestern Europe, 238 individuals from Southern Europe, 99 individuals from Southeastern Europe, 272 individuals from South-western Europe and 403 individuals from Western Europe (EuropeESE, EuropeC, EuropeNNE, EuropeNW, EuropeS, EuropeSE, EuropeSW, and EuropeW respectively in FIG. 3B). Next, PLINK was used to filter SNPs with greater than 10% missing data and a minor allele frequency less than 10%, and thinned 50-SNP windows to remove pairs of SNPs with an $R^2$ greater than 0.9. (Purcell, S., et al. PLINK: a tool set for whole-genome association and population-based linkage analyses. Am J Hum Genet 81, 559-575 (2007).) With the remaining 124,378 SNPs, EIGENSTRAT was used to perform a principal components analysis. (Price, A. L., et al. Principal components analysis corrects for stratification in genome-wide association studies. Nat Genet 38, 904-909 (2006).) Principle components one and two recapitulate the structure of continental Europe and reveal maternal and paternal ancestry to be North/Northeastern and Western European, respectively.

Rare and Novel Genetic Variant Risk Prediction

Definitions and Heuristic

The operational definition of a rare variant was a variant with an allele frequency of less than 5%. A hierarchical search was used for allele frequencies that first considered ethnicity-specific allele frequencies and then population-wide allele frequencies as follows:

1. Ethnicity-specific allele frequencies from the dbSNP 132 database
2. Ethnicity specific allele frequencies from the 1000 genomes pilot 1 data
3. Allele frequencies from the dbSNP 132 full database
4. Allele frequencies from the 1000 genomes full project data Dec. 13, 2010 release Alleles with an assigned rsid but no published allele frequency were considered rare but with no frequency data, and alleles not found in any published database were considered novel. This resulted in sets of 351,555 and 354,074 rare or novel variants from the HG19 and CEU reference variant call sets, respectively.

Figure 44:
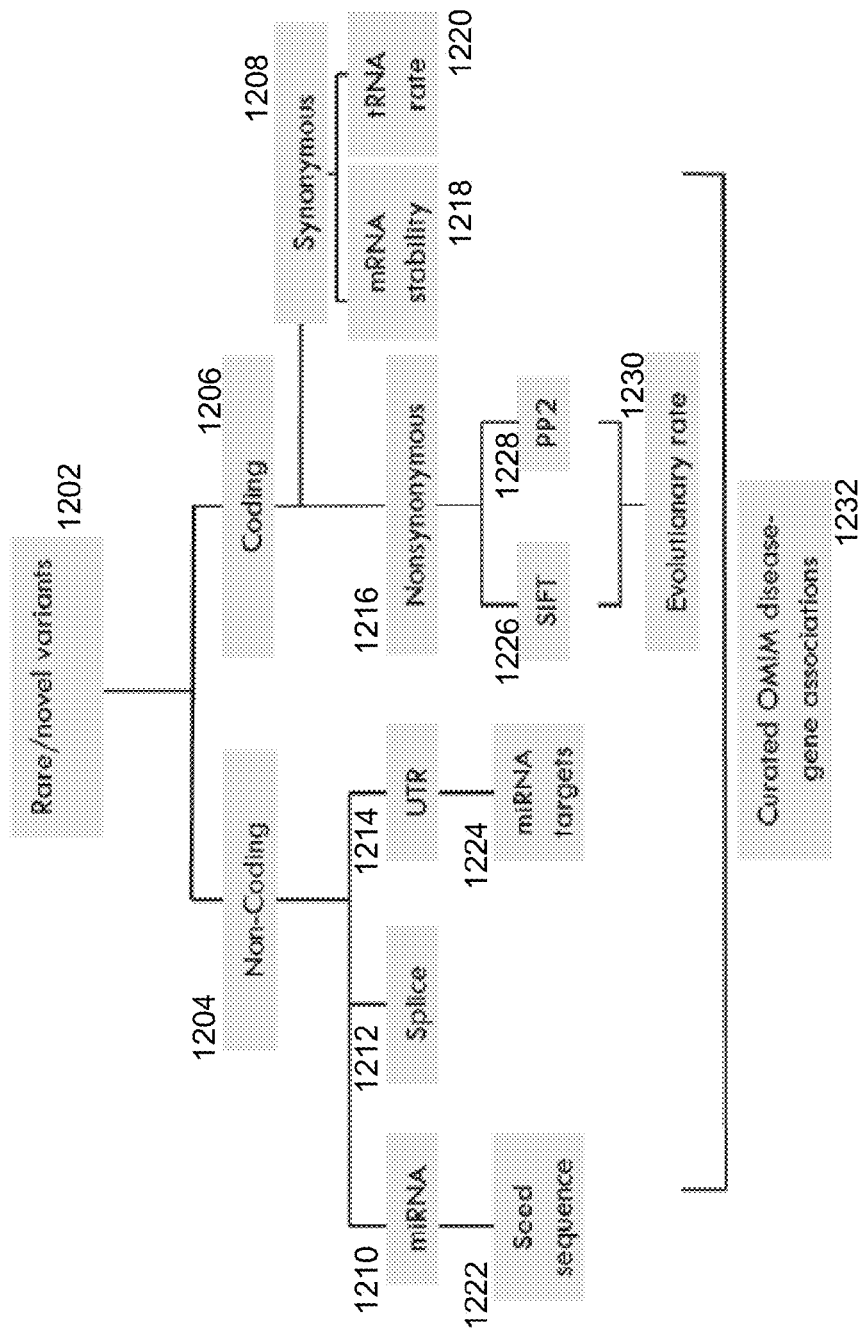
FIG. 44 is a chart illustrating a search heristic for rare and novel variants according to an embodiment of the present invention.

The overall heuristic for searching novel and rare variants for significant disease associations is presented in FIG. 44. The CCDS collection of coding sequence positions was used to assign rare and novel variants (step 1202) to coding and noncoding categories. Putative rare and novel loss of function variants (e.g., steps 1208-1230) were next annotated in coding (step 1204) and noncoding (step 1206) regions of genes known to be associated with Mendelian diseases as defined by the Online Mendelian Inheritance in Man database.

Shown in FIG. 44 is a search heuristic for rare and novel variants. Rare (allele frequency<5%) and novel variants (not found in dbSNP 132 or the august 2010 release of the 1000 genomes pilot data) were first identified (step 1202). The CCDS collection of coding sequences was used to assign rare and novel variants to coding (step 1204) and noncoding (step 1206) categories and annotated putative rare and novel loss of function variants in coding and noncoding regions of genes known to be associated with Mendelian diseases as defined by the Online Mendelian Inheritance in Man database. This list of variants was manually curated (step 1232) for association with known clinical syndromes and variant pathogenicity and phenotype information were scored as in Table 1 (FIG. 36).

Nonsynonymous Coding Variants

Non-synonymous variants (nsSNPs) were annotated using a combination of prediction algorithms and manual curation. All rare and novel variants were annotated using the Sorting Intolerant from Tolerate (SIFT) algorithm (see step 1226 of FIG. 44) developed by Henkoff, et al, which predicts the effects of non-synonymous polymorphisms on protein function based on homology, conservation, and physical properties of amino acid substitutions. (Ng, P. C. & Henikoff, S. SIFT: Predicting amino acid changes that affect protein function. Nucleic Acids Res 31, 3812-3814 (2003); Ng, P. C. & Henikoff, S. Predicting the effects of amino acid substitutions on protein function. Annu Rev Genomics Hum Genet 7, 61-80 (2006); Kumar, P., Henikoff, S. & Ng, P. C. Predicting the effects of coding non-synonymous variants on protein function using the SIFT algorithm. Nat Protoc 4, 1073-1081 (2009); Ng, P. C. & Henikoff, S. Accounting for human polymorphisms predicted to affect protein function. Genome Res 12, 436-446 (2002).) The Polymorphism Phenotyping (PolyPhen) 2 tool was used in parallel to annotate coding regions (see step 1228 of FIG. 44). (Adzhubei, I. A., et al. A method and server for predicting damaging missense mutations. Nat Methods 7, 248-249 (2010); Ramensky, V., Bork, P. & Sunyaev, S. Human non-synonymous SNPs: server and survey. Nucleic Acids Res 30, 3894-3900 (2002); Sunyaev, S. R., et al. PSIC: profile extraction from sequence alignments with position-specific counts of independent observations. Protein Eng 12, 387-394 (1999).) This algorithm is a probabilistic classifier that predicts the impact of amino acid changes on protein function using an algorithm that incorporates information on site of substitution (whether an amino acid change occurs in one of several sites of functional importance such as binding sites or trans-membrane regions), multiple sequence alignment, and known protein structural changes. For this analysis, the human variation trained data was used, which is based on known damaging alleles involved in Mendelian diseases and multiple sequence alignment with closely related mammalian homologs. In an embodiment of the present invention, this training set showed improved performance for distinguishing variants with severe effects from more abundant, mildly deleterious variants.

Because the prediction accuracies of SIFT and PolyPhen have been shown to depend heavily on the evolutionary anatomy of genomic position at which an nsSNP occurs (Kumar, S., et al. Positional conservation and amino acids shape the correct diagnosis and population frequencies of benign and damaging personal amino acid mutations. Genome Res 19, 1562-1569 (2009)), nsSNPs were further annotated using position-specific evolutionary features derived from a 46 species multiple sequence alignment (MSA) of vertebrate genomes obtained from the UCSC Genome Browser (http://genome.ucsc.edu/; Accessed Nov. 30, 2010). For each genomic position, the evolutionary rate (mutations per billion years) was computed (see step 1232 of FIG. 44) across the mammalian lineage using the method previously described by Fitch (Fitch, W. Toward Defining the Course of Evolution: Minimum Change for a Specific Tree Topology. Systematic Zoology 20, 406-416 (1971)), and also computed the evolutionary time-span (ETS) as the proportion of non-gap sequences in the MSA at a position. For coding variants of unknown significance, the mammalian evolutionary rate is proportional to the fraction of selectively neutral alleles at a position (Kimura, M. Evolutionary rate at the molecular level. Nature 217, 624-626 (1968)), and can therefore serve as a prior expectation in determining the likelihood that an observed nsSNP is deleterious. In general, SNVs found at positions having a mammalian evolutionary rates>1 are not likely to be associated with deleterious protein sequence changes (Kumar, S., et al. Positional conservation and amino acids shape the correct diagnosis and population frequencies of benign and damaging personal amino acid mutations. Genome Res 19, 1562-1569 (2009)), and SNVs with evolutionary rates>2 are highly unlikely to be deleterious, as most "neutral" population variation characterized by HapMap and other population samples lie in this range. Consequently, the prediction accuracies of SIFT and PolyPhen are substantially reduced at positions having an evolutionary rate>1.

In order to prioritize the evaluation and delivery of information relating to the rare and novel variants, a rating schema was developed and applied that was based on phenotype-level information about the variants in Mendelian-disease associated genes and predicted or experimentally derived variant pathogenicity. This rating schema is summarized in Table 5 (FIG. 46). Of 200 novel or rare non-synonymous variants coding variants associated with OMIM-disease genes, 72 were in genes known to be associated with plausible Mendelian diseases. These variants were manually curated according to this rating schema using a combination of private and public mutation database data including the Human Gene Mutation Database, dbSNP, Entrez Gene, and disease specific databases with follow up review of the primary literature when available. Of these 72 manually curated variants, five were associated with known disease phenotypes. The remaining 67 variants were of unknown significance and were rated according to predicted pathogenicity, disease phenotype, and position-specific rates and the evolutionary time span and are displayed in Table 6 (FIG. 47).

The children were compound heterozygous for variants in four disease-related genes: BLM (mother, son and daughter), associated with Bloom syndrome, MLH3 (son), associated with familial non-polyposis colon cancer, SLC4A5 (son), associated with proximal renal tubular acidosis, and COG7 (daughter), associated with type IIe congenital disorder of glycosylation. There were two instances of homozygosity for rare/novel variants in disease-related genes in the daughter (KRT8, associated with monilethrix, and ASAH1, associated with Farber lipogranulomatosis) and one such instance in the son (PLEC1, associated with epidermolysis bullosa simplex, Table 7 (FIG. 48)). With the exception of hereditary non-polyposis colon cancer (HNPCC), all of these conditions present in infancy or early childhood and, therefore, the lack of associated trait phenotypes brings into question the associated variant-level pathogenicity. One of the MLH3 variants is predicted to be benign by both prediction algorithms and has a high evolutionary rate, providing further evidence that it is likely a benign, albeit rare, polymorphism. The other variant in MLH3 has no known clinical association is described as a "natural variant" the UniProt database, and is predicted to be tolerated by SIFT but possibly damaging by PolyPhen2, and has a low evolutionary rate. It is unclear what role these variants may play in predisposition to HNPCC, but the lack of any of the major criteria for diagnosis of this autosomal dominant condition (Vasen, H. F., Watson, P., Mecklin, J. P. & Lynch, H. T. New clinical criteria for hereditary nonpolyposis colorectal cancer (HNPCC, Lynch syndrome) proposed by the International Collaborative group on HNPCC. Gastroenterology 116, 1453-1456 (1999)) suggests that they are not likely to be causative for HNPCC.

Synonymous Coding Variant Risk Prediction

Figure 45:
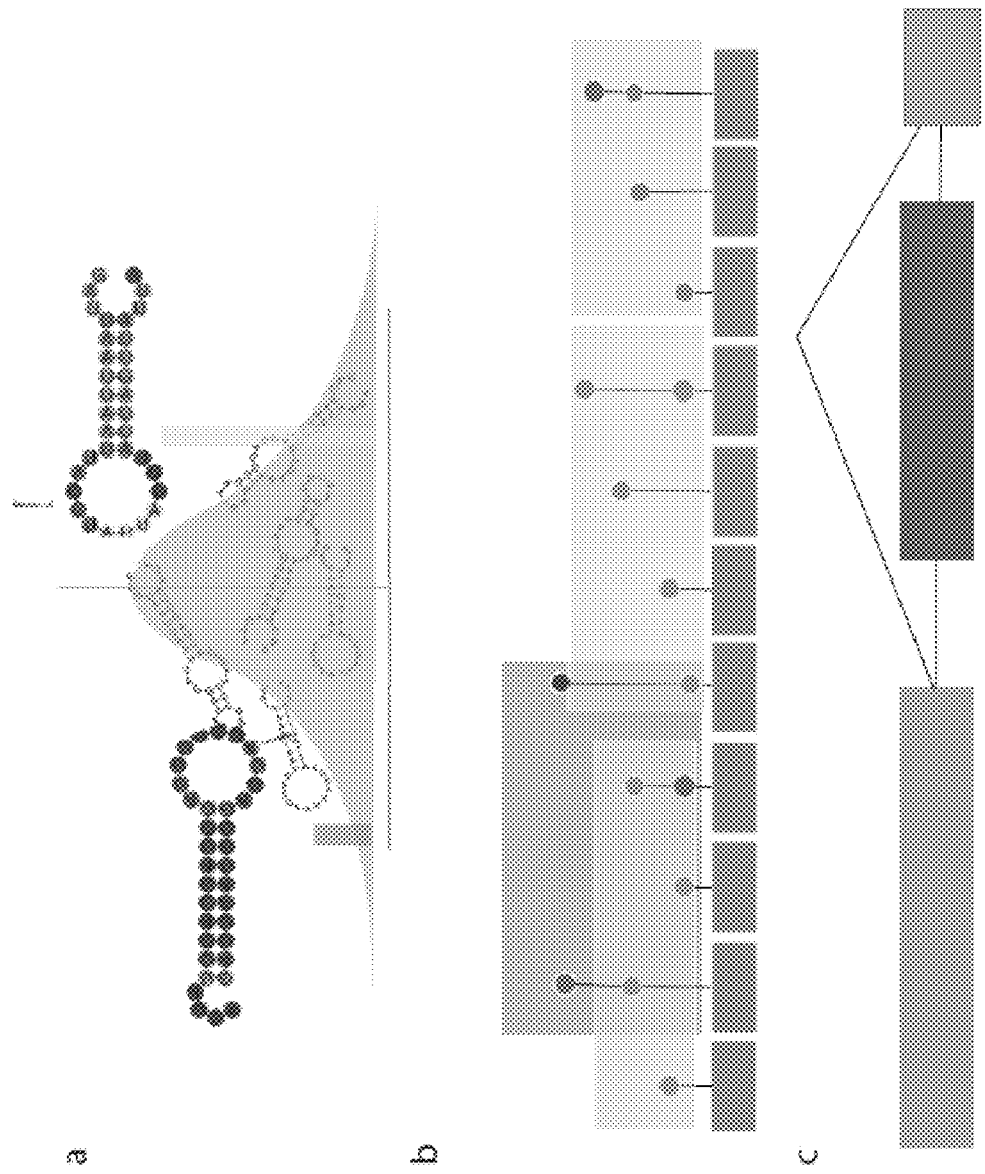
FIGS. 45A-45C illustrate three models for the association between a synonymous SNPs gene function according to an embodiment of the present invention.

Apart from amino-acid substitutions, there are several ways that synonymous single nucleotide polymorphisms (sSNPs) can affect a gene and its resulting protein products. Alteration of splice sites can modify how a gene is spliced and result in important changes in the resulting mRNAs; most of these alterations result in premature mRNA degradation. Creation of spurious splice sites may affect the resulting protein sequence. Other factors that affect protein production and structure include mRNA decay rates and mRNA structural motifs surrounding important regulatory sites (such as 5' and 3' UTRs). Finally, codon usage bias can have a direct effect on protein elongation and translational kinetics, a consequence of the correlation between codon usage frequency and tRNA availability. This leaves three main mechanisms that can be computationally explored to detect putative phenotypic changes provoked by sSNPs (See FIG. 45).

Three models for the association between a synonymous SNPs gene function were developed. FIG. 45A shows shifts in signal to noise ratios between energies of a window of nucleotides that surround the SNP locus. The random background model is generated as sequences that have identical nucleotide composition except for a small interval that contains the SNP locus, thus measuring the contribution of the reference and polymorphic nucleotide to mRNA free energy, which is used as a proxy of mRNA stability. Codon usage frequencies correlate with ribosome latency and have been shown to affect, sometimes dramatically, protein elongation dynamics as shown in FIG. 45D. Codons are clustered based on their position and usage frequencies, in both the reference and SNP-containing transcript. Changes in cluster centroids are given as a measure of local influences of codon frequency changes to global codon usage structure. As shown in FIG. 45C, splicing site generation or disruption is measured as the change in predicted odds ratio of the maximum entropy splicing model of Yeo and Burgue. All synonymous SNPs were analyzed using these three criteria.

Aberrant splicing is a phenomenon that has been linked to synonymous mutations in various studies. Creation and disruption of 5' donor splice sites and exonic splice site enhancers through synonymous alterations have been reported to be part of the etiology of diseases such as type 1 neurofibromatosis, multiple sclerosis, and phenylketonuria. (Chamary, J. V., Parmley, J. L. & Hurst, L. D. Hearing silence: non-neutral evolution at synonymous sites in mammals. Nat Rev Genet 7, 98-108 (2006); Kimchi-Sarfaty, C., et al. A "silent" polymorphism in the MDR1 gene changes substrate specificity. Science 315, 525-528 (2007).) Splice site prediction algorithms exist and are primarily used for genome-wide gene detection of splice sites. However, they can also be used to detect putative disruption or creation of splicing sites in a simplistic fashion by comparing predictions when applying the algorithm to reference and the variant DNA sequences. Using this criteria, the maximum entropy splice site detection algorithm (Yeo, G. & Burge, C. B. Maximum entropy modeling of short sequence motifs with applications to RNA splicing signals. J Comput Biol 11, 377-394 (2004)) was applied to the flanking sequence of a sSNP with and without the polymorphic substitution. Predictions resulting in a positive odds ratio for the reference sequence but in a negative odds ratio for the sequence with the polymorphism are flagged as putative splice site disruptions. Conversely, a combination of a negative prediction for the reference sequence and a positive score for the SNP-affected sequence is reported as putative creation of a splice site.

Several mRNA structural factors are associated with important effects on phenotype. Secondary structure may directly affect mRNA decay rates as well as confer protection from premature degradation. Furthermore, highly structured UTRs can prevent regulatory molecules, such as microRNAs, from performing proper regulatory functions. Thus, investigating the effects of sSNPs in mRNA structure becomes a great pivotal point to indirectly study putative changes in the resulting protein. A small set of articles have already laid ground on the case, by analyzing the influence of sSNPs in mRNA secondary structure and its effects on mRNA stability and decay.

RNA secondary structure prediction is a classical problem in computational biology and there are many methods that give reasonable estimates. Most of them report the resulting free energy, ΔG, of the predicted secondary structure, thereby giving a thermodynamic measure of structure. Algorithms for detecting non-coding RNAs use free energy along with other heuristics to detect putative biologically active transcripts. (Rivas, E. & Eddy, S. R. Secondary structure alone is generally not statistically significant for the detection of noncoding RNAs. Bioinformatics 16, 583-605 (2000).) In particular, these algorithms attempt to find a 'structural signal' in a certain window of nucleotides while scanning a genome. One approach to do this is by performing free energy calculations for randomized samples of the same size and monomeric or dimeric conformations than that of the current window. A Z-score is then given to the window, defined as:

$$Zscore(G; \text{seq}) = \frac{G(\text{seq}) - G_\mu(\text{seq}, S)}{G_\sigma(\text{seq}, S)} \quad (2)$$

where G(seq) is the free energy of the RNA sequence seq, $G_\mu$(seq,S) is the average free energy of the sequences of the sample set S that have the same length and monomeric (or dimeric, if desired) conformation than seq, and $G_\sigma$ (seq,S) is the standard deviation of the free energies. There has been evidence demonstrating that secondary structure by itself does not give a strong signal from random sequences with the same monomer or even dimer conformations. (Rivas, E. & Eddy, S. R. Secondary structure alone is generally not statistically significant for the detection of noncoding RNAs. Bioinformatics 16, 583-605 (2000).) This is reasonable since permutation of nucleotides is a far more benign alteration than deletion, insertion, or replacement. To express this in the Z-score, the definition of the sample set is modified to a set of random sequences of the same length of the window but not necessarily with the same n-meric conformation.

To apply the Z-score notion to probe if a change in secondary structure occurs with a SNP, the structural significance of the subsequence flanking the SNP was assessed. This was done by taking two windows: the flanking window, $W_f$, and the sampling window, $W_s$. The flanking window is the sequence that contains the SNP position in its midpoint. The sampling window is a subsequence of the flanking window and also contains the SNP position. The sampling is then performed from the set $S(W_f,W_s)$ of sequences with length of the flanking window that vary only in the sampling window. Finally the Z-score, as defined previously in equation 3, is taken using this sample set:

$$Zscore(G; \text{seq}) = \frac{G(\text{seq}) - G_\mu(\text{seq}, S(W_f, W_s))}{G_\sigma(\text{seq}, S(W_f, W_s))} \quad (3)$$

This is done using the ViennaRNA folding package. (Hofacker, I. L. Vienna RNA secondary structure server. Nucleic Acids Res 31, 3429-3431 (2003).) The Z-score of the reference sequence is then compared with the Z-score of the sequence containing the SNP substitution and obtain a difference score. This score expresses the difference between structural importance of the sequence in the sampling window in the reference and SNP-containing sequence.

Two genes that code for the same protein using synonymous codons do not necessarily give the same result. This is mainly due to the fact that tRNA iso-acceptors do not have equal abundance in the cell. Even though this statement was confirmed in vitro several years ago, only recently has such a situation been observed as occurring in vivo. The demonstration that codon usage bias can alter translational kinetics opens an interesting new venue to search for relations between phenotype alterations and sSNPs. Codon usage bias analysis is not new, and has been fairly well studied since the beginning of the genomic era. (Eyre-Walker, A. C. An analysis of codon usage in mammals: selection or mutation bias? J Mol Evol 33, 442-449 (1991); Ikemura, T. Codon usage and tRNA content in unicellular and multicellular organisms. Mol Biol Evol 2, 13-34 (1985).) Several results confirm that, in some organisms, codon usage is also related with position, since it is not rare to see codons with similar relative frequency (relative frequency is the frequency of a codon occurring in a genome with respect to codons that code for the same amino-acid while absolute frequency is the frequency of codon occurrence with respect to the set of all codons) cluster together in particular sites. (Eyre-Walker, A. C. An analysis of codon usage in mammals: selection or mutation bias? J Mol Evol 33, 442-449 (1991); Zhang, G. & Ignatova, Z. Generic algorithm to predict the speed of translational elongation: implications for protein biogenesis. PLoS One 4, e5036 (2009).) This has led to the speculation that codon choice is directed by evolution, given that there could be selection constraints acting in some aspects of translational kinetics, such as protein elongation. Following this conceptualization, changes in codon bias via a clustering criterion are assessed.

Given an exon sequence seq, a set of pairs is first produced:

$$C_i(\text{seq}) = \left\{ \left( \frac{N_{norm}}{N, \text{rel}_n} \right) \right\}$$

for all possible n in seq, where n is the $n^{th}$ codon in the sequence given the $i^{th}$ open reading frame, N is the total number of codons in the sequence, and $\text{rel}_n$ is the relative frequency of the $n^{th}$ codon. The k-means clustering algorithm is then applied to $C_i$(seq) for each open reading frame (ORF) with a given k. This is performed with both the reference and SNP-modified sequence, SNPseq. Finally, for all ORFs, the resulting centroids are compared between both sequences and the sum of their distances is computed, taking the minimum of these values. In other words, the final codon usage score is:

$$CU = \min_i (\Sigma \text{dist}(C_{k,i}(seq), C_{k,i}(SNP\text{seq}))) \quad (4)$$

where $C_k,i$ is the set of k centroids in the $i^{th}$ ORF.

Noncoding Variant Risk Prediction

A search was conduced for rare and novel variants in noncoding regions associated with introns, 3' and 5' UTRs, and miRNA target regions in 3' UTRs of genes associated with Mendelian disorders as well as pre-miRNA and mature miRNA sequences targeting genes associated with Mendelian disorders. miRNA target regions and sequence coordinates were obtained from the miRbase database. As a supplement to the maximum entropy splice site disruption algorithm described above, a search was also conducted for known splice donor and acceptor sites for rare and novel variants. Rare and novel variants in pre-miRNA, mature miRNA, miRNA target regions, and splice sites were annotated as putative loss of function variants.

Structural Variant Risk Prediction

Indels were annotated based on their rarity (with allele frequencies derived from the 1000 genomes pilot 1 data), association with coding regions, whether they disrupted a splice site, and whether they were predicted to cause a frame-shift in an open reading frame. As allele frequencies for indels are less reliable than for single nucleotide variants, novel frameshift indels in coding regions or novel indels in splice sites of genes associated with OMIM-curated diseases were considered to be loss of function variants. There were 27 such variants when compared to the HG19 reference genome and 29 such variants when compared to the CEU major allele reference genome.

Common Genetic Variant Risk Prediction

Quantitative Disease-SNP Association Database

As described previously, quantitative human disease-SNP associations were manually curated from the full text, figures, tables, and supplemental materials of 4,022 human genetics papers. (Ashley, E. A., et al. Clinical assessment incorporating a personal genome. Lancet 375, 1525-1535 (2010).) Also, more than 100 features were recorded from each paper, including the disease name (e.g. coronary artery disease), specific phenotype (e.g. acute coronary syndrome in coronary artery disease), study population (e.g. Finnish individuals), case and control population (e.g. 2,508 subjects with coronary artery disease proven by angiography), gender distribution, genotyping technology, major/minor risk alleles, odds ratio, 95% confidence interval of the odds ratio, published p-value, and genetic model. Studies on similar diseases were categorized and mapped to the Concept Unique Identifiers (CUI) in the Unified Medical Language System (UMLS). (Bodenreider, O. The Unified Medical Language System (UMLS): integrating biomedical terminology. Nucleic Acids Res 32, D267-270 (2004)) For each study, the frequency of each genotype and allele in the case and control populations was recorded. Strand ambiguities were resolved with an automatic strand detection algorithm described previously.

Calculation of Predicted Personal Genetic Risk for 28 Common Diseases

For each of 28 common diseases, all SNPs that had been significantly associated with the disease with a p-value of $\leq 10^{-6}$ in two or more Genome-Wide Association Studies (GWAS) with a total sample size of 2,000 or more subjects were identified. Genetic risk was estimated using a likelihood ratio for each SNP defined by the relative frequency of the individual's genotype in the diseased vs. healthy control populations (e.g., given an allele "A", $LR=Pr(A|diseased)/Pr(A|control)$). The LR incorporates both the sensitivity and specificity of the test and provides a direct estimate of how much a test result will change the odds of having a disease. (Morgan, A. A., Chen, R. & Butte, A. J. Likelihood ratios for genome medicine. Genome Med 2, 30 (2010).) Studies with diseased subjects in the control group and studies on non-Caucasian populations were excluded. For each SNP, the LRs from multiple studies were averaged with a weight of the square root of the sample size to give higher confidence to studies with larger sample size. After removing SNPs in linkage disequilibrium ($R^2 \geq 0.3$ in the corresponding population group), each locus was assumed as an independent genetic test and LRs were multiplied to report the summarized score or predicted genetic risk. Pre- and post-test estimates of disease risk were calculated (see step 160 of FIG. 1C) for the father using age and sex-matched cohorts for estimation of pre-genotype disease risk and the composite likelihood rations for post-genotype disease risk.

Calculation of Relative Population Based Disease Risk

To evaluate the relative population based disease risk, the personal genetic risk was calculated on 58 diseases for 174 CEU individuals from the HapMap project version II and III (see FIGS. 4-31). Only SNPs that were genotyped in both CEU and the family quartet were included. The disease risk percentile score was calculated as the percentage of CEU individuals who have a lower risk than the subject in question.

Family Differential Risk and Parental Contribution to Common Disease Risk

The disease risk for each of the family members was calculated according to phased SNP genotypes as described above; this information is displayed in FIGS. 32-35. For the daughter and son, the paternal and maternal disease risk allele contribution was calculated according to likelihood ratios from phased variant genotypes at each SNP locus, generating an estimate of paternal and maternal haplotype disease risk contribution in each child (FIGS. 32-35).

Pharmacogenomics

Pharmacogenomics Knowledge Base

Genome-wide pharmacogenomic associations were annotated using the Pharmacogenomics Knowledge Base (www.pharmgkb.org), an online pharmacogenomics resource containing manually created annotations on a large collection of pharmacogenomics literature. Over 1400 drug-variant-phenotype relationships were curated from the literature and these relationships were used to create clinical annotations for 298 known variants (see step 162 of FIG. 1C). Some variants have more than one clinical annotation to represent different drug-phenotype relationships.

All primary annotations referring to the same drug-variant-phenotype association were combined into one summary for each clinical annotation in the database. For example, the relationship between the TPMT*3B variant (rs1800460) and adverse reactions to purine analogs has been studied for years and published multiple times. These combined clinical annotations were then linked to the PMIDs of citations that were used to create the annotation, creating a written summary for each possible genotype. Using the same TPMT example, the AA genotype contains 2 copies of the *3B variant and is associated with significantly increased risk of side effects due to decreased enzyme levels; the AG genotype contains 1 copy of the *3B variant and is associated with slightly increased risk of side effects due to moderately decreased enzyme levels; and the GG genotype contains no copies of the *3B variant and is not associated with increased risk of side effects. The level of risk for any given genotype is written with respect to the risk for other genotypes. Thus, the AA genotype is associated with increased risk of side effects as compared to the AG and GG genotypes, but not necessarily at increased risk of side effects for patients on the drug in general. Risk relative to other genotypes is used because the incidence of efficacy or adverse events for any given drug has usually not been quantified. Also, the typical genotype for any given population can be difficult to determine. Although many groups use HapMap frequencies to calculate population major alleles or typical genotypes, the HapMap populations are small and ethnically very specific. Their frequencies do not necessarily represent larger population frequencies (nor were they meant for such purpose). Therefore, no attempt is made to state what the risk of any given drug reaction is compared to "normal," since normal is not defined, but rather the risk is reported as compared to other possible genotypes.

A "Strength of evidence" score is then assigned to each clinical annotation and this score is used as a measure of confidence in the association. This strength of evidence score is based on several criteria, including independent replication of the association, population size of the studies and p-value of the association (after correction for multiple hypothesis testing, if applicable). A score of high confidence was assigned if the association has been replicated in populations of at least 1000 cases and 1000 controls of the same ethnicity with p-values>0.05 after correction. A score of medium confidence required p-values<0.05 after correction and at least one population studied of at least 100 people, with or without further replication. Finally, a low confidence score was assigned to all clinical annotations that did not meet the criteria for high or medium confidence scores, including those annotations where all evidence of the association is based on in vitro studies or pharmacokinetic data alone.

Variant Level Annotation

Drug-variant phenotypes can be very complicated and specific to certain patient populations. For simplicity and illustration purposes, clinical annotations were binned into the following groups in an embodiment of the present invention: Drug(s) More Likely to Work, Drug(s) Less Likely to Work, Drug(s) More Likely to Cause Side Effect, Drug(s) Less Likely to Cause Side Effect, Drug Dose(s) Easy to Predict, Drug Dose(s) Difficult to Predict, Drug Dose(s) Above Average, Drug Dose(s) Below Average, No Pharmacogenomic Action and/or Phenotype Unknown and/or Phenotype Not Applicable (example: ovarian cancer risk for males). An example annotation is given in Table 8 (FIG. 49) and full annotations for the study subjects are provided in Tables 9-11 (FIGS. 50-52).

Exemplary Results

Development of Ethnicity Specific Major Allele References

In an embodiment of the present invention, three ethnicity-specific major allele references were developed for the CEU, YRI, and CHB/JPT HapMap population groups using estimated allele frequency data at 7,917,426, 10,903,690, and 6,253,467 positions cataloged in the 1000 genomes project. Though relatively insensitive for very rare genetic variation, the low coverage pilot sequencing data (which comprises the majority of population-specific variation data) has a sensitivity for an alternative allele of >99% at allele frequencies>10% and, thus, has high sensitivity for detecting the major allele. In an embodiment, substitution of the ethnicity-specific major allele for the reference base resulted in single base substitutions at 1,543,755, 1,658,360, and 1,676,213 positions in the CEU, YRI, and CHB/JPT populations, respectively. There were 796,548 positions common to all three HapMap population groups at which the major allele differed from the NCBI reference base (see FIG. 1A). Variation from the NCBI reference genomes was relatively uniform across chromosomal locations with the exception of loci in and near the Human Leukocyte Antigen loci on chromosome 6 (see FIG. 1B).

FIGS. 1A-1C show the development of major allele reference sequences and genetic risk prediction workflow according to embodiments of the present invention. In an embodiment, allele frequencies from the low coverage whole genome sequencing pilot of the 1000 genomes data were used to estimate the major allele for each of the three main HapMap populations. The major allele was substituted for the NCBI reference sequence 37.1 reference base at every position at which the reference base differed from the major allele, resulting in approximately 1.6 million single nucleotide substitutions in the reference sequence. As shown in FIG. 1A, approximately half of these positions were shared between all three HapMap population groups, with the YRI population containing the greatest number of major alleles differing from the NCBI reference sequence. FIG. 1B shows the number of positions per Mbp at which the major allele differed from the reference base by chromosome and HapMap population. The proportion of alleles differing from the NCBI reference sequence differed most in the positions surrounding the Human Leukocyte Antigen (HLA) loci on chromosome 6. FIG. 1C is a workflow diagram for phased genetic risk evaluation using whole genome sequencing according to an embodiment of the present invention.

Study Subjects and Genome Sequence Generation

Clinical characteristics of study subjects are described in graphical form in the pedigree shown in FIG. 2A. Two first-degree family members, including the father in the sequenced quartet, have a history of venous thrombosis (e.g., DVT as shown in FIG. 2A); notably, the sequenced father has a history of recurrent venous thromboembolism (e.g., VTE as shown in FIG. 2A) despite systemic anticoagulation. Both parents self-reported northern European ancestry. As shown, ages represent age of death for deceased subjects or the age at the time of medical history collection in 2010 for living family members. Arrows denote sequenced family members. Abbreviations are as follows: AD, Alzheimer's disease; CABG, coronary artery bypass graft surgery; CHF, congestive heart failure; CVA, cerebrovascular accident; DM, diabetes mellitus; DVT, deep venous thrombosis; GERD, gastroesophageal reflux disease; HTN, hypertension; IDDM, insulin-dependent diabetes mellitus; MI, myocardial infarction; SAB, spontaneous abortion; SCD, sudden cardiac death.

The Illumina sequencing platform was used to provide 39.3× average coverage of 92% of known chromosomal positions in all four family members (See FIGS. 41A and 41B). Variants were identified by comparison with the HG19 reference as well the CEU major allele reference that were developed, resulting in single nucleotide substitutions at an average distance of 699 base pairs when compared with the NCBI reference and 809 base pairs when compared with the CEU major allele reference. 859,870 indels were identified at an average inter-marker distance of 3.6 kbp.

Inheritance State Analysis Identifies >90% of Sequencing Errors

Sequencing family quartets allows for precise identification of meiotic crossover sites from boundaries between inheritance states and superior error control. (Roach, J. C., et al. Analysis of genetic inheritance in a family quartet by whole-genome sequencing. Science 328, 636-639 (2010).) Contiguous blocks of single nucleotide variants were resolved into one of four Mendelian inheritance states or two error states. Using this methodology, 3.1% of variant positions were identified as associated with error prone regions (see FIG. 2B).

Figure 2B:
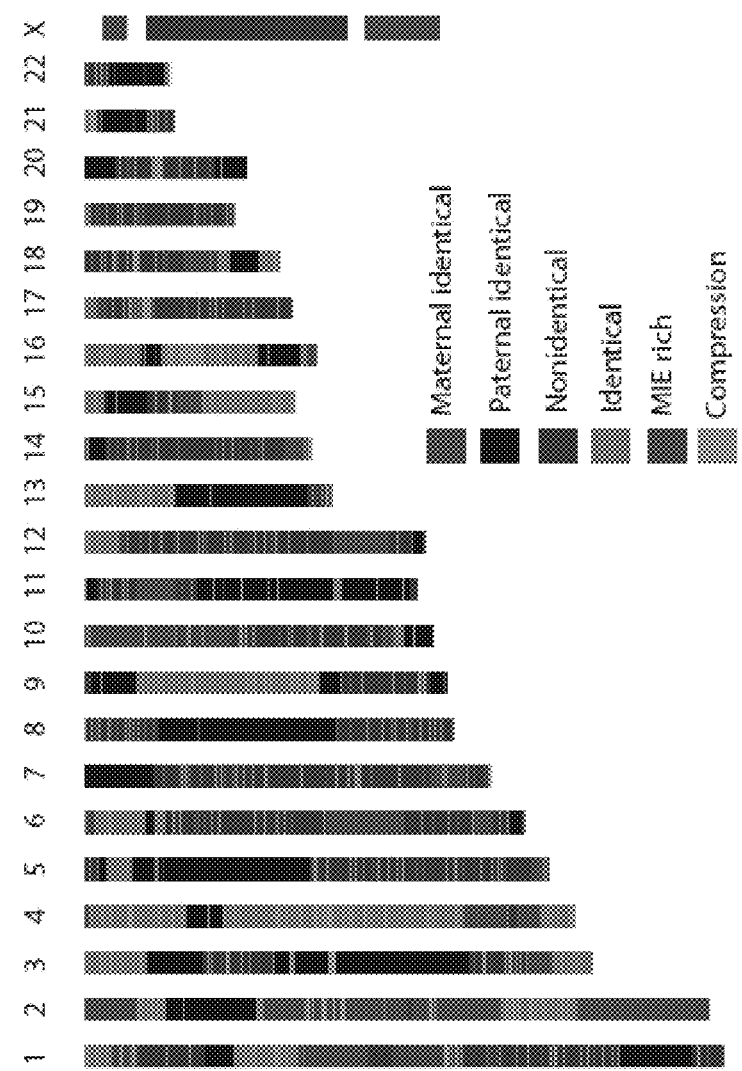
FIG. 2B illustrates the manner in which a Hidden Markov Model (HMM) was used to infer one of four Mendelian and two non-Mendelian inheritance states for each allele assortment at positions variant across the quartet according to an embodiment of the present invention.

FIG. 2B shows the manner in which a Hidden Markov Model (HMM) was used to infer one of four Mendelian and two non-Mendelian inheritance states for each allele assortment at positions variant across the quartet. "MIE-rich" refers to Mendelian-inheritance error (MIE) prone regions due to sequencing or assembly errors. "Compression" refers to genotype errors from hemizygous structural variation in the reference or study subjects, resulting in a high proportion of uniformly heterozygous positions across the quartet.

Using a combination of these methods and quality score calibration with orthogonal genotyping technology, 94% of genotyping errors (see FIG. 2C) were identified, with the greatest reduction in error rate resulting from filtering of variants in error prone regions. A final genotype error rate was estimated by three methods of between $5.26 \times 10^{-7}$, estimated by the state consistency error rate in identical-by-descent regions, and $2.1 \times 10^{-6}$, estimated by the MIE rate per by sequenced. FIG. 2C is a plot of a combination of quality score calibration using orthogonal genotyping technology and filtering SNVs in error prone regions (MIE-rich and compression regions) identified by the HMM resulted in >90% reduction in the genotype error rate estimated by the MIE rate per 10 mega bases (Mbp).

Figure 2D:
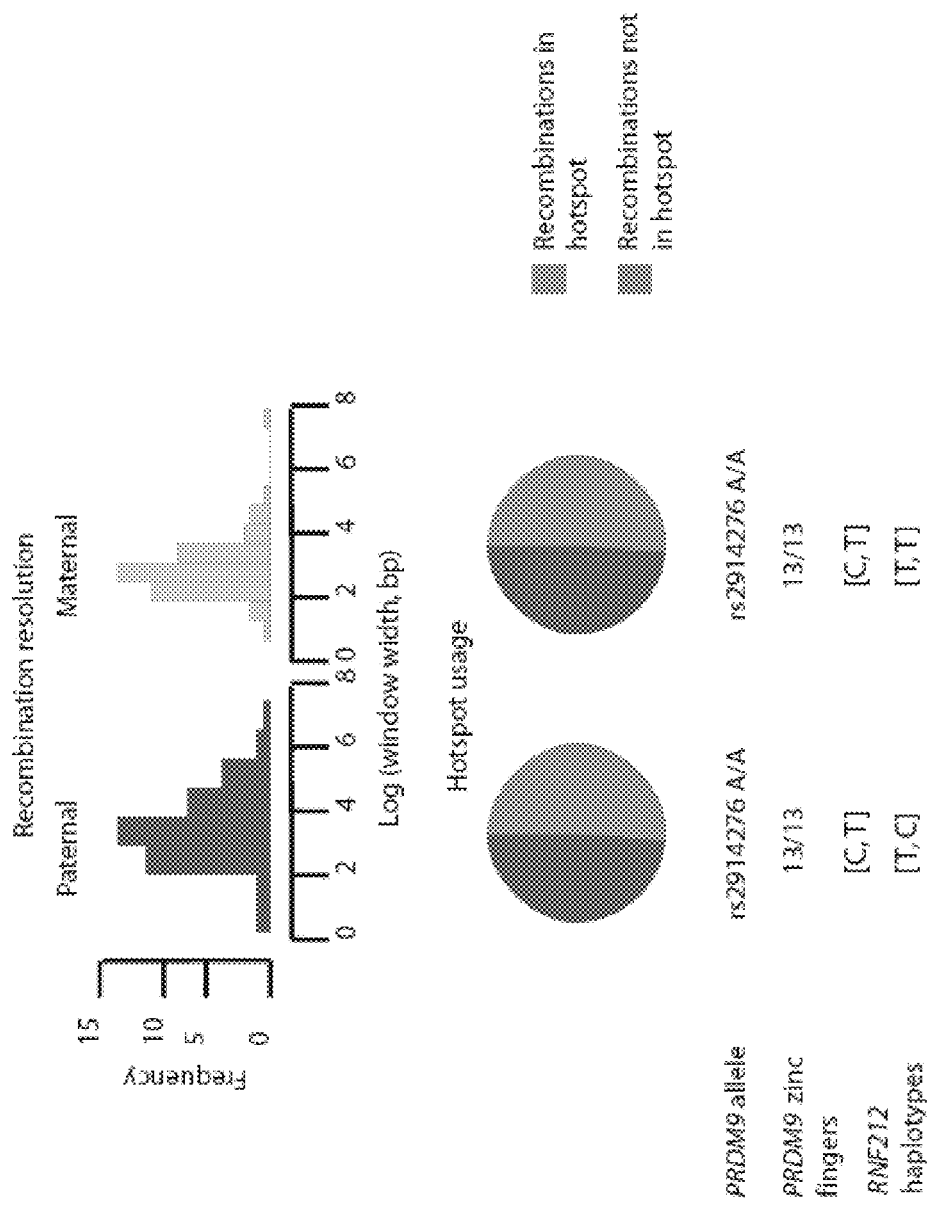
FIG. 2D illustrates the manner in which, consistent with PRDM9 allelic status, approximately half of all recombinations in each parent occurred in hotspots.

Consistent with PRDM9 allelic status, approximately half of all recombinations in each parent occurred in hotspots as shown in FIG. 2D. The mother has two haplotypes in the gene RNF212 associated with low recombination rates, while the father has one haplotype each associated with high and low recombination rates, potentially accounting for nearly equal recombination male and female recombination number. Notation denotes base at [rs3796619, rs1670533].

RNF212 Haplotypes Predict Nearly Equal Male and Female Recombination Frequency

Boundaries between contiguous inheritance state blocks defined 55 maternal and 51 paternal recombination events across the quartet at a median resolution of 963 base pairs. A parallel heuristic analysis of recombination sites confirmed the observation of nearly equal paternal and maternal recombination frequency. Two SNPs (rs3796619 and rs1670533), separated by 17 kb in the gene RNF212, form a haplotype that is significantly associated with genome wide recombination rate in a sex-specific manner, such that the haplotype associated with the highest recombination rate in males is associated with a low female recombination rate. (Kong, A., et al. Sequence variants in the RNF212 gene associate with genome-wide recombination rate. Science 319, 1398-1401 (2008).) Fine scale recombination mapping (see step 158 of FIG. 1C) and long range phasing revealed that the mother has two haplotypes ([C, T] and [T, T]) associated with low recombination rates in females, while the father has one haplotype associated with low recombination rate in males [T, C]. The father also has the common [C,T] haplotype which is notably associated with high recombination rates in males when compared with the other two observed haplotypes. These haplotype combinations likely contribute to below average recombination rate in the mother and average recombination rate in the father.

PRDM9 Allelic Status Predicts High Hotspot Usage

Several loci in the vicinity of the PRDM9 gene are associated with recombination hotspot usage. (Baudat, F., et al. PRDM9 is a major determinant of meiotic recombination hotspots in humans and mice. Science 327, 836-840 (2010); 8. (Myers, S., et al. Drive against hotspot motifs in primates implicates the PRDM9 gene in meiotic recombination. Science 327, 876-879 (2010); Parvanov, E. D., Petkov, P. M. & Paigen, K. Prdm9 controls activation of mammalian recombination hotspots. Science 327, 835 (2010); Kong, A., et al. Fine-scale recombination rate differences between sexes, populations and individuals. Nature 467, 1099-1103 (2010).) The heritability for hotspot use explained by this locus is among the highest of all described quantitative trait loci and is determined by both single nucleotide substitutions in and near PRDM9 and the number of zinc finger α-helices in exon 12 of the gene. (Kong, A., et al. Fine-scale recombination rate differences between sexes, populations and individuals. Nature 467, 1099-1103 (2010).) The use of whole genome sequencing allows for fine mapping of these sites and investigation of the relationship between PRDM9 haplotypes and hotspot usage. Of the SNPs near PRDM9, rs2914276 is most significantly associated with hotspot usage heritability. In this quartet, both parents are homozygous for the rs2914276-A allele that is associated with high hotspot usage as well as the number of zinc finger repeats in PRDM9. (Kong, A., et al. Fine-scale recombination rate differences between sexes, populations and individuals. Nature 467, 1099-1103 (2010).) Zinc finger repeat number ranges between 12 and 16 in population studies; both parents carry 13 zinc finger repeats in the PRDM9. Consistent with previous population-wide observations for individuals with this combination of rs2914276 alleles and number of zinc finger repeats, it was found that 25 of 51 paternal recombination windows (49%) and 27 of 55 maternal recombination windows (49%) were in hotspots (defined by maximum recombination rate of >10 cM/Mbp), while only ~4 (4.1%) would be expected by chance alone ($p=2.0 \times 10^{-73}$ for hotspot enrichment according to Monte Carlo permutation).

Figure 42:
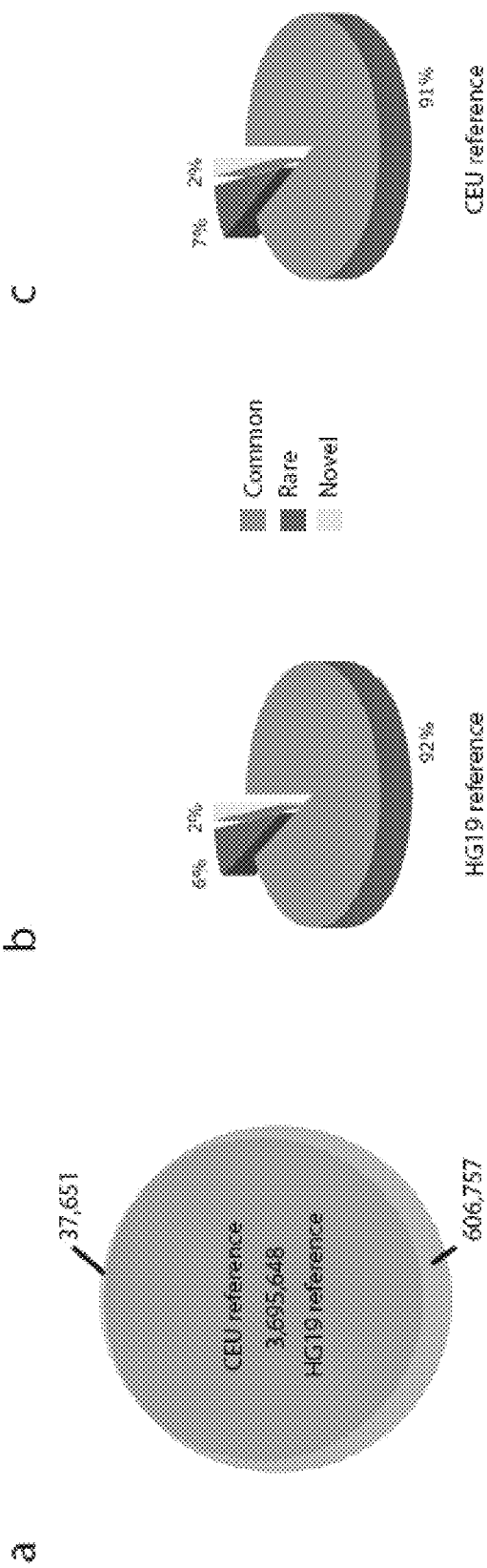
FIGS. 42A-42C are plots of variant types and error rate estimates for variants against NCBI reference 37.1 and CEU major allele reference according to an embodiment of the present invention.

Prior Population Mutation Rate Estimates are Biased Upwards by the Reference Sequence After excluding variants in sequencing-error prone regions, 4,302,405 positions were identified at which at least one family member differed from the NCBI reference sequence and 3,733,299 positions at which at least one family member differed from the CEU major allele reference sequence (See FIG. 42A). With respect to the NCBI reference sequence, this corresponds to an estimated population mutation rate (Watterson's θ ((Watterson, G. A. On the number of segregating sites in genetical models without recombination. Theor Popul Biol 7, 256-276 (1975)) of $9.2 \times 10^{-4}$, matching previous estimates. (Roach, J. C., et al. Analysis of genetic inheritance in a family quartet by whole-genome sequencing. Science 328, 636-639 (2010).) However, in comparison with the CEU major allele reference, a lower ethnicity-specific population mutation rate of $7.8 \times 10^{-4}$ was estimated, suggesting that previous estimates may have been biased upwards by comparison with the NCBI reference sequence.

After short read mapping and local realignment, variants were called against the NCBI reference genome 37.1 and the CEU major allele reference. Likely spurious variant calls were first filtered by mapping quality, read depth and genotyping quality. The inheritance state for all allele assortments was determined by HMM and error prone regions (compression regions and Mendelian inheritance error rich (MIE)-rich regions, which represent likely sequencing errors) were identified and excluded. 606,757 fewer variants were identified when compared the CEU major allele reference than the NCBI reference genome 37.1 (HG19 reference) (See FIG. 42A). Approximately 8% and 9% of variants called against the HG19 reference (FIG. 42B) and CEU major allele reference (FIG. 42C) were rare (allele frequency<5%) or novel (not found in dbSNP or 1000 genomes pilot project data), respectively.

Phased Whole Genome Sequence Data Reveal HLA Types

Figure 2E:
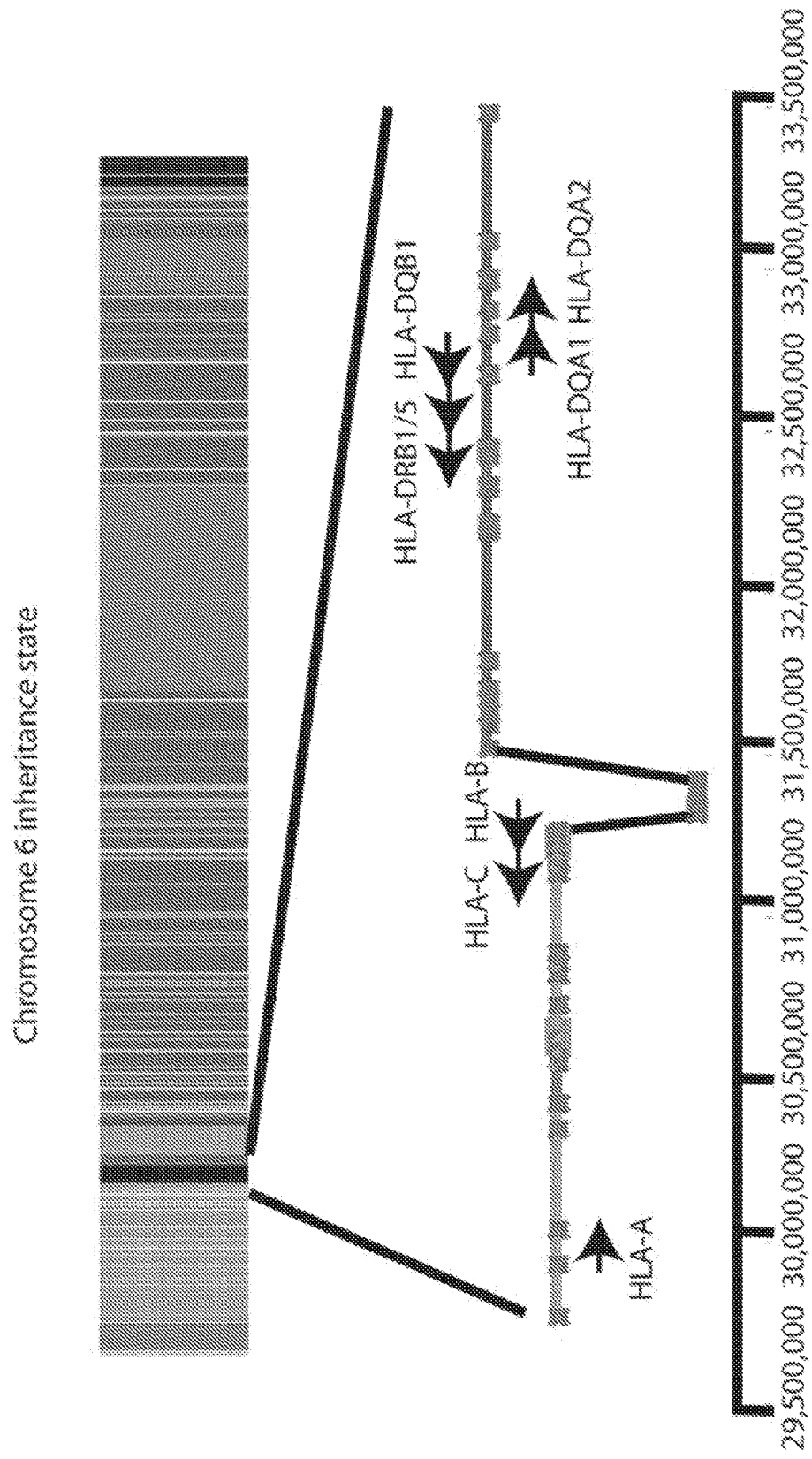
FIG. 2E illustrates the manner in which a HMM identified a recombination spanning the HLA-B locus and facilitated resolution of haplotype phase at HLA loci according to an embodiment of the present invention.
Figure 2F:
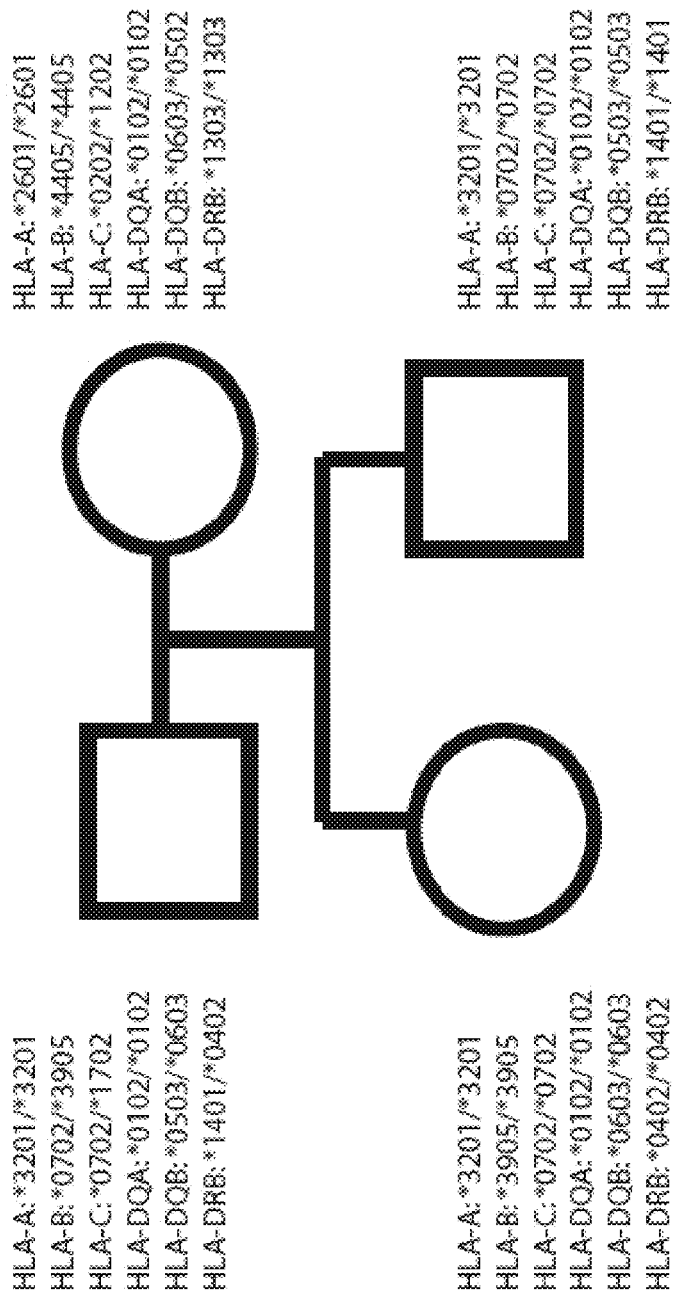
FIG. 2F shows common HLA types for family quartet based on phased sequence data according to an embodiment of the present invention.

Human leukocyte antigen (HLA) group typing from whole genome sequence data has previously been challenging due to the high recombination frequency on chromosome 6 that complicates phasing, as well as the extreme genetic diversity in the HLA loci. This approach that incorporates fine-mapping of recombination events with long-range phasing from polymorphic markers specific to the ethnic background of the sequenced family (e.g., variants called against the CEU major allele reference) and an iterative heuristic, described herein, for identifying the nearest HLA tag haplotype (de Bakker, P. I., et al. A high-resolution HLA and SNP haplotype map for disease association studies in the extended human MHC. Nat Genet 38, 1166-1172 (2006)) allowed for chromosome-specific HLA typing from whole genome sequence data as well as determination of the parental origin of HLA types (FIGS. 2E and 2F). HMM identified a recombination spanning the HLA-B locus and facilitated resolution of haplotype phase at HLA loci as shown in FIG. 2E. Common HLA types for family quartet based on phased sequence data are shown in FIG. 2F.

Rare Variant Analysis Identifies Multi-Genic Risk for Familial Thrombophilia

It has been estimated from population sequencing data that apparently healthy individuals harbor between 50 and 100 putative loss of function variants in genes associated with Mendelian diseases and traits. (Durbin, R. M., et al. A map of human genome variation from population-scale sequencing. Nature 467, 1061-1073 (2010).) Many of these variants have little or no significance either because they result in subtle phenotypes or have no biological effect. Thus, prioritization of putative loss of function variants remains a significant challenge.

To further characterize the potential adverse effects of non-synonymous single nucleotide variants (nsSNVs), a multiple sequence alignment (MSA) of 46 mammalian genomes was implemented. For coding variants of unknown significance, the mammalian evolutionary rate is proportional to the fraction of selectively neutral alleles (Kimura, M. Evolutionary rate at the molecular level. Nature 217, 624-626 (1968)) and can therefore serve as a prior expectation in determining the likelihood that an observed nsSNV is deleterious. This MSA was used in combination with existing algorithms (Adzhubei, I. A., et al. A method and server for predicting damaging missense mutations. Nat Methods 7, 248-249 (2010); Ng, P. C. & Henikoff, S. SIFT: Predicting amino acid changes that affect protein function. Nucleic Acids Res 31, 3812-3814 (2003)) to provide genetic risk predictions for phased putative loss of function variants for the family quartet (see heuristic in FIG. 44, summary in Table 5 (FIG. 46)).

Of 354,074 rare or novel variants compared with the CEU major allele reference sequence, 200 non-synonymous variants were identified in coding regions, one nonsense variant, one SNV in the conserved 3' splice acceptor dinucleotides, and 27 novel frame-shifting indels in genes associated with Mendelian diseases or traits. Consistent with prior observations and the extremely conserved regulatory role for miRNAs, no rare or novel SNVs were found in mature miRNA sequence regions or miRNA target regions in 3' UTRs. There were four compound heterozygous variants in disease-related genes and three homozygous variants in disease-related genes (See Table 7 (FIG. 48)). Five variants across the family quartet are associated with Mendelian traits (see Table 2 (FIG. 37).

The father has experienced two venous thromboemboli, the second of which occurred on systemic anticoagulation. One variant in the gene F5 encoding the coagulation factor V confers activated protein C resistance and increased risk for thrombophilia. (Koster, T., et al. Venous thrombosis due to poor anticoagulant response to activated protein C: Leiden Thrombophilia Study. Lancet 342, 1503-1506 (1993); Ridker, P. M., et al. Mutation in the gene coding for coagulation factor V and the risk of myocardial infarction, stroke, and venous thrombosis in apparently healthy men. N Engl J Med 332, 912-917 (1995).) Another variant (the thermolabile C677T variant) in the gene MTHFR encoding methylenetetrahydrofolate reductase, predisposes heterozygous carriers to hyper-homocysteinemia and may have a synergistic effect on risk for recurrent venous thromboembolism (Ridker, P. M., et al. Interrelation of hyperhomocyst (e)inemia, factor V Leiden, and risk of future venous thromboembolism. Circulation 95, 1777-1782 (1997); Margaglione, M., et al. The methylenetetrahydrofolate reductase TT677 genotype is associated with venous thrombosis independently of the coexistence of the FV Leiden and the prothrombin A20210 mutation. Thromb Haemost 79, 907-911 (1998)), though this association has more recently been questioned. (Bezemer, I. D., Doggen, C. J., Vos, H. L. & Rosendaal, F. R. No association between the common MTHFR 677C→T polymorphism and venous thrombosis: results from the MEGA study. Arch Intern Med 167, 497-501 (2007).)

Follow-up serological analysis demonstrated the father's serum homocysteine concentration was 11.5 μmol/L. A homozygous variant in F2, a gene known to be associated with hereditary thrombophilia, was able to be excluded based on its high evolutionary rate in multiple sequence alignment (See Table 6 (FIG. 47)). It is likely that these variants in F5 and MTHFR contribute digenic risk for thrombophilia passed to the daughter but not to the son from the father. The daughter has a third variant inherited from her mother in the hyaluronan binding protein 2 (HABP2) gene (the Marburg I polymorphism) known to be associated with inherited thrombophilia, thus contributing to multigenic risk for this trait. (Roemisch, J., Feussner, A., Nerlich, C., Stoehr, H. A. & Weimer, T. The frequent Marburg I polymorphism impairs the pro-urokinase activating potency of the factor VII activating protease (FSAP). Blood Coagul Fibrinolysis 13, 433-441 (2002); Sedding, D., et al. The G534E polymorphism of the gene encoding the factor VIIactivating protease is associated with cardiovascular risk due to increased neointima formation. J Exp Med 203, 2801-2807 (2006); Hoppe, B., et al. Marburg I polymorphism of factor VII-activating protease is associated with idiopathic venous thromboembolism. Blood 105, 1549-1551 (2005).) The described prediction pipeline recapitulated the only manifest phenotype, recurrent thromboembolism, in the family quartet.

Synonymous SNP Prediction Identifies a Putative Loss of Function Variant in ATP6V0A4

Association between synonymous SNPs (sSNPs) and disease has recently been described. (Macaya, D., et al. A synonymous mutation in TCOF1 causes Treacher Collins syndrome due to mis-splicing of a constitutive exon. Am J Med Genet A 149A, 1624-1627 (2009).) sSNPs may affect gene product function in several ways, including codon usage bias, mRNA decay rates, and splice site creation and/or disruption (See FIG. 45). An algorithm according to an embodiment of the invention and as described herein was developed and applied for predicting loss of function effects of 186 rare and novel sSNPs in OMIM-disease associated genes based on change in mRNA stability, splice site creation and loss, and codon usage bias. It was found that one sSNP in the gene ATP6V0A4 was predicted to significantly reduce mRNA stability, quantified by the change in free energy in comparison with the reference base at that position (see FIG. 3A). Homozygosity for loss of function (largely protein truncating) variants in this gene is associated with distal renal tubular acidosis, characterized by metabolic acidosis, potassium imbalance, urinary calcium insolubility, and disturbances in bone calcium physiology. (Smith, A. N., et al. Mutations in ATP6N1B, encoding a new kidney vacuolar proton pump 116-kD subunit, cause recessive distal renal tubular acidosis with preserved hearing. Nat Genet 26, 71-75 (2000).) The mother and both children are carriers of this putative loss of function mutation.

Figure 3A:
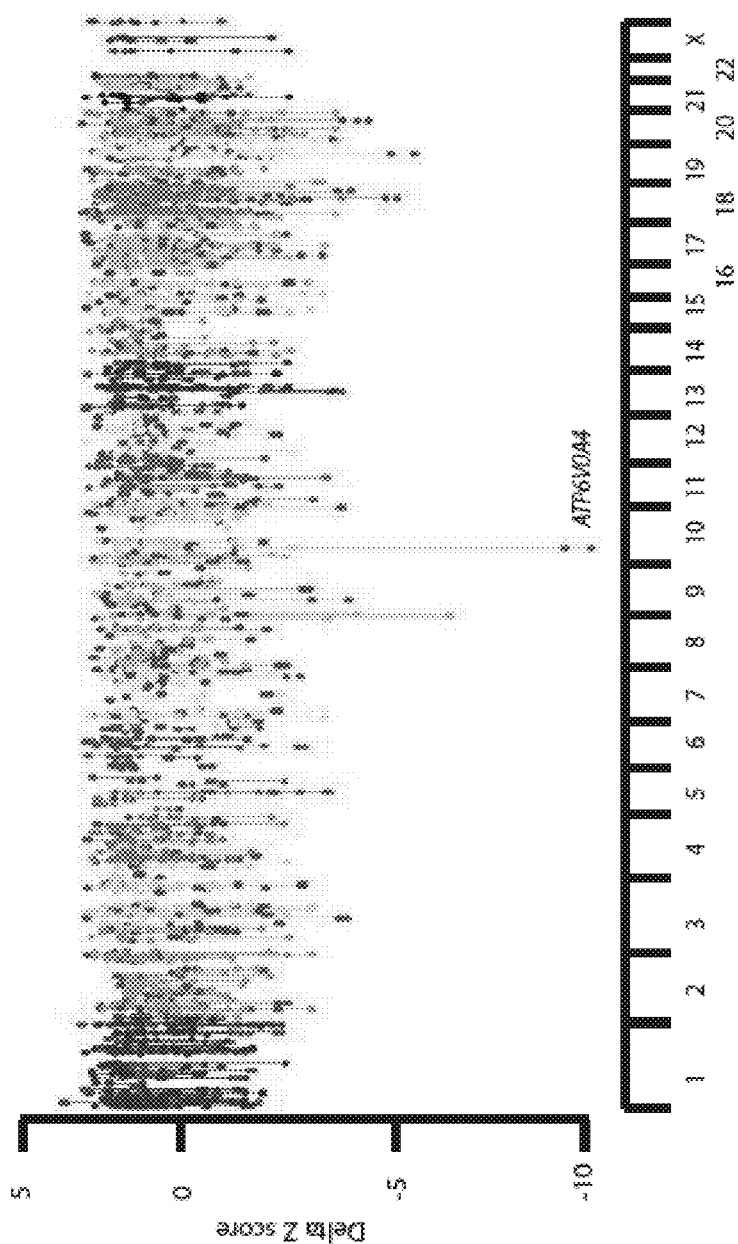
FIG. 3A illustrates the manner in which a Z score method for predicting free energy change conferred by synonymous single nucleotide variants identifies loci in the coding region of ATP6V0A4 associated with a significant change in mRNA stability according to an embodiment of the present invention.

The results of a Z score method for predicting free energy change conferred by synonymous single nucleotide variants identifies loci in the coding region of ATP6V0A4 associated with a significant change in mRNA stability are shown in FIG. 3A.

Common Variant Risk Prediction Identifies Risk for Obesity and Psoriasis

Figure 3B:
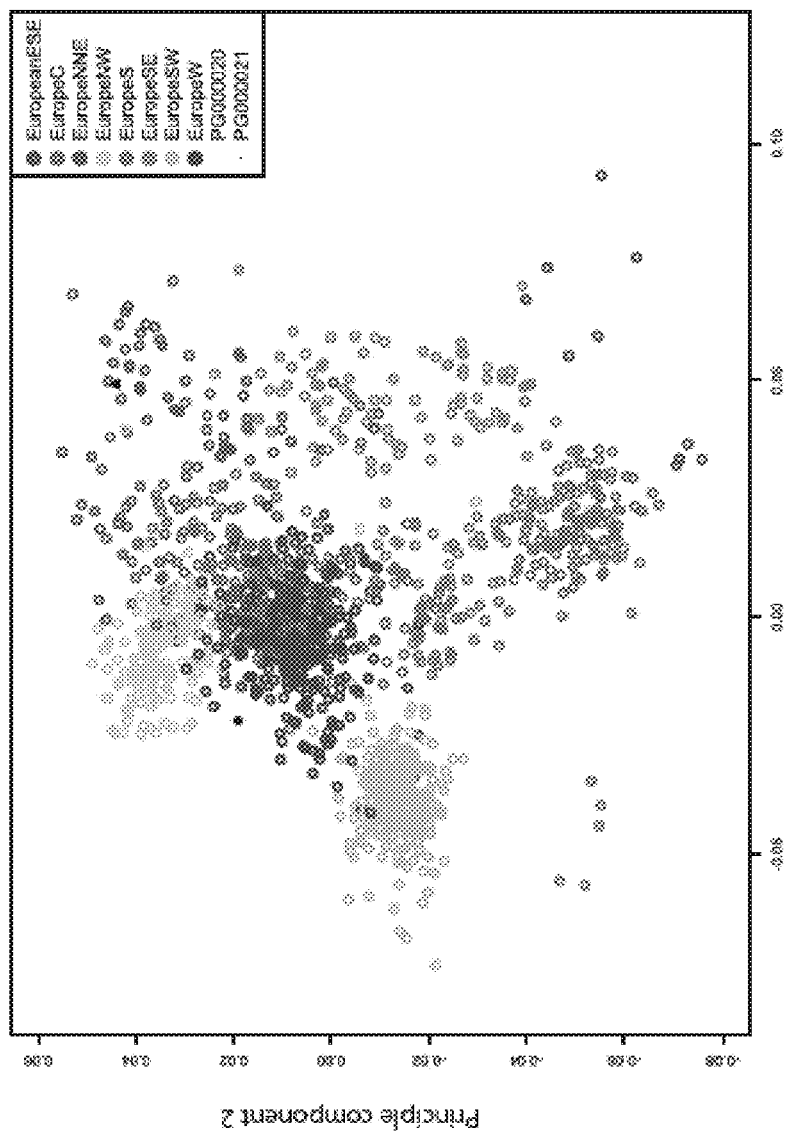
FIG. 3B shows an ancestry analysis of maternal and paternal origins based on principle components analysis of genotypes intersected with the Population Reference Sample dataset according to an embodiment of the present invention.
Figure 4:
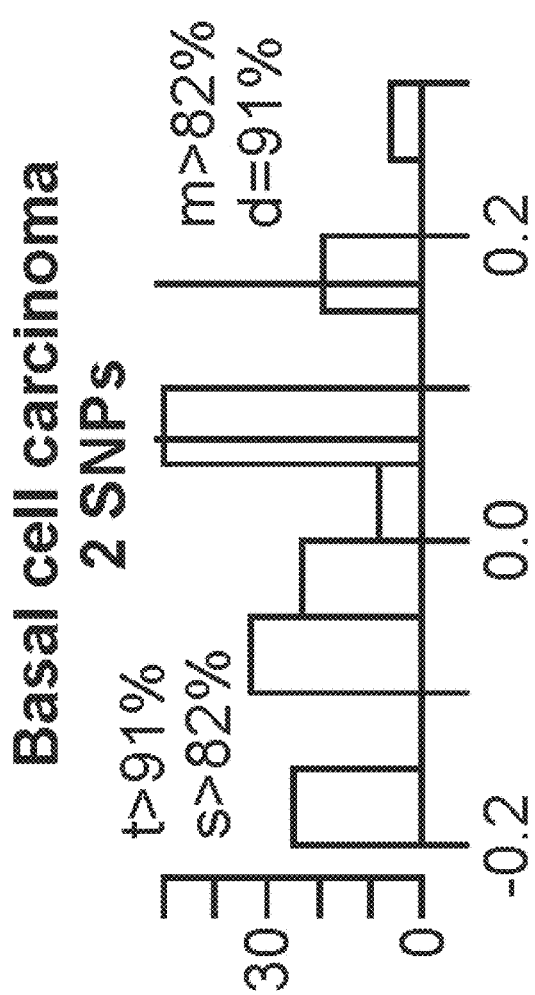
FIGS. 4-31 show graphs for common variant risk prediction for 28 disease states for each of the family members (f, father; m, mother; s, son; d, daughter) and 174 ethnicity-matched HapMap subjects according to an embodiment of the present invention.
Figure 5:
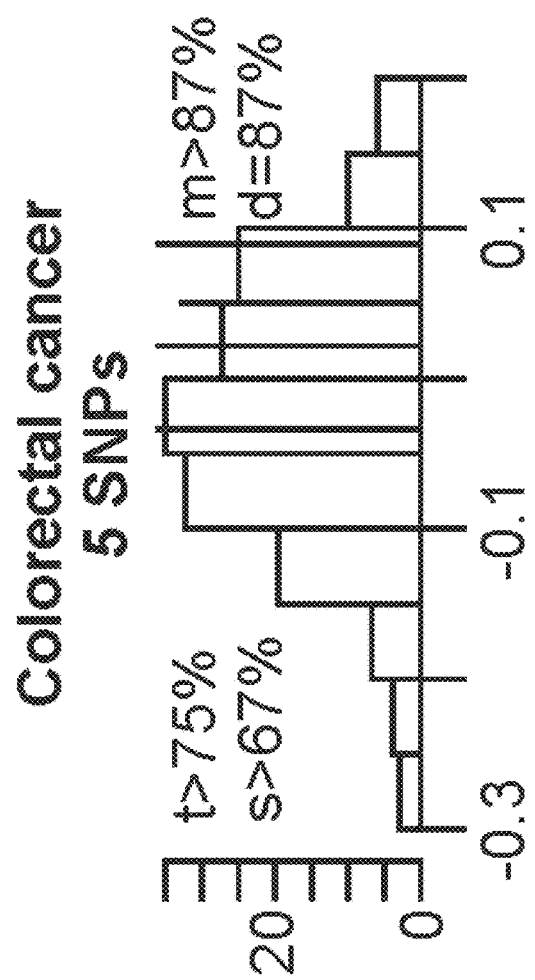
Figure 6:
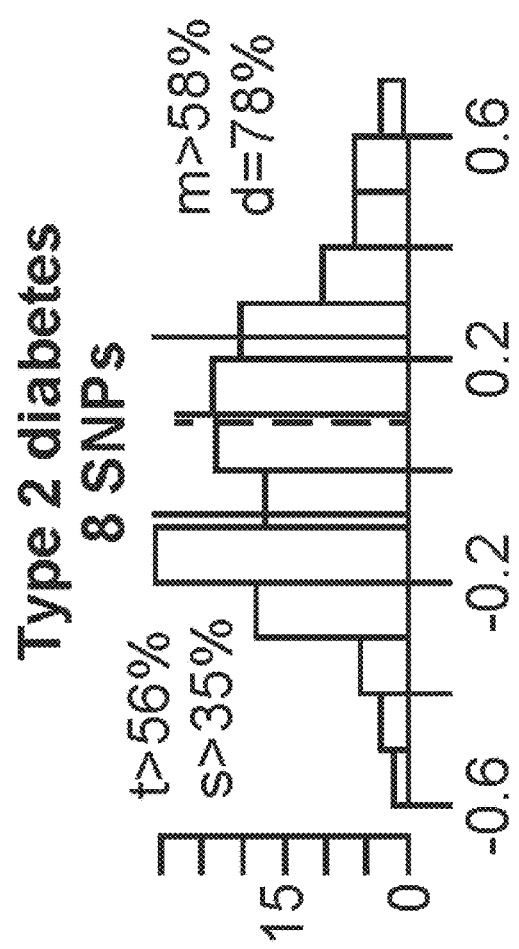
Figure 7:
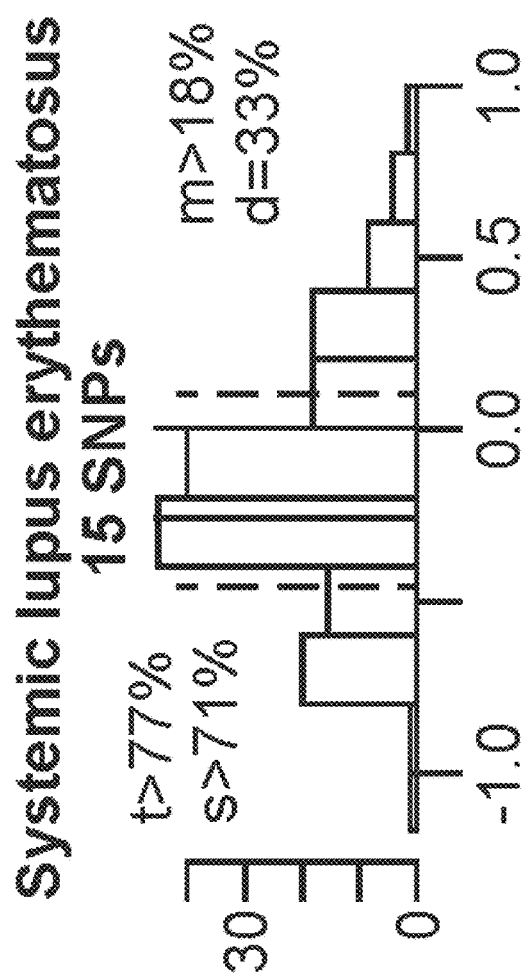
Figure 8:
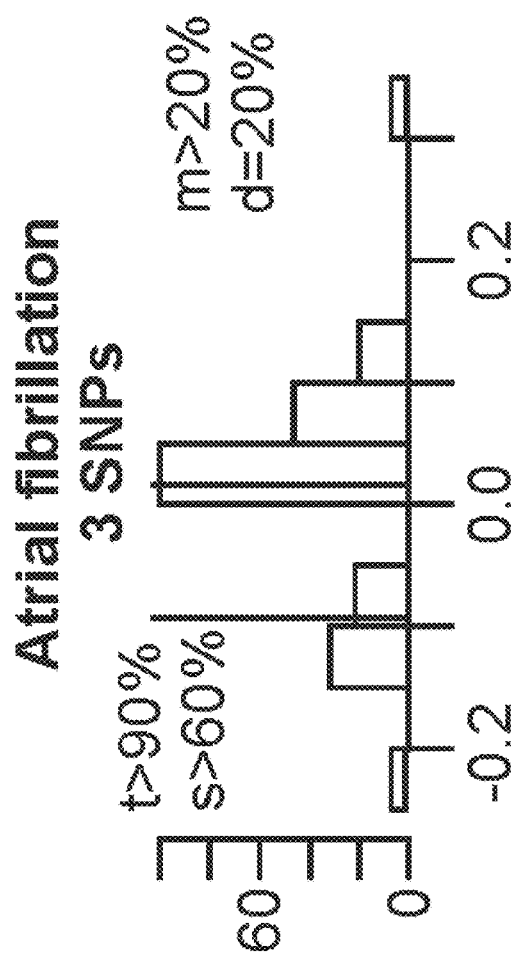
Figure 9:
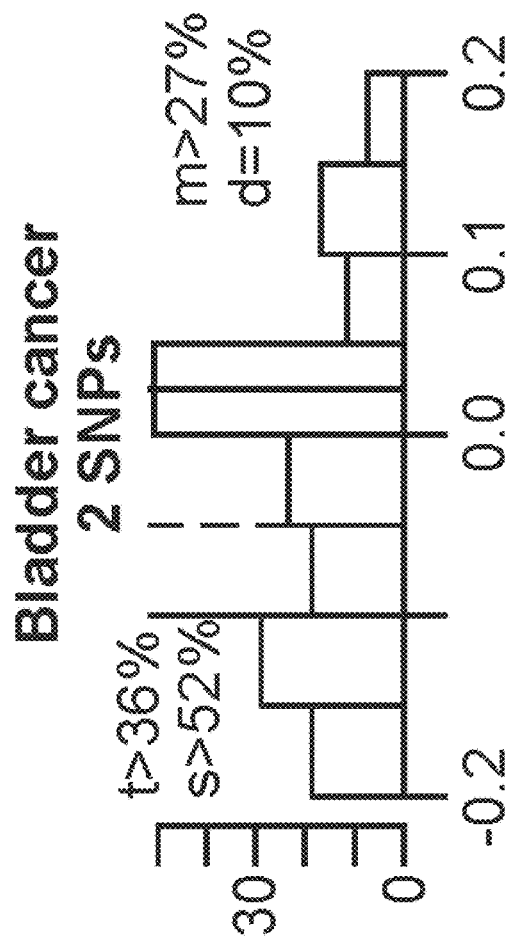
Figure 10:
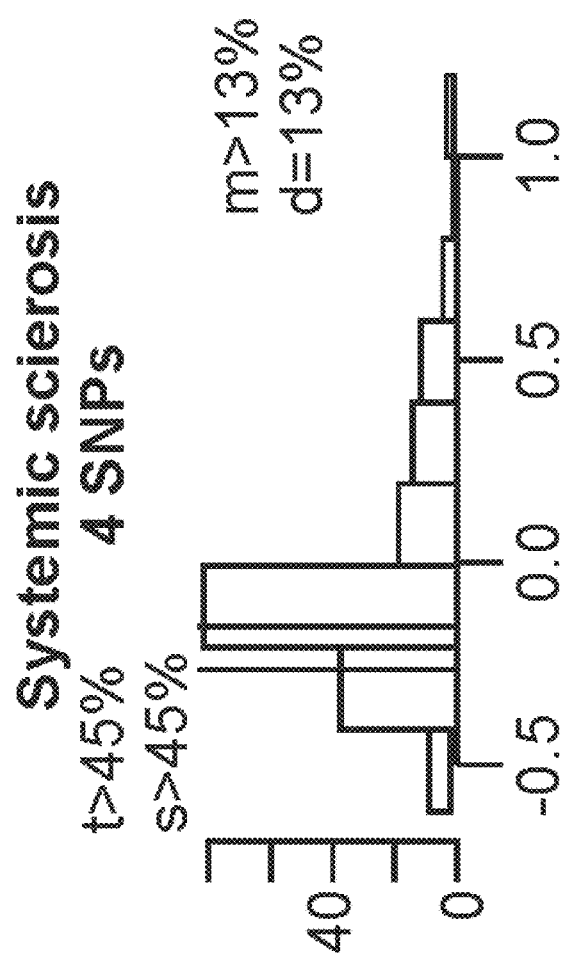
Figure 11:
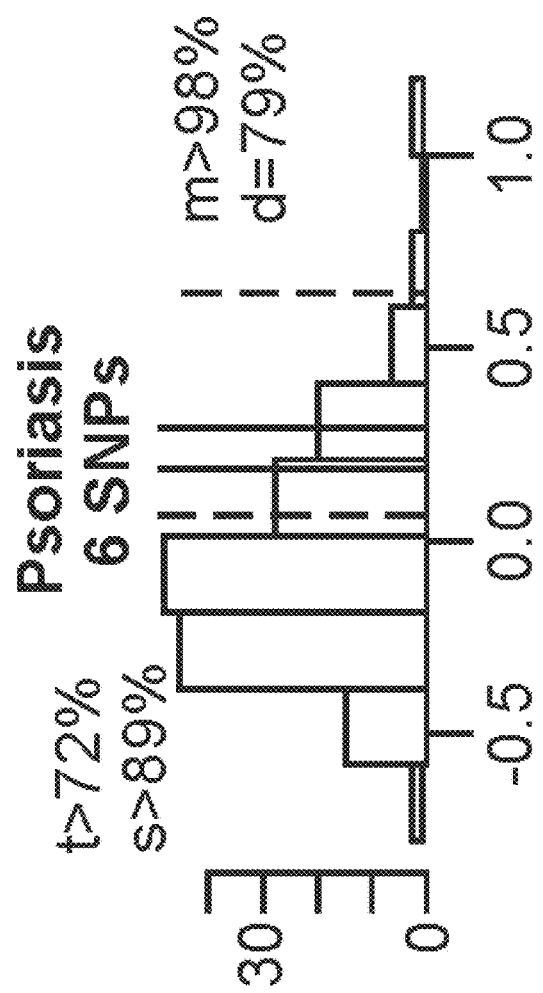
Figure 12:
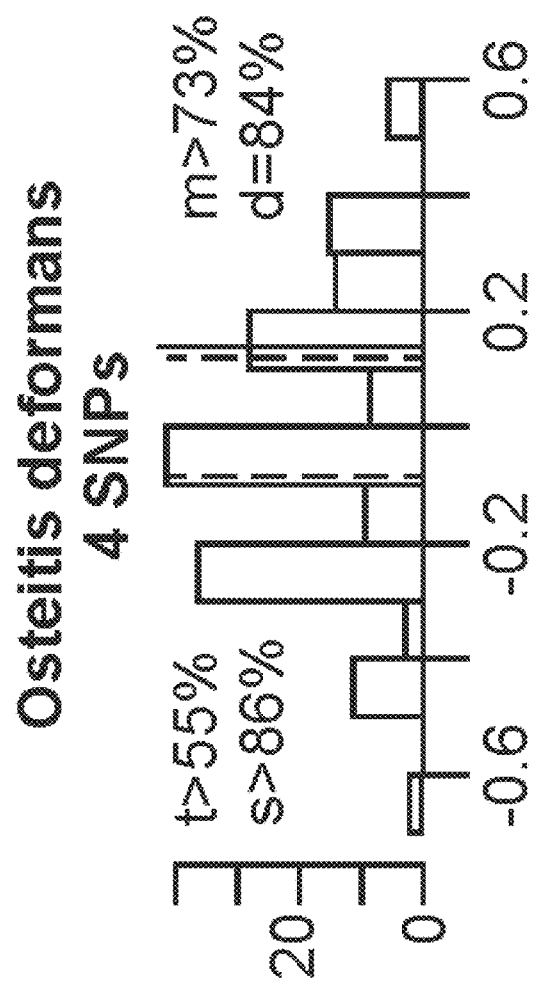
Figure 13:
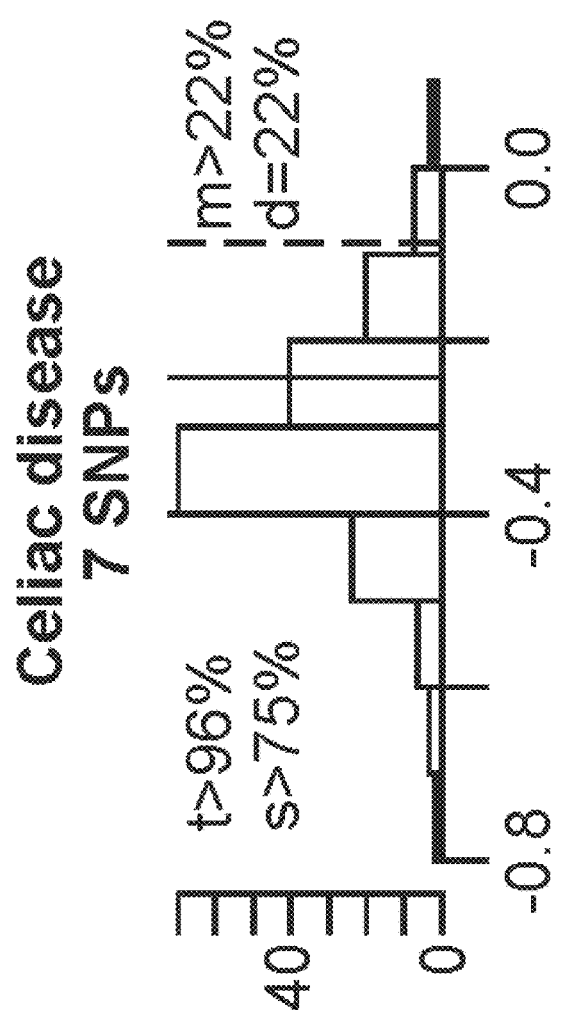
Figure 14:
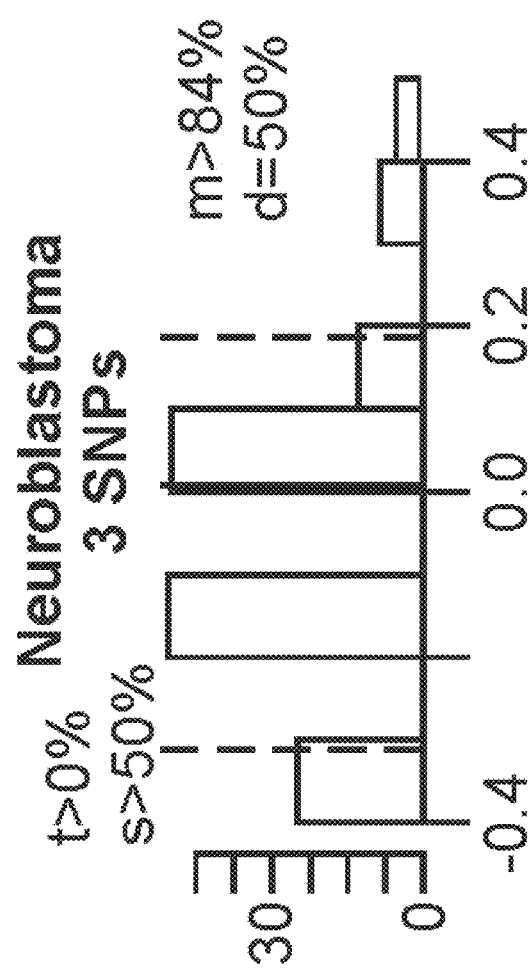
Figure 15:
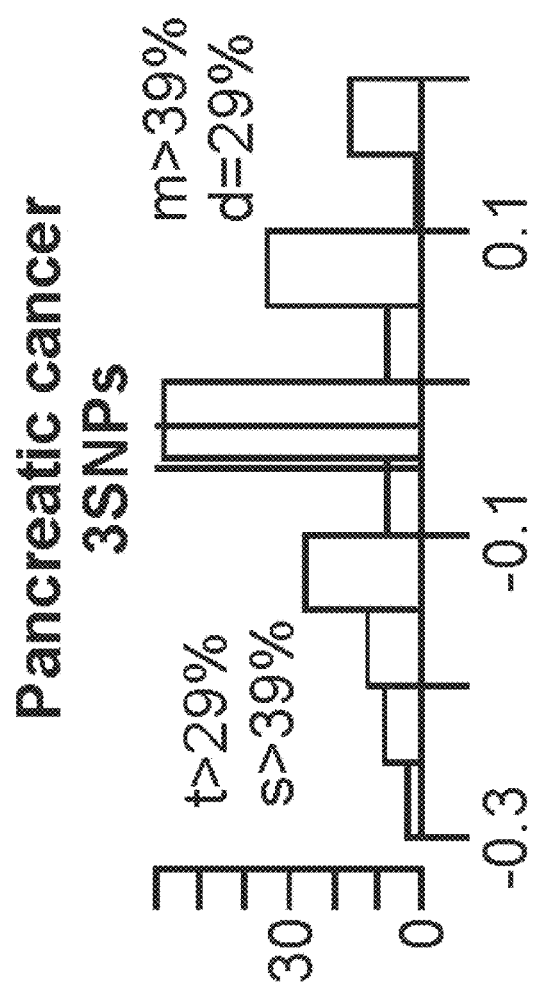
Figure 16:
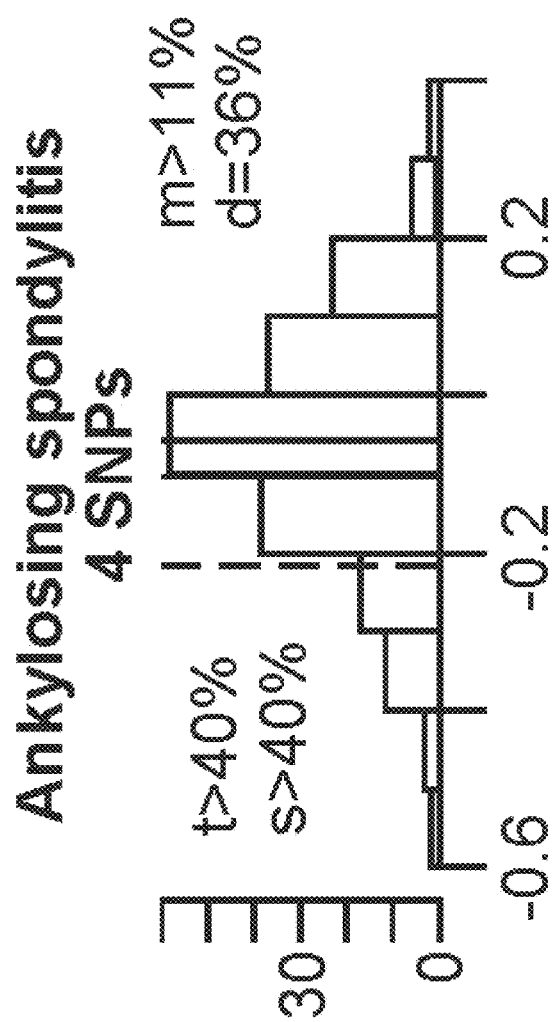
Figure 17:
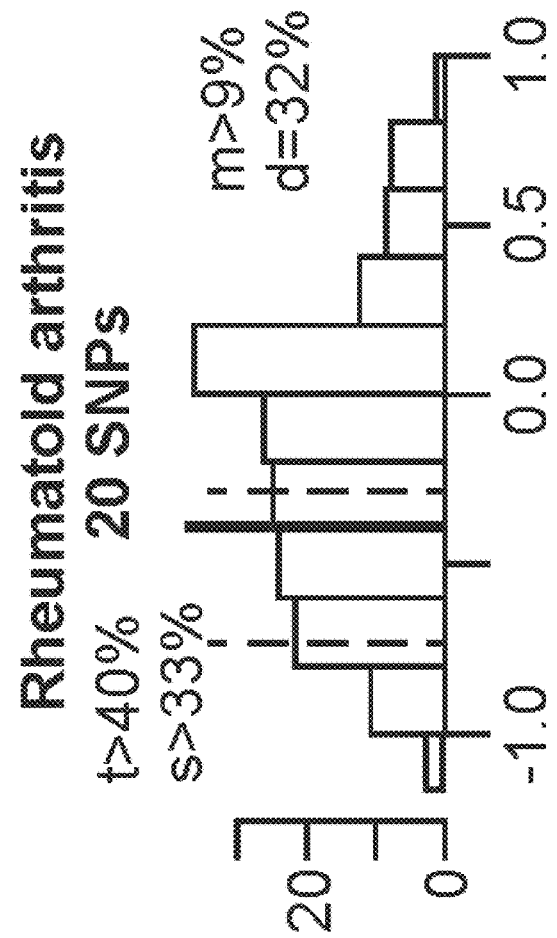
Figure 18:
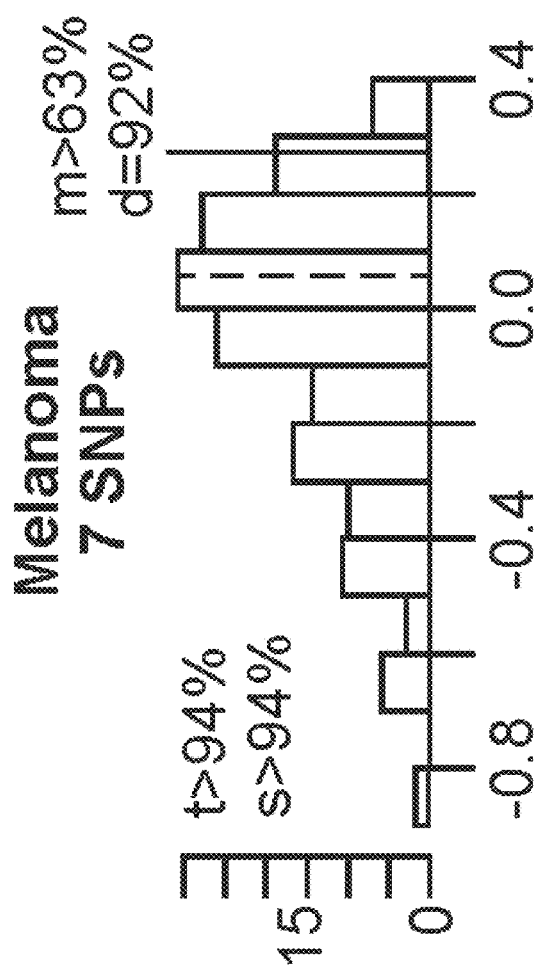
Figure 19:
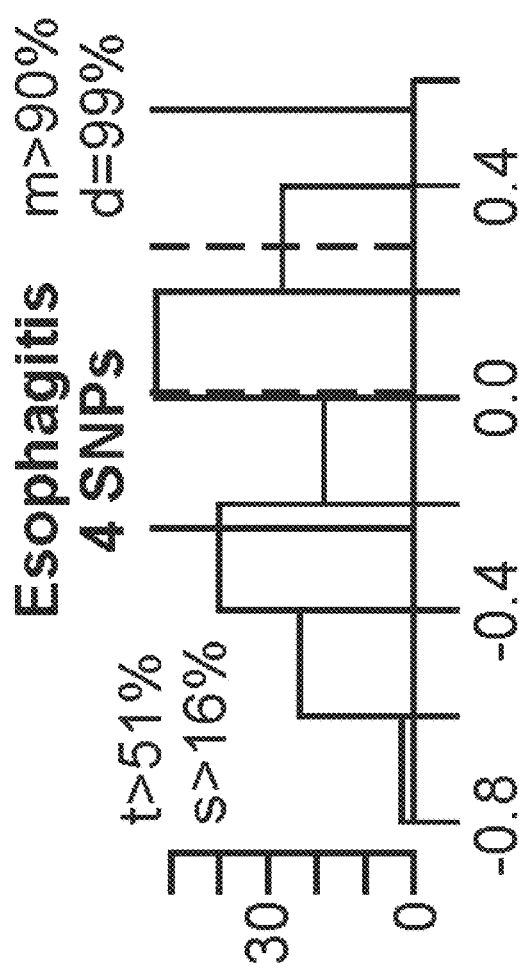
Figure 20:
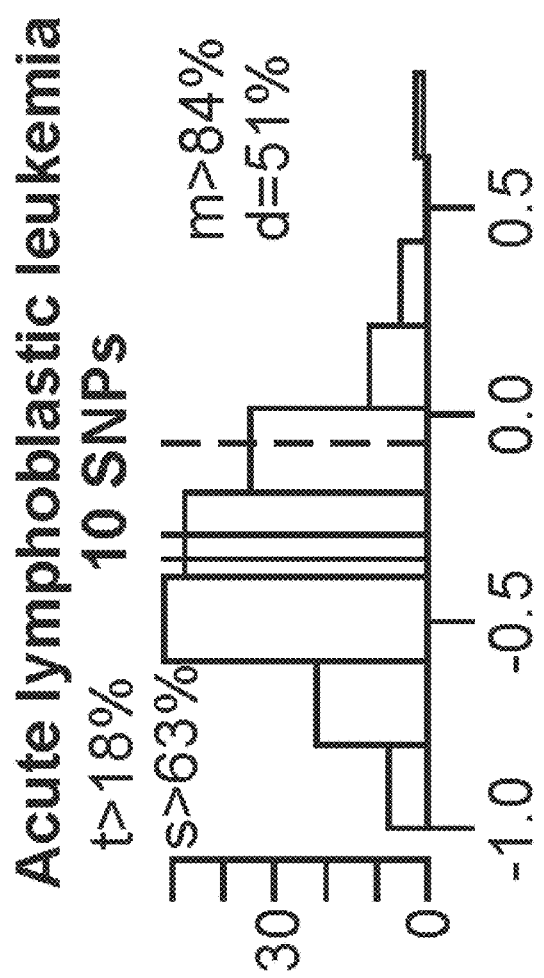
Figure 21:
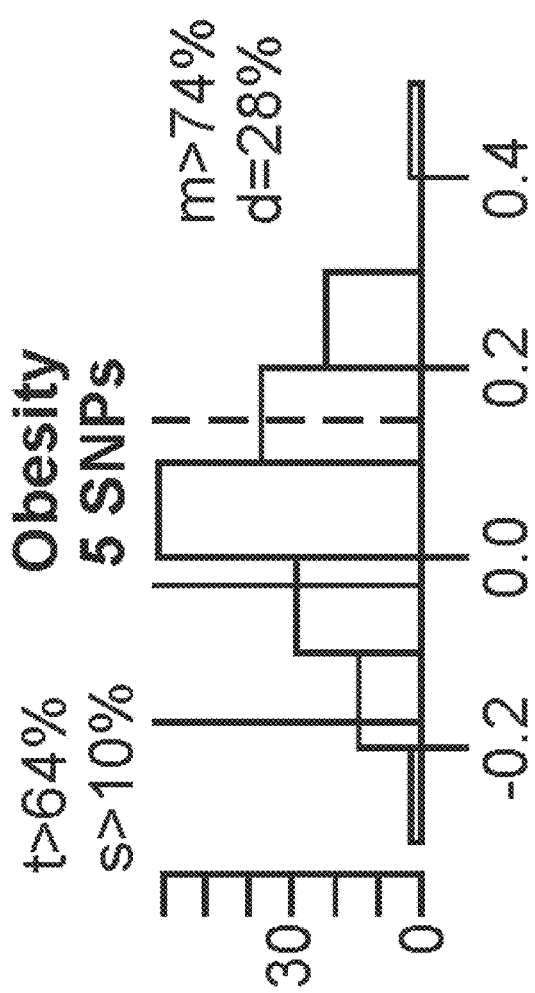
Figure 22:
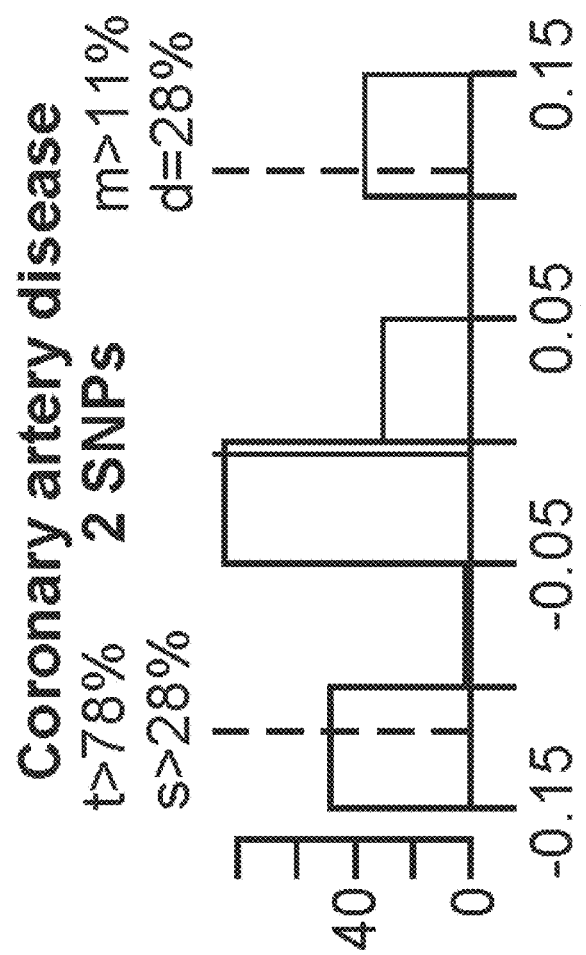
Figure 23:
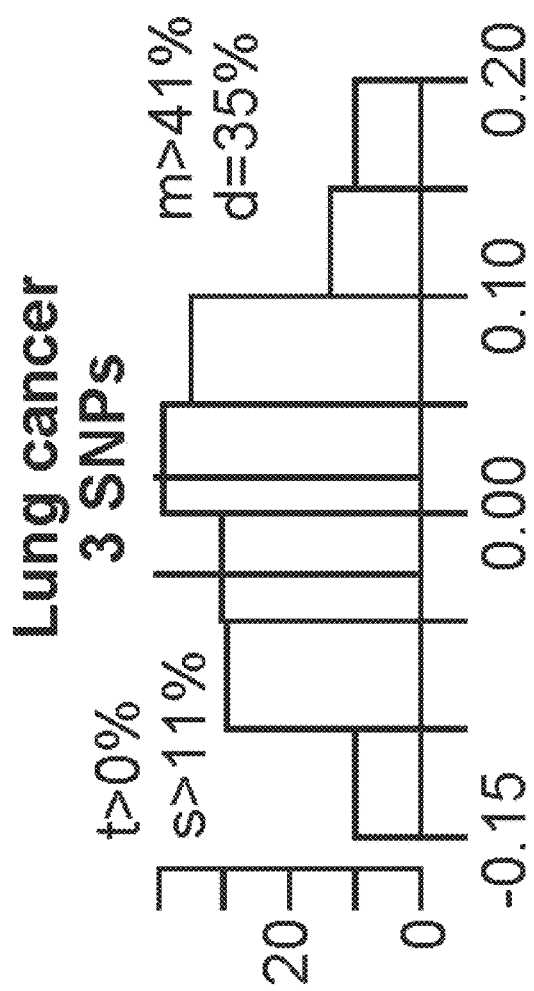
Figure 24:
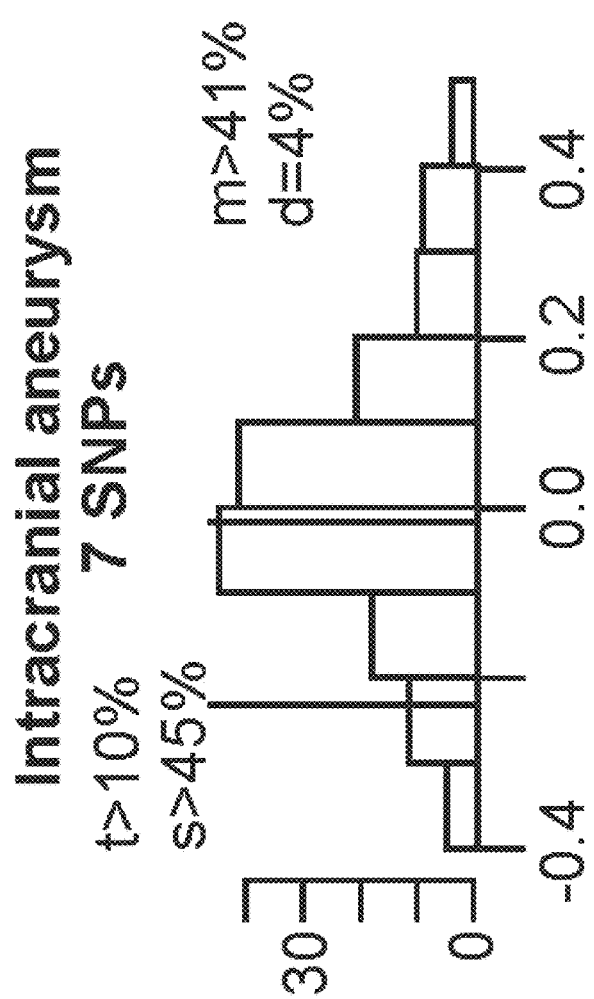
Figure 25:
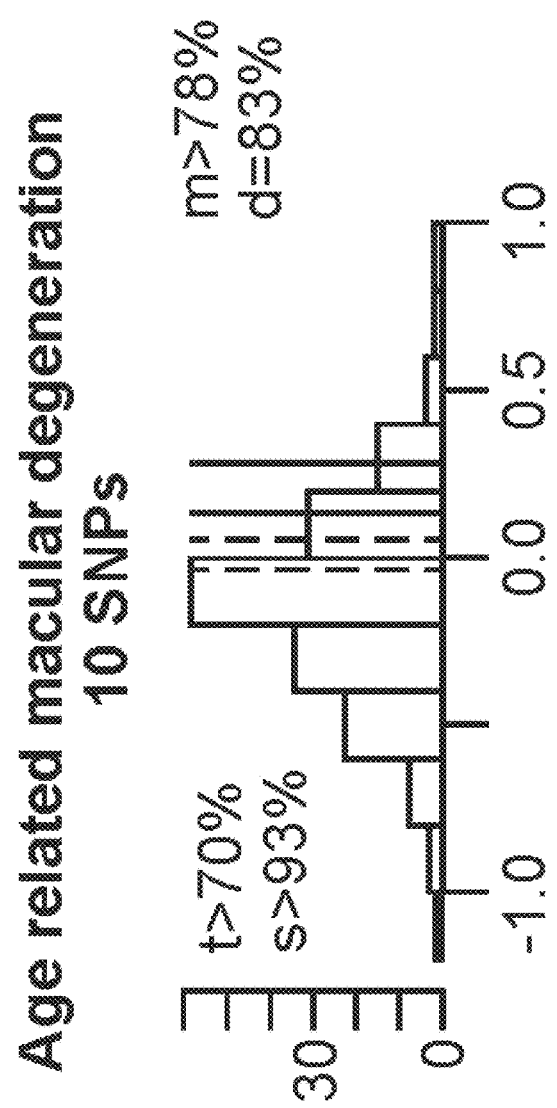
Figure 26:
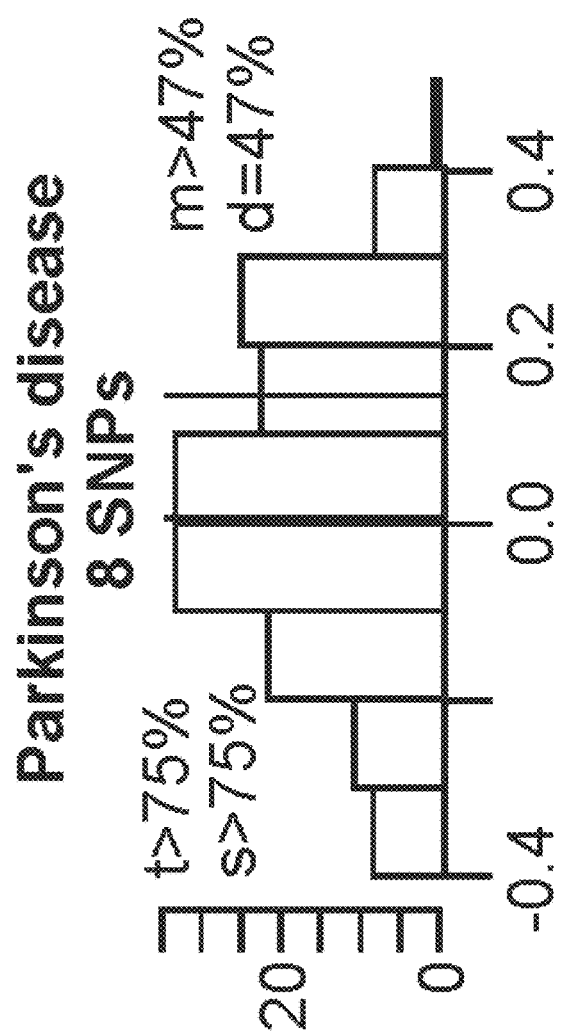
Figure 27:
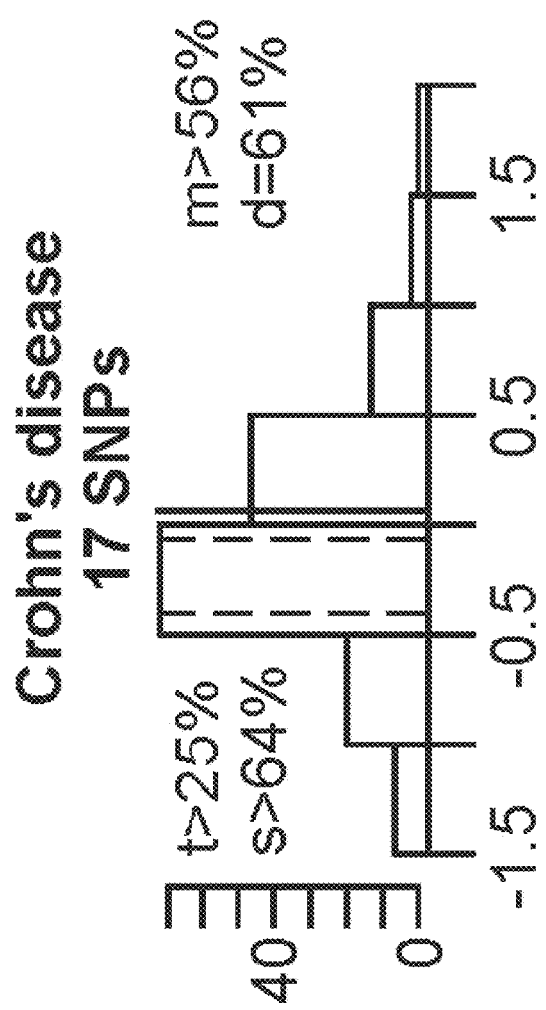
Figure 28:
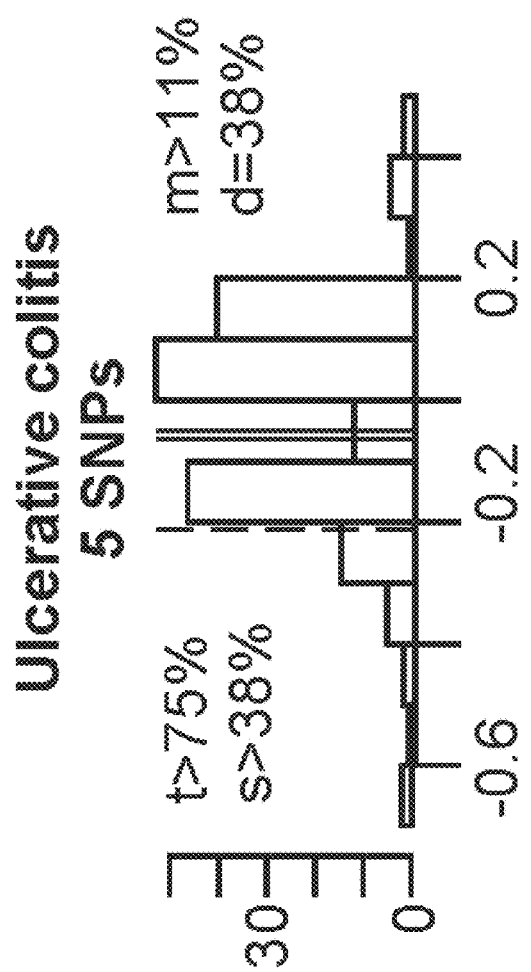
Figure 29:
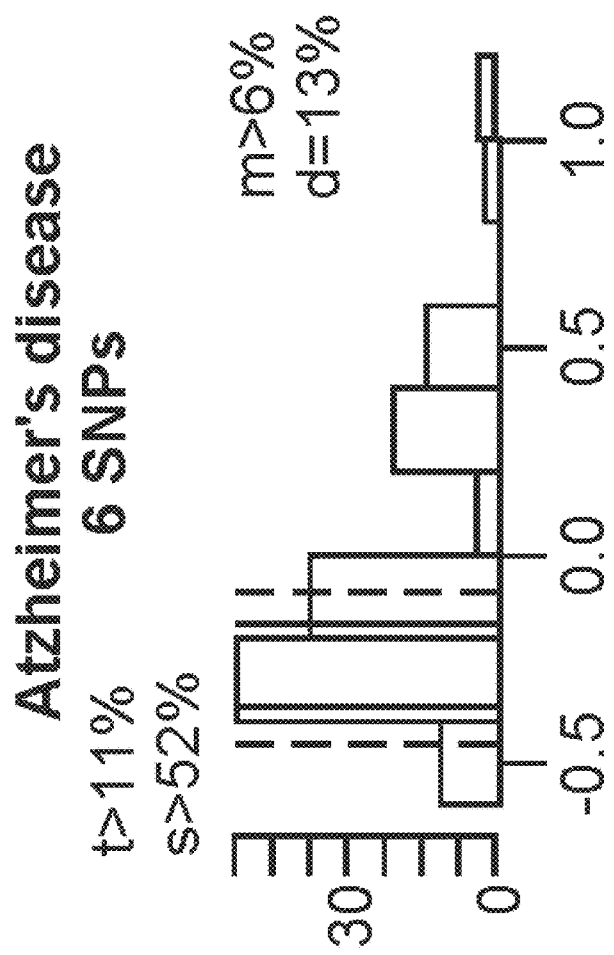
Figure 30:
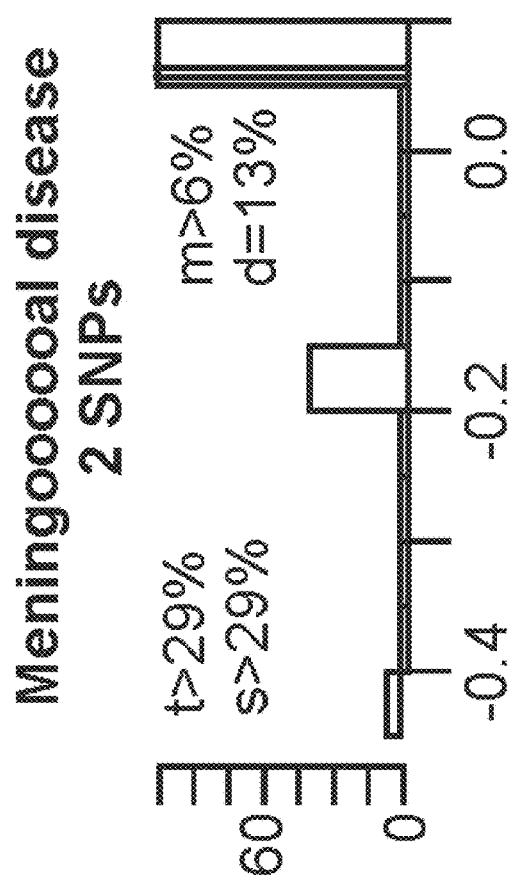
Figure 31:
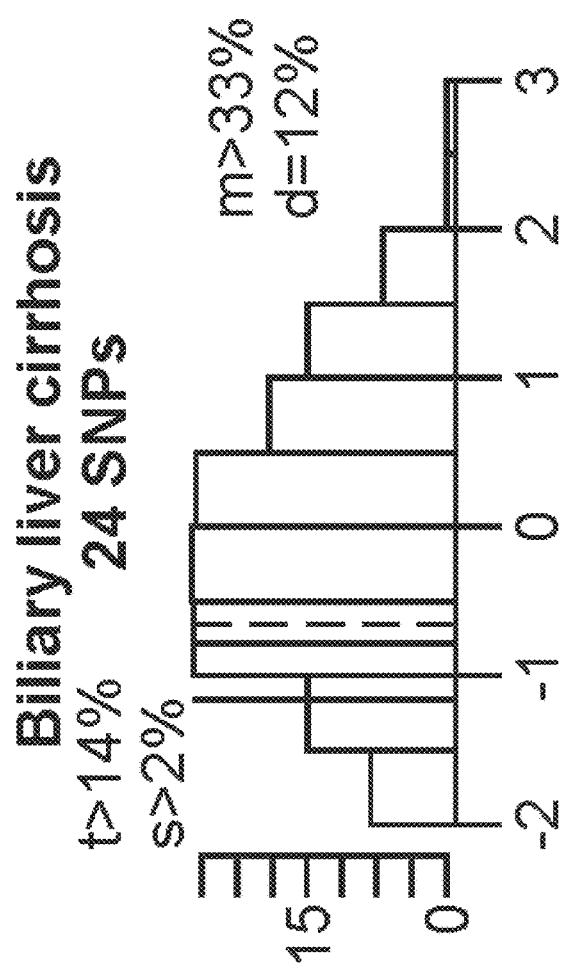

Results from Genome Wide Association Studies (GWAS) provide a rich data source for assessment of common disease risk in individuals. To provide a population risk framework for genetic risk predictions for this family quartet, ancestral origins were first localized based on principal components analysis of common SNP data in each parent and the Population Reference Sample (POPRES) dataset (Nelson, M. R., et al. The Population Reference Sample, POPRES: a resource for population, disease, and pharmacological genetics research. Am J Hum Genet 83, 347-358 (2008)), demonstrating North/Northeastern and Western European ancestral origins for maternal and paternal lineages, respectively (see FIG. 3B). Ancestry analysis of maternal and paternal origins based on principle components analysis of genotypes intersected with the Population Reference Sample dataset is shown in FIG. 3B.

Composite likelihood ratios were then calculated for 28 common diseases for 174 ethnically-concordant HapMap CEU individuals, and provided percentile scores for each study subject's composite LR for each disease studied (see FIGS. 4-31). Shown in FIGS. 4-31 is common variant risk prediction for 28 disease states for each of the family members (f, father; m, mother; s, son; d, daughter) and 174 ethnicity-matched HapMap subjects. The x-axis in each plot represents the log 10(likelihood ratio) for each disease according to the allelic distribution in the population for SNPs identified in the literature as significantly associated with disease by 2 or more studies including 2000 or more total subjects.

Figure 32:
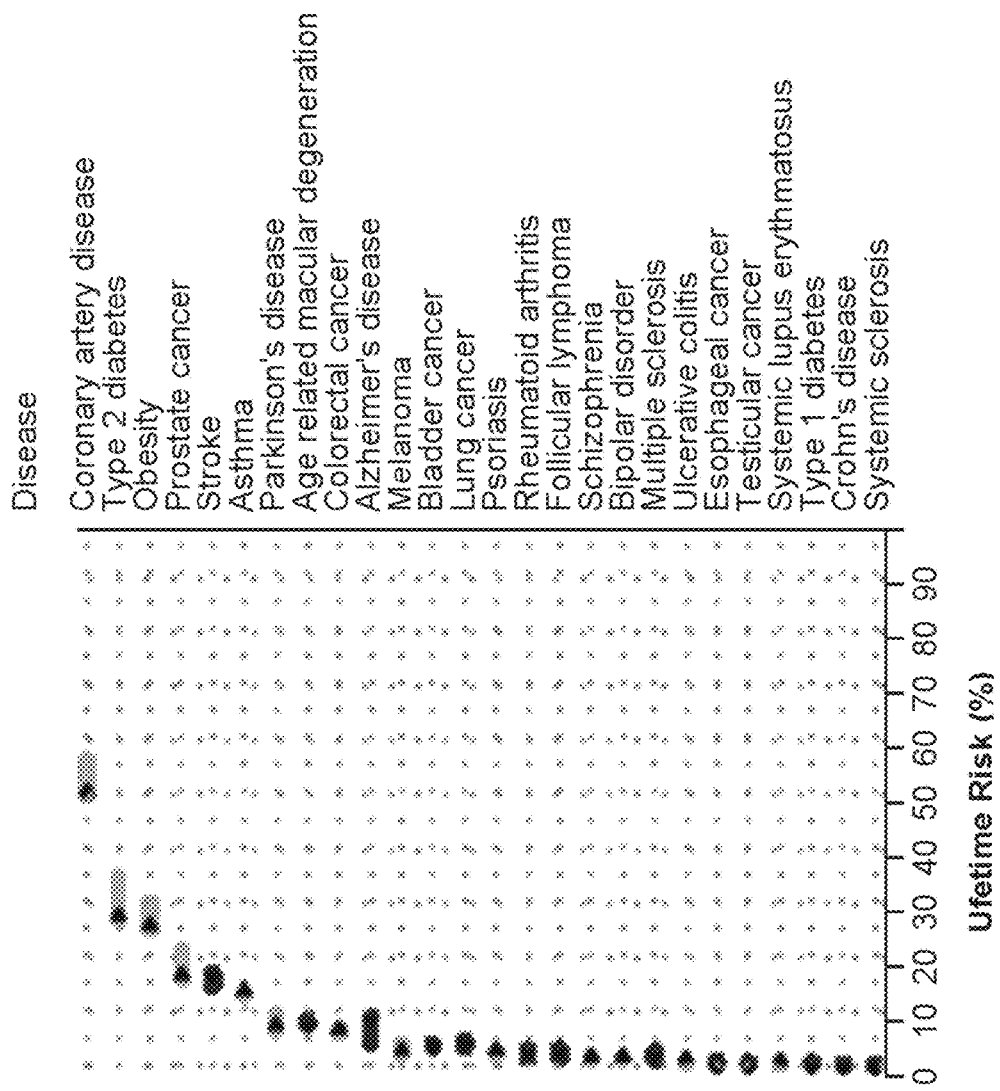
FIG. 32 is a plot of pre (arrow base) and post (bar end) estimates of disease risk for the father according to common variant risk prediction, derived from the pre-probability of disease multiplied by the composite likelihood ratio from all SNPs meeting the criteria described above according to an embodiment of the present invnetion.
Figure 33:
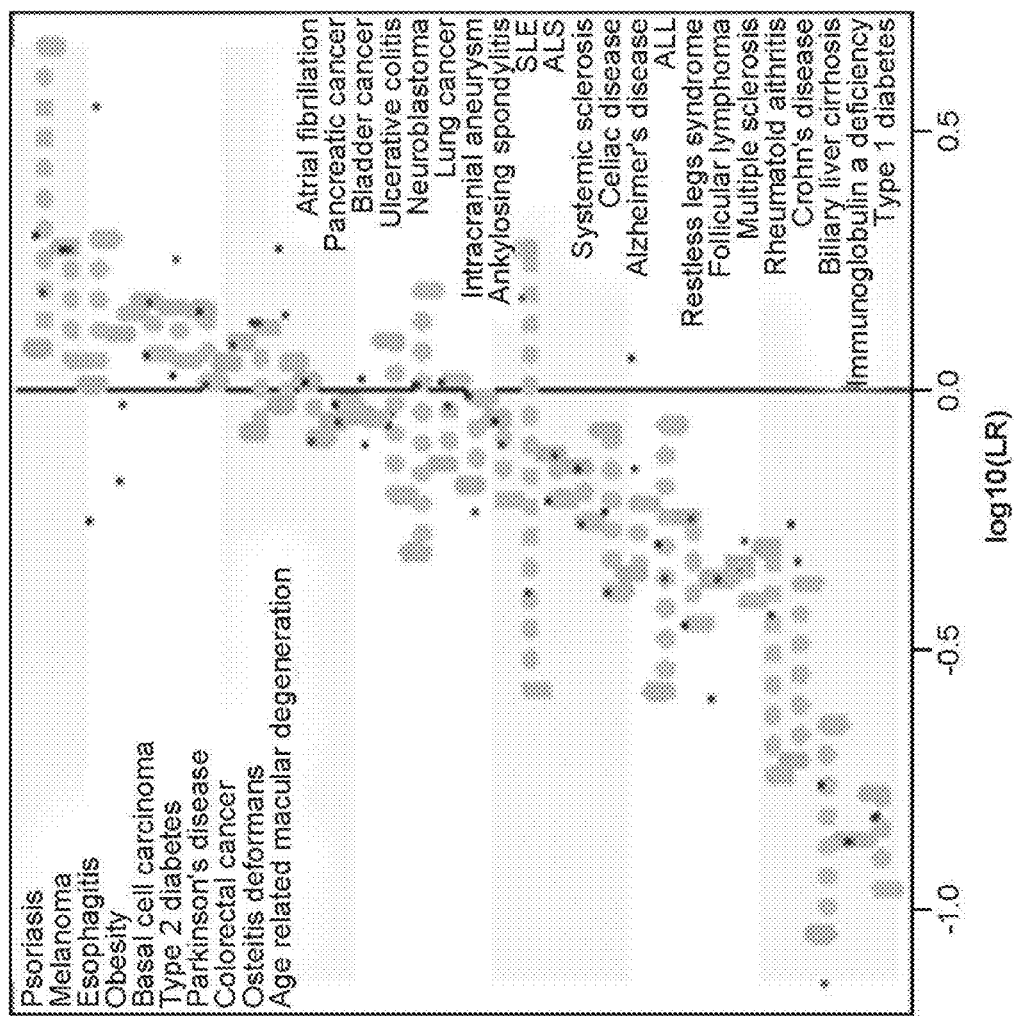
FIG. 33 plots composite likelihood ratio estimates for disease risk according to common genetic variation according to an embodiment of the present invention.
Figure 34:
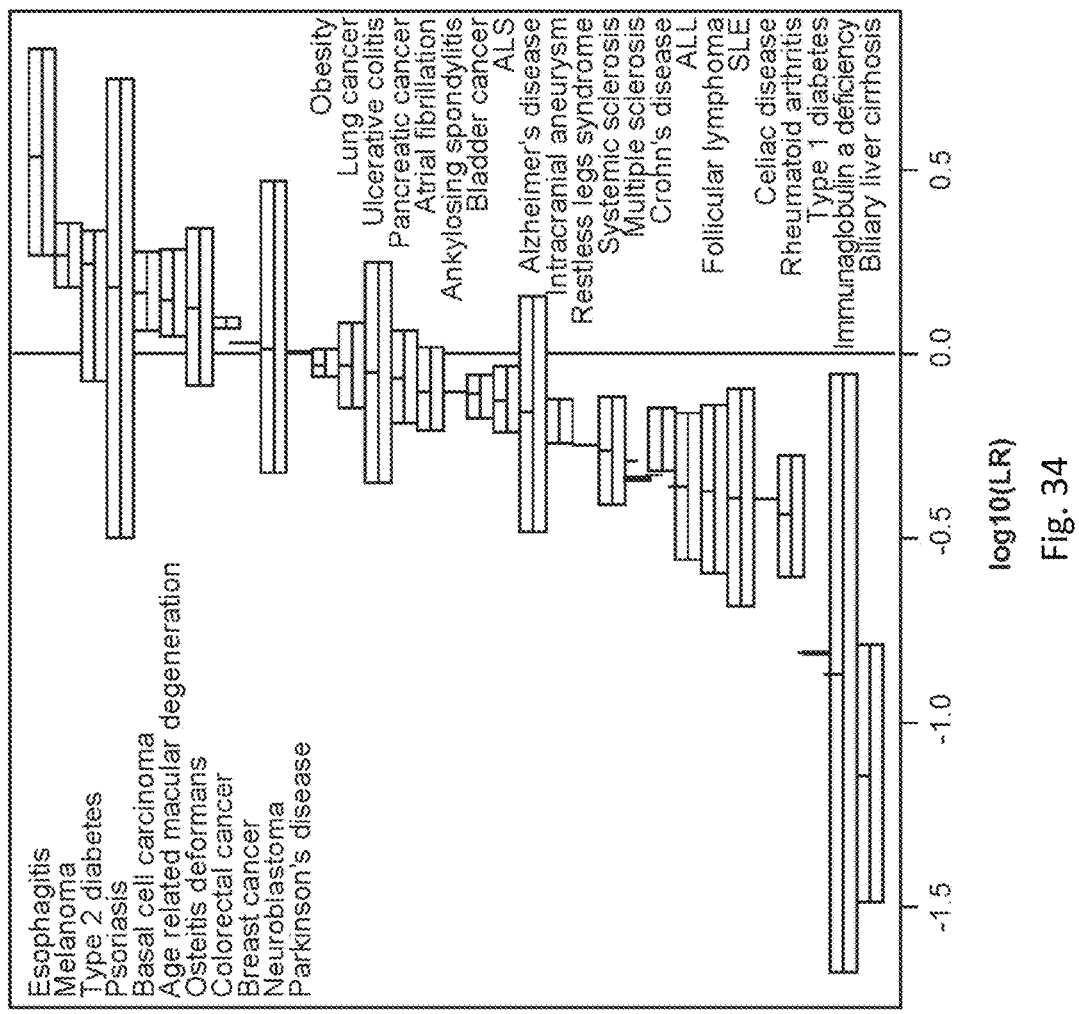
FIG. 34 plots the parental haplotype contribution to disease risk for each child (points) for the daughter according to an embodiment of the present invention.

All four family members were at high risk for psoriasis, with the mother and daughter at highest risk (98th and 79th percentiles, respectively), consistent with clinical manifestations of psoriasis in both the father and daughter. It was also found that both parents were predisposed to obesity, while both children had low genetic risk for obesity. This approach was extended to incorporate haplotype phased SNP data in assessment of genetic risk, providing estimates of disease risk according to parental risk haplotypes (see FIGS. 32-35). Shown in FIG. 32 are pre (arrow base) and post (bar end) estimates of disease risk for the father according to common variant risk prediction, derived from the pre-probability of disease multiplied by the composite likelihood ratio from all SNPs meeting the criteria described above. Shown in FIG. 33 are composite likelihood ratio estimates for disease risk according to common genetic variation. Parental haplotype contribution to disease risk for each child (points) is shown for the daughter in FIG. 34 and the son in FIG. 35.

Pharmacogenomic Variant Annotation Predicts Empiric Warfarin Dosing

The Pharmacogenomics Knowledge Base, PharmGKB, was used to evaluate associations between phased variants and 141 drugs (See Tables 9-11 (FIGS. 50-52)). In light of the family history of venous thrombosis and the father's use of the anticoagulant warfarin, focus was placed on relationships between SNPs and anticoagulant and antiplatelet agents. All family members are homozygous for the most common CYP2C9 allele (CYP2C9*1, Table 3 (FIG. 38)) associated with normal warfarin pharmacokinetics and heterozygous for the allele at VKORC1-1639 (rs9923231) associated with therapeutic prolongation of the international normalized ratio at low doses of warfarin. This variant data and clinical data was used to predict the father's exact empirically-determined dose of warfarin (5 mg) using the International Warfarin Pharmacogenetics Consortium dosing algorithm. (Klein, T. E., et al. Estimation of the warfarin dose with clinical and pharmacogenetic data. N Engl J Med 360, 753-764 (2009).)

It was also found that the mother and daughter are both homozygous for an ultra-rapid metabolism allele at CYP2C19, which encodes a key metabolizer of the pro-drug clopidogrel, an antiplatelet agent used in the prevention and therapy of cardiovascular disease. Because the metabolic activity of CYP2C19 is directly correlated with the antiplatelet activity of clopidogrel, there is a higher bleeding risk associated with clopidogrel use in the mother and daughter. This finding has significant implications for the daughter who has multigenic risk for thrombophilia and may require anticoagulant therapy should she develop thrombosis; concomitant use of clopidogrel in this setting may contribute further to bleeding risk associated with systemic anticoagulation. Full details of pharmacogenetic variants in other key metabolic enzymes and associated pharmacokinetic and pharmacodynamic profiles are displayed in Table 4 (FIG. 39).

Discussion

Here, phased genetic risk assessment in a family quartet using whole genome sequencing and a novel ethnicity-specific major allele reference is discussed. At approximately 1.6 million genomic positions, it was found that the NCBI reference sequence differed from the major allele in each of the three HapMap populations. New estimates were provided for the population mutation rate which illustrate the upward bias in estimates based on comparison with the NCBI human reference genome sequence and show that use of the reference sequence for variant calling may result in spurious genotype calls at medically relevant SNP loci.

Family quartet sequencing allows for providing a fine map of meiotic crossover sites to sub-kb resolution for the first time, finding that meiotic crossovers happen with nearly equal frequency in male and female parents in this family quartet. This is in contrast to previous observations in a family quartet and to observations of greater recombination frequency in females than in males in mice. (Roach, J. C., et al. Analysis of genetic inheritance in a family quartet by whole-genome sequencing. Science 328, 636-639 (2010); Paigen, K., et al. The recombinational anatomy of a mouse chromosome. PLoS Genet 4, e1000119 (2008); Petkov, P. M., Broman, K. W., Szatkiewicz, J. P. & Paigen, K. Crossover interference underlies sex differences in recombination rates. Trends Genet 23, 539-542 (2007).) Estimates of human sex-specific recombination rates have demonstrated significant variation in recombination number, particularly in females. (Kong, A., et al. Fine-scale recombination rate differences between sexes, populations and individuals. Nature 467, 1099-1103 (2010); Broman, K. W., Murray, J. C., Sheffield, V. C., White, R. L. & Weber, J. L. Comprehensive human genetic maps: individual and sex-specific variation in recombination. Am J Hum Genet 63, 861-869 (1998); Kujovich, J. L. Factor V Leiden thrombophilia. Genet Med 13, 1-16 (2010).) Notably, the RNF212 haplotypes revealed by long range phasing in this quartet are associated with lower than average female and average male recombination rates (Kong, A., et al. Sequence variants in the RNF212 gene associate with genome-wide recombination rate. Science 319, 1398-1401 (2008)), potentially explaining the described observations.

In this quartet, the power of sequencing nuclear families was leveraged for identification of >90% of sequencing errors, providing unprecedented accuracy of sequence information used for genetic risk interpretation and identification of compound heterozygous and multigenic disease risk. This approach, first applied to a family quartet in which two family members had Miller syndrome and ciliary dyskinesia (Roach, J. C., et al. Analysis of genetic inheritance in a family quartet by whole-genome sequencing. Science 328, 636-639 (2010)) was extended into a tool for phasing genetic variants.

Algorithms for multiple sequence alignment for novel and rare nonsynonymous variant risk prediction, and functional prediction for the effects of synonymous SNPs were developed and applied. In doing so, multigenic risk for thrombophilia in the father and daughter was identified, consistent with a history of recurrent venous thromboembolism in the father despite systemic anticoagulation. This multigenic risk for thrombophilia is more consistent with the father's clinical history of recurrent thromboembolism on systemic anticoagulation than monogenic risk conferred by heterozygous factor V Leiden alone, which was previously identified as the putative etiological factor in clinical assessment. (Kujovich, J. L. Factor V Leiden thrombophilia. Genet Med 13, 1-16 (2010).) Furthermore, multigenic risk for thrombophilia identified in the daughter prior to first venous thrombosis has significant clinical implications in terms of risk mitigation.

Phased variant information allows for determination of parental contribution to common disease risk. Furthermore, several common SNPs have been associated with disease risk, most notably diabetes mellitus 2, in a sex specific manner, such that maternal origin confers direct association with risk of disease and paternal origin confers indirect association with disease risk. (Kong, A., et al. Parental origin of sequence variants associated with complex diseases. Nature 462, 868-874 (2009).) Additionally, phasing variant data demonstrated the origin of discordant parent-child risks for common disease. The presently described methods for determining parental origin of risk alleles allows for precise risk assessment utilizing this information as a prior, in contrast to existing un-phased genotype data.

The ethnicity-specific, family-based approaches to interpretation of genetic variation presented here represent the next generation of genetic risk assessment using whole genome sequencing.

The current iteration of the human population-specific reference sequences includes only genetic variation data at single nucleotide polymorphisms, or substitutions at individual base pairs. Structural variation (stretches of DNA repeats, deletions, inversions, and translocations) comprises a large degree of human genetic variation. In a further embodiment of the present invention the major allele reference genomes are revised to incorporate known common structural variants specific to the population groups described above. As the quantification of genetic variation becomes more precise, mapping and variant calling algorithms can be developed that consider the full distribution of DNA bases at variant positions in the human genome, as opposed to simply the major allele as would be known to those of ordinary skill in the art.

As genetic variation data is cataloged on other population groups (e.g., Latin American, South Asian, Pacific Islander), additional major allele reference sequences can be developed for these population groups. They can then be implemented as described above for ethnicity-aware genome sequence interpretation.

It should be appreciated by those skilled in the art that the specific embodiments disclosed above may be readily utilized as a basis for modifying or designing other image processing algorithms or systems. It should also be appreciated by those skilled in the art that such modifications do not depart from the scope of the invention as set forth in the appended claims.

What is claimed is:

1. A method for providing genetic data over a network, comprising:
   obtaining reference sequence data describing a synthetic reference genome sequence,
      where the synthetic reference genome sequence is a composite sequence comprising a reference sequence substituted using major alleles for an ethnic sub-population,
      where major alleles are alleles having estimated allele frequencies of greater than 50% within the ethnic sub-population,
      and storing the reference sequence data using a computer system comprising a processor and a memory;
   obtaining individual sequence data describing information derived from an individual who is a member of the ethnic sub-population, comprising at least one short sequence read from the individual and storing the individual sequence data using a computer system comprising a processor and a memory;
   aligning the obtained at least one short sequence read to the synthetic reference genome sequence using a computer system comprising a processor and a memory;
   determining at least one difference between the at least one short sequence read and the synthetic reference genome sequence based on the alignment using a computer system comprising a processor and a memory; and
   transmitting the at least one difference to a remote device using a computer system comprising a processor and a memory.

2. The method of claim 1, wherein determining at least once difference between the at least one short sequence read and the synthetic reference genome sequence is performed for predetermined genomic positions.

3. The method of claim 1, wherein obtaining reference sequence data comprises generating the synthetic reference genome sequence by:
   selecting the ethnic sub-population from HapMap population groups;
   determining the major allele at allele positions, where the major allele is an allele estimated to have an allele frequency of greater than 50% in the ethnic sub-population;
   substituting the major allele from the ethnic sub-population into the reference sequence.

4. A non-transitory computer-readable medium including instructions that, when executed by a processing unit, cause the processing unit to provide genetic data over a network, by performing the steps comprising:
   obtaining reference sequence data describing a synthetic reference genome sequence,
      where the synthetic reference genome sequence is a composite sequence comprising a reference sequence substituted using major alleles for an ethnic sub-population, where major alleles are alleles having estimated allele frequencies of greater than 50% within the ethnic sub-population, and storing the reference sequence data using a computer system comprising a processor and a memory;

obtaining individual sequence data describing information derived from an individual, wherein the individual's ethnic background includes the ethnic sub-population, comprising at least one short sequence read from the individual and storing the individual sequence data;

aligning the obtained at least one short sequence read to the synthetic reference genome sequence;

determining at least one difference between the at least one short sequence read and the synthetic reference genome sequence based on the alignment; and transmitting the at least one difference to a remote device.

5. The non-transitory computer-readable medium of claim 4, wherein determining at least once difference between the at least one short sequence read and the synthetic reference genome sequence is performed for predetermined genomic positions.

6. The non-transitory computer-readable medium of claim 4, wherein the step for obtaining reference sequence data comprises a step for generating the synthetic reference genome sequence by:

selecting the ethnic sub-population from HapMap population groups;

determining the major allele at allele positions, where the major allele is an allele estimated to have an allele frequency of greater than 50% in the ethnic sub-population;

substituting the major allele from the ethnic sub-population into the reference sequence.

7. A computing device for providing genetic data over a network comprising: a data bus; a memory unit coupled to the data bus; a processing unit coupled to the data bus and configured to obtain reference sequence data describing a synthetic reference genome sequence, where the synthetic reference genome sequence is a composite sequence comprising a reference sequence substituted using major alleles for an ethnic sub-population, where major alleles are alleles having estimated allele frequencies of greater than 50% within the ethnic sub-population, and store the reference sequence data on a memory;

obtain individual sequence data describing information derived from an individual, wherein the individual's ethnic background includes the ethnic sub-population, comprising at least one short sequence read from the individual and store the individual sequence data on a memory;

align the obtained at least one short sequence read to the synthetic reference genome sequence;

determine at least one difference between the at least one short sequence read and the synthetic reference genome sequence based on the alignment; and transmit the at least one difference to a remote device.

* * * * *